US010500156B2

(12) United States Patent
Amiji et al.

(10) Patent No.: US 10,500,156 B2
(45) Date of Patent: Dec. 10, 2019

(54) MULTI-COMPARTMENTAL MACROPHAGE DELIVERY

(75) Inventors: Mansoor M. Amiji, Attleboro, MA (US); Mayur Kalariya, Natick, MA (US); Shardool Jain, Roxbury Crossing, MA (US); Husain Attarwala, Boston, MA (US)

(73) Assignee: Northeastern University, Boston, MA (US)

( * ) Notice: Subject to any disclaimer, the term of this patent is extended or adjusted under 35 U.S.C. 154(b) by 587 days.

(21) Appl. No.: 13/636,900

(22) PCT Filed: Mar. 24, 2011

(86) PCT No.: PCT/US2011/029860
§ 371 (c)(1),
(2), (4) Date: May 15, 2013

(87) PCT Pub. No.: WO2011/119881
PCT Pub. Date: Sep. 29, 2011

(65) Prior Publication Data
US 2013/0243689 A1  Sep. 19, 2013

Related U.S. Application Data

(60) Provisional application No. 61/317,052, filed on Mar. 24, 2010.

(51) Int. Cl.
| *A61K 9/113* | (2006.01) |
| *A61K 49/00* | (2006.01) |
| *A61K 47/69* | (2017.01) |
| *A61K 9/50* | (2006.01) |
| *A61K 9/51* | (2006.01) |
| *B82Y 5/00* | (2011.01) |
| *A61K 9/14* | (2006.01) |
| *A61K 38/19* | (2006.01) |
| *A61K 38/21* | (2006.01) |
| *A61K 39/39* | (2006.01) |
| *A61K 39/00* | (2006.01) |

(52) U.S. Cl.
CPC .............. *A61K 9/113* (2013.01); *A61K 9/145* (2013.01); *A61K 9/5031* (2013.01); *A61K 9/5161* (2013.01); *A61K 38/191* (2013.01); *A61K 38/217* (2013.01); *A61K 39/39* (2013.01); *A61K 47/6925* (2017.08); *A61K 47/6935* (2017.08); *A61K 49/0041* (2013.01); *A61K 49/0047* (2013.01); *A61K 49/0054* (2013.01); *A61K 49/0076* (2013.01); *A61K 49/0091* (2013.01); *A61K 49/0093* (2013.01); *B82Y 5/00* (2013.01); *A61K 9/5169* (2013.01); *A61K 2039/55555* (2013.01)

(58) Field of Classification Search
None
See application file for complete search history.

(56) References Cited

U.S. PATENT DOCUMENTS

| 2003/0207287 | A1 | 11/2003 | Short |
| 2006/0088533 | A1* | 4/2006 | Pothoulakis ........... C07K 16/22 424/145.1 |
| 2006/0204442 | A1* | 9/2006 | Tapolsky .............. A61K 9/5094 424/9.32 |
| 2007/0184068 | A1 | 8/2007 | Renner et al. |
| 2008/0153771 | A1* | 6/2008 | Liu et al. ........................ 514/44 |
| 2009/0004118 | A1* | 1/2009 | Nie et al. ..................... 424/9.35 |
| 2011/0177139 | A1 | 7/2011 | Jung et al. |
| 2011/0229580 | A1 | 9/2011 | Srivastava et al. |

FOREIGN PATENT DOCUMENTS

| CN | 101053810 A | 10/2007 |
| WO | WO-03043729 A1 | 5/2003 |
| WO | WO-2004065578 A2 | 8/2004 |
| WO | WO-2007014755 A1 | 2/2007 |
| WO | WO 2008115854 A2 * | 9/2008 ........... A61K 49/183 |
| WO | WO-2009046446 A2 | 4/2009 |
| WO | WO-2009051837 A2 | 4/2009 |
| WO | WO-2010148106 A1 | 12/2010 |
| WO | WO-2011026111 A1 | 3/2011 |

OTHER PUBLICATIONS

Higashi et al. Hepatic arterial injection chemotherapy for hepatocellular carcinoma with epirubicin aqueous solution as numerous vesicles in iodinated poppy-seed oil microdroplets: clinical application of water-in-oil-in-water emulsion prepared using a membrane emulsification technique. 2000 Adv. Drug Deliv. Rev. 45: 57-64.*
Bhavsar et al. Oral IL-10 gene delivery in a microsphere-based formulation for local transfection and therapeutic efficacy in inflammatory bowel disease. 2008 Gene Ther. 15: 1200-1209.*
Aouadi et al. Orally delivered siRNA targeting macrophage Map4k4 suppresses systemic inflammation. Apr. 30, 2009 Nature 458: 1180-1184.*
Bhavsar et al. Gastrointestinal distribution and in vivo gene transfection studies with nanoparticles-in-microsphere oral system (NiMOS). 2007 J. Control. Release 119: 339-348.*
Yang et al. Long-circulating near-infrared fluorescence core-cross-linked polymeric micelles: synthesis, characterization, and dual nuclear/optical imaging. 2007 Biomacromolecules 8: 3422-3428.*

(Continued)

*Primary Examiner* — Jennifer A. Lamberski
(74) *Attorney, Agent, or Firm* — Verrill Dana LLP

(57) ABSTRACT

Disclosed are multi-compartmental nanoparticulate systems for imaging as well as the diagnosis, monitoring, and treatment of inflammation and/or disease. These multicompartmental nanoparticulate systems can be used to target specific cells or cellular structures. Furthermore, these systems are capable of simultaneous delivery of hydrophilic and lipophilic compositions. Finally, these systems also allow for temporal control of drug delivery.

29 Claims, 31 Drawing Sheets

(56) References Cited

OTHER PUBLICATIONS

Kim et al. Designed fabrication of a multifunctional polymer nanomedical platform for simultaneous cancer-targeting imaging and magnetically guided drug delivery. 2008 Adv. Mater. 20: 478-483.*
Davis et al. Multiple emulsions as targetable delivery systems. 1987 Methods Enzymol. 149: 51-64.*
Bae et al. Ultrasmall iron oxide nanoparticles: synthesis, physicochemical, and magnetic properties. 2009 Curr. Appl. Phys. 9: S19-S21. Published online Sep. 9, 2008.*
Danese et al. Angiogenesis as a novel component of inflammatory bowel disease pathogenesis. 2006 Gastroenterology 130: 2060-2073.*
Torrente et al. High-resolution X-ray microtomography for three-dimensional visualization of human stem cell muscle homing. 2006 FEBS Lett. 580: 5759-5764. (Year: 2006).*
McCarthy et al. A macrophage-targeted theranostic nanoparticle for biomedical applications. 2006 Small 2: 983-987. (Year: 2006).*
Pande et al. Detection of macrophage activity in atherosclerosis in vivo using multichannel, high-resolution laser scanning fluorescence microscopy. 2006 J. Biomed. Opt. 11: 021009. 7 p. (Year: 2006).*
Ahsan et al. Targeting to macrophages: role of physicochemical properties of particulate carriers—liposomes and microspheres—on the phagocytosis by macrophages. 2002 J. Control. Release 79: 29-40. (Year: 2002).*
Namiki et al. Intramuscular gene transfer of interleukin-10 cDNA reduces atherosclerosis in apolipoprotein E-knockout mice. 2004 Atherosclerosis 172: 21-29. (Year: 2004).*
Godillot, et al., "DNA vaccination as an anti-inflammatory strategy," In P.D.R. C.H. Evans (Ed), Gene Therapy in Inflammatory Diseases, Progress in Inflammation Research, Birkhauser Verlag, Basel, Switzerland, pp. 205-229 (2000).
Balmayor et al., "Synthesis and Functionalization of Superparamagnetic Poly-ε-Caprolactone Microparticles for the Selective Isolation of Subpopulations of Human Adipose-derived Stem Cells," J. R. Soc. Interface, vol. 8, pp. 896-908 (2011).
Barbato et al., "Biodegradable microspheres of novel segmented poly(ether-ester-amide)s based on poly(ε-caprolactone) for the delivery of bioactive compounds," Biomaterials, vol. 22(11), pp. 1371-1378 (2001).
Bhavsar, et al., "Formulation optimization for the nanoparticles-in-microsphere hybrid oral delivery system using factorial design," Journal of Controlled Release, vol. 110, No. 2, pp. 422-430 (Jan. 10, 2006).
Bhavsar, M.D. and Amiji, M.M., "Development of novel biodegradable polymeric nanoparticles-in-microsphere formulation for local plasmid DNA delivery in the gastrointestinal tract," Aaps Pharmscitech, vol. 9, No. 1, pp. 288-294 (Mar. 2008).
Bhavsar, M.D. and Amiji, M.M., "Polymeric nano- and microparticle technologies for oral gene delivery," Expert Opinion on Drug Delivery, vol. 4, No. 3, pp. 197-213 (May 2007).
Bozan, B. and Temelli, F., "Chemical Composition and Oxidative Stability of Flax, Safflower and Poppy Seed and Seed Oils," Bioresour Technol., vol. 99, pp. 6354-6359 (2008).
Bumgarner, et al.,"Surface Engineering of Microparticles by Novel Protein Transfer for Targeted Antigen/Drug Delivery," J Control Release, vol. 137, No. 2, pp. 90-97 (Jul. 20, 2009).
Burke et al., "Macrophages in Gene Therapy: Cellular Delivery Vehicles and in Vivo Targets," Journal of Leukocyte Biology, vol. 72, pp. 417-428 (2002).
De Bandt, et al., "Vitamin E uncouples joint destruction and clinical inflammation in a transgenic mouse model of rheumatoid arthritis," Arthritis Rheum., vol. 46, pp. 522-532 (2002).
Devaraj, S. and Jialal, I., "Alpha-tocopherol decreases interleukin-1 beta release from activated human monocytes by inhibition of 5-lipoxygenase," Arterioscler Thromb Vasc Biol., vol. 19, pp. 1125-1133 (1999).
Devaraj, S. and Jialal, I., "Alpha-tocopherol decreases tumor necrosis factor-alpha mRNA and protein from activated human monocytes by inhibition of 5-lipoxygenase," Free Radic Biol Med., vol. 38, pp. 1212-1220 (2005).
Diez, S. and De Ilarduya, C.T., "Versatility of biodegradable poly(D,L-lactic-co-glycolic acid) microspheres for plasmid DNA delivery," European Journal of Pharmaceutics and Biopharmaceutics, vol. 63, pp. 188-197 (2006).
Elson, et al., "Oral-antigen delivery by way of a multiple emulsion system enhances oral tolerance," Ann N Y Acad Sci., vol. 778, pp. 156-162 (1996).
Fattal, E. and Bochot, A., "State of the art and perspectives for the delivery of antisense oligonucleotides and siRNA by polymeric nanocarriers," International Journal of Pharmaceutics, vol. 364, pp. 237-248 (2008).
Fujiwara, N. and Kobayashi, K., "Macrophages in Inflammation," Current Drug targets-Inflammation & Allergy, vol. 4, pp. 281-286 (2005).
Furtado Mosqueira, et al., "Poly(D,L-lactide) nanocapsules prepared by a solvent displacement process: Influence of the composition on physicochemical and structural properties," Journal of Pharmaceutical Sciences Special Issue: Papers from the 1999 Macromolecular Drug Delivery Conference, vol. 89(5), pp. 614-626 (2000).
Gardea-Torresdey, et al., "Gold Nanoparticles Obtained by Bioprecipitation from Gold(III) Solutions," Journal of Nanoparticle Research, vol. 1(3), pp. 397-404 (1999).
Gou et al, "Poly(ε-caprolactone)-poly(ethylene glycol)poly(ε-caprolactone) (PCL-PEG-PCL) nanoparticles for honokiol delivery in vitro," Int. J. Pharmaceutics, vol. 375 (1-2), pp. 170-176 (Jun. 22, 2009).
Griffiths et al., "The Macrophage—a Novel System to Deliver Gene Therapy to Pathological Hypoxia," Gene Therapy, vol. 7, pp. 255-262 (2000).
International Search Report and Written Opinion issued by the U.S. Patent and Trademark Office as International Searching Authority for International Application No. PCT/US2011/29860 dated Jun. 9, 2011 (11 pgs.).
Kaul, G. and Amiji, M. Tumor-targeted gene delivery using poly-(ethylene glycol)-modified gelatin nanoparticles: in vitro and in vivo studies. Pharmaceutical Research, vol. 22, No. 6, pp. 951-961 (2005).
Lopes, et al., "The macrophage haunted by cell ghosts: a pathogen grows," Immunology today, vol. 21, pp. 489-494 (2000).
Luciani, et al., "PCL microspheres based functional scaffolds by bottom-up approach with predefined microstructural properties and release profiles," Biomaterials (2008) 29(36): 4800-4807.
Luna Martinez et al., "Iron Oxide Nanoparticles Obtained from a Fe(II)—Chitosan Polymer Film," Mater. Sci. Forum: Adv. Elec. Microscop. Nanomat. (2010) 644: 51-55.
Macdiarmid, et al.,"Sequential treatment of drug-resistant tumors with targeted minicells containing siRNA or a cytotoxic drug," Nature Biotechnology, vol. 27, pp. 643-651 (2009).
Magadala et al., "Epidermal Growth Factor Receptor-Targeted Gelatin-Based Engineered Nanocarriers for DNA Delivery and Transfection in Human Pancreatic Cancer Cells," AAPSJ., vol. 10(4), pp. 565-576 (2008).
Masterjohn, C., "The anti-inflammatory properties of safflower oil and coconut oil may be mediated by their respective concentrations of vitamin E," J Am Coll Cardiol., vol. 49, pp. 1825-1826 (2007).
Oster et al., "DNA nano-carriers from biodegradable cationic branched polyesters are formed by a modified solvent displacement method," Journal of Controlled Release, vol. 111(3), pp. 371-381 (2006).
Peer, et al., "Systemic leukocyte-directed siRNA delivery revealing cyclin D1 as an anti-inflammatory target," Science, vol. 319, pp. 627-630 (2008).
R.J. Mrsny. "Tissue-and Cell-Specific Targeting for the Delivery of Genetic Information," In M.M. Amiji (Ed), Polymeric Gene Delivery: Principles and Applications, CRC Press, Boca Raton, FL. 2005, pp. 5-27.
Ribeiro, et al. "Preparation of nanodispersions containing β-carotene by solvent displacement method," Food Hydrocolloids, vol. 22(1), pp. 12-17 (2008).

(56) References Cited

OTHER PUBLICATIONS

Rosca, et al., "Microparticle formation and its mechanism in single and double emulsion solvent evaporation," Journal of Controlled Release, vol. 99(2), pp. 271-280 (2004).

Shahiwala, A. and Amiji, M.M., "Enhanced mucosal and systemic immune response with squalane oil-containing multiple emulsions upon intranasal and oral administration in mice," J Drug Target, vol. 16, pp. 302-310 (2008).

Sorensen, et al., "Gene silencing by systemic delivery of synthetic siRNAs in adult mice," Journal of Molecular Biology, vol. 327, pp. 761-766 (2003).

Suzuki, et al., "Enhanced colonic and rectal absorption of insulin using a multiple emulsion containing eicosapentaenoic acid and docosahexaenoic acid," J Pharm Sci., vol. 87, pp. 1196-1202 (1998).

Sy, et al., "Surface functionalization of polyketal microparticles with nitrilotriacetic acid-nickel complexes for efficient protein capture and delivery," Biomaterials, vol. 31(18), pp. 4987-4994 (2010).

Tracy, M., "Development and scale-up of a microsphere protein delivery system," Biotechnological Progress, vol. 14, pp. 108-115 (1998).

Xu, D. et al. "Delivery of MDR1 small interfering RNA by self-complementary recombinant adeno-associated virus vector," Molecular Therapy 11, 523-530 (2005).

Yang et al, "Preparation of poly ε-caprolactone nanoparticles containing magnetite for magnetic drug carrier," Int. J. Pharmaceutics, vol. 324(2), pp. 185-190 (Nov. 6, 2006).

Zhou et al., "A Novel Ultraviolet Irradiation Technique for Shape-Controlled Synthesis of Gold Nanoparticles at Room Temperature," Chem. Mater., vol. 11(9), pp. 2310-2312 (1999).

Extended European Search Report issued by the European Patent Office for European Patent Application No. 11760255.7 dated Feb. 1, 2016 (13 pgs.).

\* cited by examiner

FIG. 3A

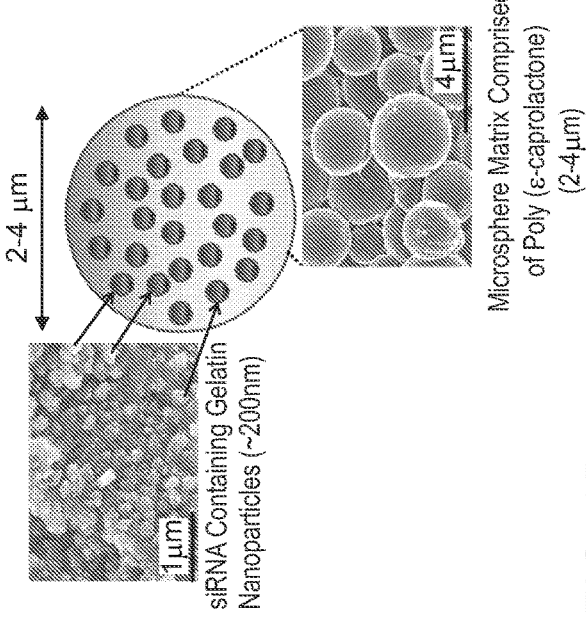

FIG. 3C

| Formulation | Number Diameter* | Poly-dispersity | siRNA Encapsulation Efficiency |
|---|---|---|---|
| Blank Nanoparticles | 207.0 ± 1.8nm | 0.043 | - |
| siRNA encapsulated Nanoparticles | 279.2 ± 3.2nm | 0.073 | 90.2 ± 5.4% |
| Blank NiMOS | 3.1 ± 0.7μm | N/A | - |
| siRNA encapsulated NiMOS | 2.4 ± 0.9μm | N/A | 55.2 ± 2.8% |

FIG. 3B

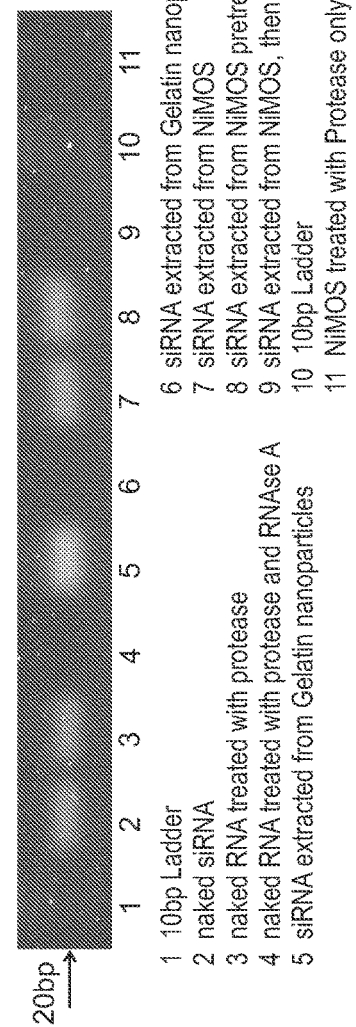

1 10bp Ladder
2 naked siRNA
3 naked RNA treated with protease
4 naked RNA treated with protease and RNAse A
5 siRNA extracted from Gelatin nanoparticles
6 siRNA extracted from Gelatin nanoparticles, then treated with RNAse A
7 siRNA extracted from NiMOS
8 siRNA extracted from NiMOS pretreated with RNAse A
9 siRNA extracted from NiMOS, then treated with RNAse A
10 10bp Ladder
11 NiMOS treated with Protease only

| Formulation | Number Diameter* | Polydispersity Index | siRNA Encapsulation Efficiency (%) |
|---|---|---|---|
| Blank Nanoparticles | 207.0 ± 1.8nm | 0.043 | - |
| siRNA encapsulated Nanoparticles | 279 ± 3.2nm | 0.073 | 90.2 ± 5.4% |
| Blank NiMOS | 3.1 ± 0.7μm | N/A | - |
| siRNA encapsulated NiMOS | 2.4 ± 0.9μm | N/A | 55.2 ± 2.8% |

*Mean ± S.D. (n=4)

FIG. 20

Lane 1: 2-10kb super-coiled DNA ladder.
Lane 2: Blank NiE formulation.
Lane 3: EGFP-N1 plasmid DNA isolated from NiE formulation.
Lane 4: EGFP-N1 plasmid DNA isolated from ME formulation.
Lane 5: EGFP-N1 plasmid DNA isolated from gelatin nanoparticles.
Lane 6: Blank gelatin nanoparticles.
Lane 7: Pure EGFP-N1 plasmid DNA as a control.
Lane 8: EGFP-N1 plasmid DNA isolated from ME formulation after spiking with the plasmid.
Lane 9: 2-10kb supercoiled DNA ladder.

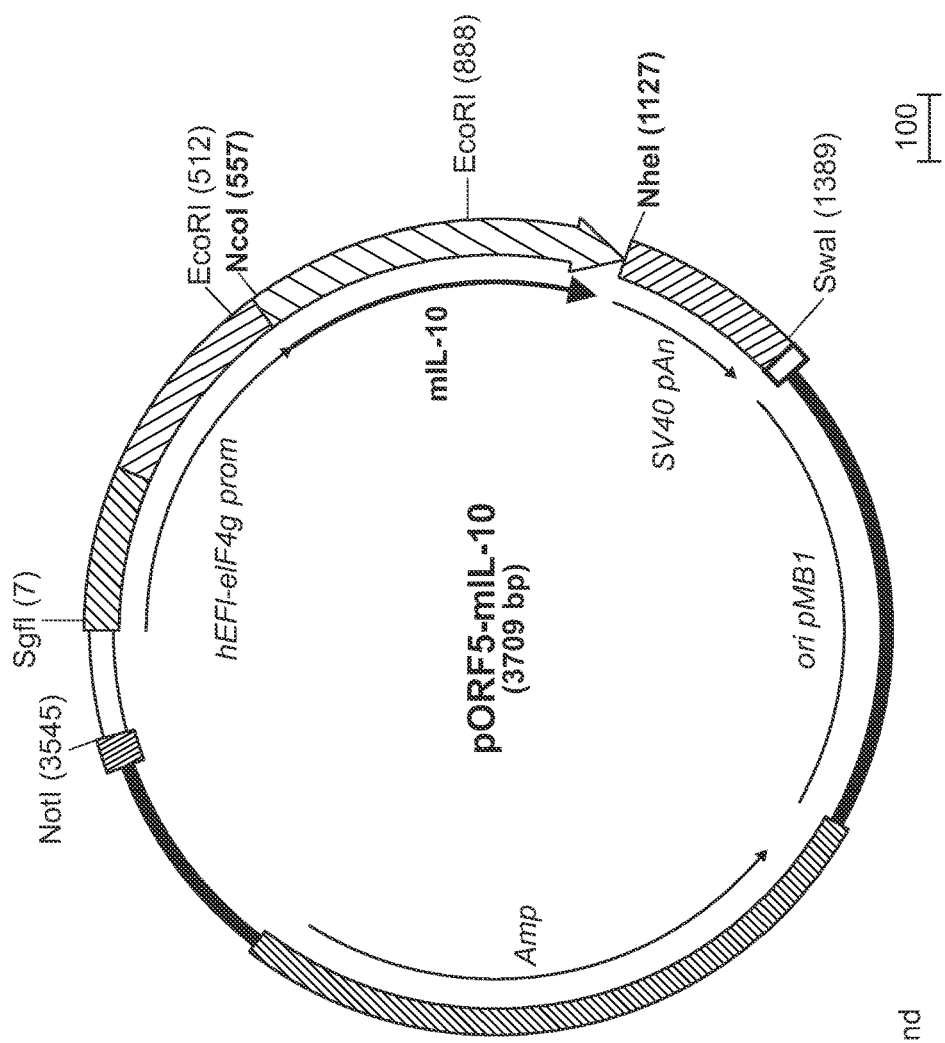
FIG. 25
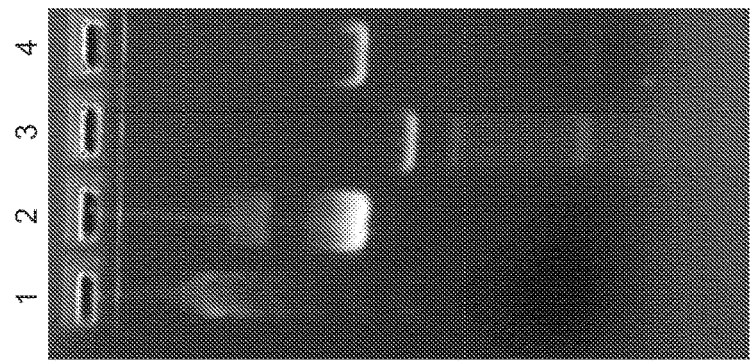
Lane 1: Supercoiled DNA ladder 2-10 kb.
Lane 2: Undigested plasmid IL-10.
Lane 3: 100 - 1500 bp DNA ladder.
Lane 4: IL-10 plasmid digested with NCO-I and NHE-1 restriction enzymes.

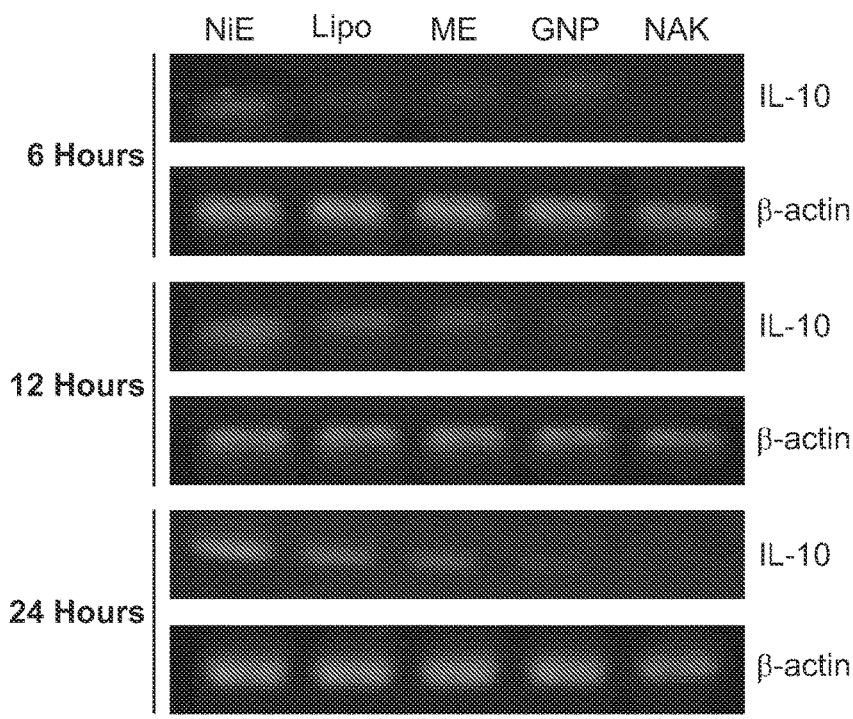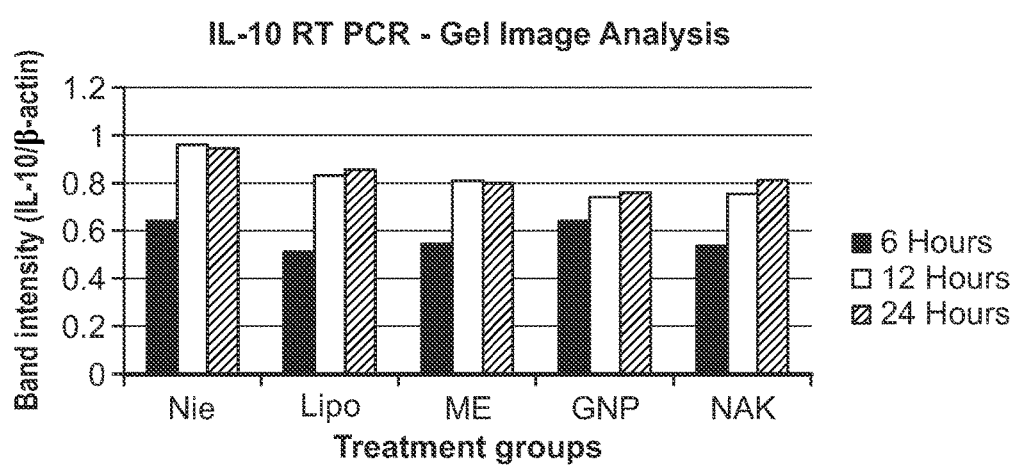
FIG. 26

MULTI-COMPARTMENTAL MACROPHAGE DELIVERY

CROSS-REFERENCE TO RELATED APPLICATIONS

This application is a U.S. National Phase Application under 35 U.S.C. § 371 of International Patent Application No. PCT/US2011/29860 filed Mar. 24, 2011, and published as WO 2011/119881 on Sep. 29, 2011, which claims the benefit of priority to U.S. Provisional Application No. 61/317,052, filed Mar. 24, 2010, the specification of which is incorporated by reference in its entirety.

FEDERALLY SPONSORED RESEARCH OR DEVELOPMENT

This invention was made with government support under Grant No. R01-DK080477 awarded by the National Institutes of Health. The government has certain rights in the invention.

FIELD OF THE INVENTION

This disclosure is in the field of medicine, and more specifically relates to a multi-compartmental nanoparticulate system for diagnosing, monitoring, and treating inflammation and/or disease. These systems are capable of targeting specific cell types, co-administration of incompatible materials, as well as temporal control of payload release.

BACKGROUND

Macrophages are important immune cells in the body that regulate different biological processes involved in inflammatory and infectious diseases. Macrophages originate from the mononuclear phagocyte system (MPS) in the bone marrow. The MPS system is comprised of monocytes and tissue macrophages in their various forms. The primary function of monocytes is phagocytosis. Upon exiting the bone marrow, monocytes circulate in the blood and become activated in various tissues. Once the monocyte reaches the extravascular tissue, it matures into a larger phagocytic cell called a macrophage. They reside in the liver (Kupffer cells), lungs (alveolar macrophages), spleen, lymph nodes, thymus, gut, marrow, brain, connective tissue and serous cavities.

In order to combat inflammation and infections, macrophages are converted from the rested to an activated state. The activated cells have an enhanced capability to attack and kill infecting pathogens and tumor cells.

The active state is marked by an increase in size and the development of more psuedopods (cellular projections). The cytokines released from T-lymphocytes such as interferon-gamma (IFN-γ), tumor necrosis factor-alpha (TNF-α) and granulocyte-monocyte colony stimulating factor (GM-CSF) can act as signals to activate macrophages. Additionally, the activating signal can come from microbial products such as lipopolysaccharides, immune complexes, chemical mediators, and extracellular matrix proteins including fibronectin.

SUMMARY

The instant disclosure is directed towards methods of imaging, diagnosing, and/or treating a disease or condition. The multicompartmental delivery systems described herein allow for the administration of one or more agents such as, but not limited to, imaging agents, diagnostic agents, therapeutic agents, vaccines, proteins, gene constructs, and small molecules. These systems allow for co-administration of incompatible agents (i.e., hydrophobic and hydrophilic agents), as well as temporal control over the release of administered agents.

All publications, patent applications, patents, and other references mentioned herein are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this disclosure belongs. Although methods and materials similar or equivalent to those described herein can be used in the practice or testing of the systems and methods described in the disclosure, suitable methods and materials are described below.

BRIEF DESCRIPTION OF THE DRAWING

FIG. 3A-C: Schematic representation of the nanoparticles in-microsphere (NiM) delivery vehicle including scanning electron micrographs of small interfering RNA (siRNA) .encapsulated type B gelatin nanoparticles and siRNA-containing NiM. The magnification is represented by a scale bar in the lower right comer of each image. b) Qualitative agarose gel (4% (w/v» electrophoresis to show stability of siRNA in the NiM. c) The siRNA-encapsulated gelatin nanoparticles had an average diameter of less than 300 nm with a narrow size distribution, and an encapsulation efficiency of approximately 90±5%. siRNA encapsulated NiM had an average diameter of 2.4±0.9 IJm with a narrow size distribution. Encapsulating efficiency of siRNA decreased to approximately 55±3% in NiM.

FIG. 20: Determination of EGFP-N1 plasmid DNA stability by agarose gel electrophoresis.

FIG. 25: (A) Agarose gel electrophoresis showing intact plasmid of approximately 3.7 kilo base pairs (lane 2). Lane 4 shows presence of a DNA fragment of approximately 500 bps in size correlating with size of IL-10 transgene in the plasmid vector. (B) mIL-10 plasmid constructs.

FIG. 26: Qualitative IL-10 mRNA expression by RT-PCR in J774A.1 cells. NiE formulations showed higher mIL-10 transgene transcript expression relative to all other tested.

DETAILED DESCRIPTION

Figure 1:
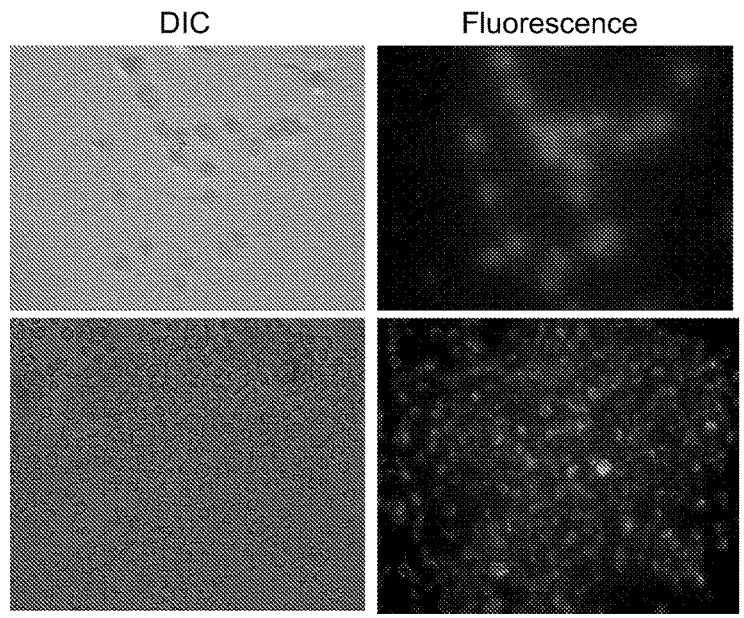
FIG. 1: Differential interference contrast and fluorescence microscopy images of cellular uptake and green fluorescent protein (GFP) transfection in adherent J774A.1 murine alveolar macrophages using nanoparticles-in-emulsion (NiE) formulations. The uptake studies were carried out with rhodamine-labeled gelatin nanoparticles in safflower oil containing water-in-oil-in-water (W/O/W) multiple emulsion and the GFP transfection after 24 hours was observed with EGFP-N1 plasmid DNA-encapsulated gelatin nanoparticles in NiE

This disclosure is related in part to a composition of matter for safe and efficient delivery of image contrast agents, drugs, genes, small interfering RNA (siRNA), and vaccination molecules to macrophages upon administration in the body by oral, nasal, inhalation, injection or any other route known to those skilled in the art.

1. Multicompartment Delivery Systems

The instant disclosure is directed towards a multicompartment delivery system comprising one or more inner aqueous compartments encapsulated within an outer hydrophobic compartment, the outer hydrophobic compartment being surrounded by an exterior aqueous compartment. In some embodiments of the system, a first agent encapsulated within the one or more inner aqueous compartments. In other embodiments, the first agent is selected from the group consisting of an imaging agent, a diagnostic agent, a therapeutic agent, a vaccine, a protein, or a gene construct. In still other embodiments, a second agent is encapsulated within the outer hydrophobic compartment. Encapsulated is defined herein to include dissolved in a material, associated with a material, meaning that an agent or nanoparticle can be on the surface, within the material, or surrounded by the material that comprises the compartment. The second agent can be selected from the group consisting of an imaging agent, a diagnostic agent, a therapeutic agent, a vaccine, a protein, or a gene construct.

The multicompartment delivery system disclosed herein can also comprise an outer compartment that forms a microsphere. Methods of producing a microsphere are known in the art and include the single emulsion method and solvent displacement method (see, e.g., Furtado Mosqueira et al. *Journal of Pharmaceutical Sciences Special Issue: Papers from the* 1999 *Macromolecular Drug Delivery Conference* (2000) 89(5): 614-626; Rosca et al. *Journal of Controlled Release* (2004) 99(2): 271-280). The microsphere can be about 0.5 to 500 microns in size. In some embodiments the inner aqueous compartment is about 50 nm to about 300 nm. In still other embodiments, the inner aqueous compartment comprises nanoparticles. In another embodiment the nanoparticles comprise gelatin or alginate.

In still other embodiments of the multicompartment delivery systems, the outer hydrophobic compartment comprises safflower oil. In some embodiments, one or more target-specific binding agents are attached to the surface of the outer hydrophobic compartment. In some embodiments, the one or more target-specific binding agents attached to the surface of the outer hydrophobic compartment is tuftsin. Methods of attaching binding agents to a particle or carrier are known in the art (see, e.g., Magadala et al. AAPS J. (2008) 10(4): 565-576).

In some embodiments, the exterior aqueous compartment comprises water. In other embodiments, the multicompartment delivery system further comprising one or more target-specific binding agents attached to the surface of the inner aqueous compartment or the outer hydrophobic compartment. In still other embodiments, one or more target-specific binding agents are attached to the inner aqueous compartment and the outer hydrophobic compartment. Further embodiments further comprise one or more target-specific binding agents attached to the inner aqueous compartment, direct the inner compartment to an intracellular location and the one or more target-specific binding agents attached to the outer hydrophobic compartment direct the microsphere to a cell.

The delivery vehicles disclosed herein are specifically designed to have multiple compartments (multicompartment) to afford the following two advantages: (1) ability to sequester the payload in each of the compartment due to incompatibility (e.g., poor solubility), instability, or desire for temporal-controlled release and delivery; and (2) ability to overcome the different tissue, cell, and intracellular barriers to afford efficient delivery of the payload to the desired biological target site. This is especially critical for nucleic acid-based therapeutics such as genes, oligonucleotides, and siRNA.

As shown in FIG. 1, the multi-compartmental delivery systems are designed to meet the needs of the payload (e.g., hydrophobic versus hydrophilic), the site of delivery in the body, the intended application (e.g., drugs versus vaccines), and the disease of interest.

The multicompartment delivery vehicles disclosed herein can be nanoparticles-in-microspheres (FIG. 3). Nanoparticles-in-microspheres can have an outer compartment (i.e., microsphere). In certain embodiments, the microsphere is a "solid." As used herein, the term "solid" means a substance that is structurally rigid and resistant to changes in shape. Such microspheres are composed of materials such as poly (epsilon-caprolactone), (PCL), poly(D,L-lactide-co-glycolide) (PLGA), and polymethylmethacrylate. The microspheres can be from about 500 nanometers to about 1.5 microns.

In certain embodiments, the microspheres encapsulate solid nanoparticles that form an inner compartment. The nanoparticles can be composed of a material different from the microsphere. For instance, the nanoparticles that are composed of hydrophilic materials are encapsulated within microspheres composed of hydrophobic materials. In certain embodiments, hydrophobic nanoparticles are encapsulated within hydrophilic microspheres The hydrophobic microsphere can be composed of an oil such as safflower oil or any other biologically compatible oil, a wax or hydrophobic molecules such as poly(epsilon-caprolactone), (PCL), poly (D,L-lactide-co-glycolide) (PLGA), and polymethylmethacrylate. Such nanomaterials can be obtained from Phosphorex Inc. (Fall River, Mass.). In addition methods of making nanoparticles are known in the art (see, e.g., Yang et al., Int. J. Pharmaceutics (2006) 324 (2):185-190); Gou et al., Int. J. Pharmaceutics (2009) 375 (1-2):170-176). In all embodiments disclosed herein, the nanoparticles can be from about 20 nanometers ("nm") to about 300 nanometers; from about 20 nm to about 30 nm; from about 30 nm to about 40 nm; from about 40 nm to about 50 nm; from 50 nm to about 100 nm; from about 100 nm to about 150 nm; from about 150 nm to about 200 nm; from about 200 nm to about 250 nm; and from about 250 to about 300 nm.

Figures 2A, 2B, 2C:
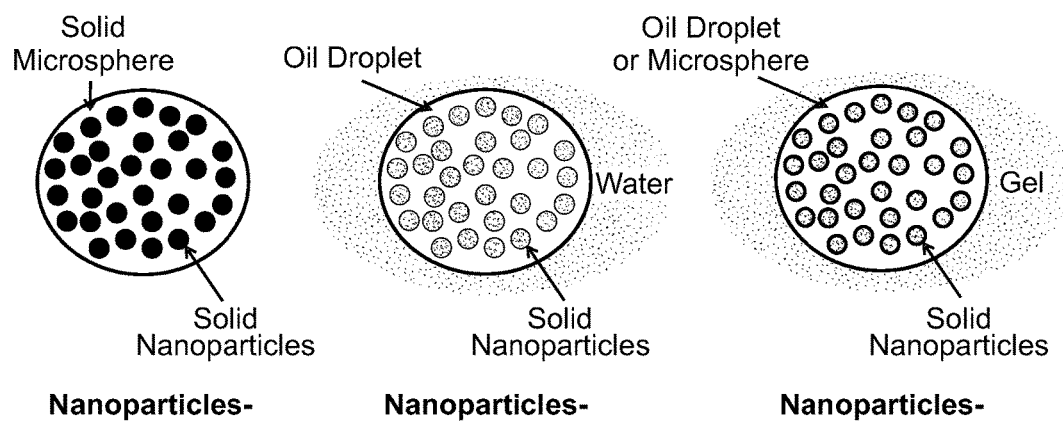
FIG. 2A-C: Illustrative examples of multi-compartmental delivery systems of the invention. The formulations can be designed to have solid hydrophilic or hydrophobic nanoparticles in a larger solid microsphere (a), nanoparticles in water-in-oil-in-water multiple emulsions (b), or nanoparticles or oil droplets in a gel (c), etc. The combination of different constructs is based on the properties of the payload and the desired application of the system.

The multicompartment delivery systems disclosed herein can have more than two distinct compartments (FIGS. 2b and 2c). For instance, the multicompartment delivery system can comprise 3 compartments. In certain embodiments, the nanoparticles are solid and hydrophilic. The nanoparticles can be encapsulated in a hydrophobic microsphere, which forms an outer hydrophobic compartment. The hydrophobic microsphere can be composed of oil, such as safflower oil or any other biologically compatible oil, a wax, or hydrophobic molecules such as poly(epsilon-caprolactone), (PCL), poly (D,L-lactide-co-glycolide) (PLGA), and polymethylmethacrylate. Such microspheres can be obtained commercially from Spherotech, Inc. (Lake Forest, Ill.). Methods for making microspheres are also known in the art (see, e.g., Barbato et al. *Biomaterials* (2001) 22(11): 1371-8; Luciani et al. *Biomaterials* (2008) 29(36): 4800-7). This structure can have a third compartment that encapsulates the microsphere. This compartment is an compartment (FIGS. 2b and 2c). For instance, the microsphere can be surrounded by a gel such as gelatin. The microsphere can be surrounded by water.

The multicompartment delivery systems of the present disclosure can also be modified by target-specific binding agents that target the delivery systems to a cell or tissue. Examples of target-specific binding agents are antibodies, Fab fragments and other antibody binding fragments, ligands, peptides, small molecules, and peptidomimetic compounds. In specific embodiments, the target-specific binding agent is Tuftsin. In other embodiments, the target-specific binding agent is arginine-glycine-aspartate ("RGD") tripeptide. In particular embodiments, the multicompartment delivery systems are targeted to macrophages using specific peptides functionalized on the surface of the outer compartment. For instance, the outer compartment of the multicompartmental delivery system can have target-specific binding agents attached to its surface.

In addition, the multicompartment delivery systems encapsulate therapeutic or imaging agents. Such agents can be encapsulated within the inner compartment, outer compartment, or both. In certain embodiments, the agent can promote pro- or anti-inflammatory properties (e.g., ovalbumin for pro-inflammation and immune-adjuvant response or omega-3 fatty acid-containing oils for anti-inflammatory response) to further enhance the therapeutic efficiency of the system. The agents can be therapeutic agents such as chemotherapeutics, radioisotopes, antibiotics, peptides, vaccines, small molecules, proteins, and antibody therapeutics. In addition, the therapeutic agents can be nucleic acids used for gene therapy. In certain embodiments, the therapeutic agents are DNA molecules. Agents can be siRNA molecules delivered to silence genes in specific tissues.

One of the many advantages of the multicompartmental delivery systems disclosed herein is they utilize a compartmentalized delivery system which can be used to shield payloads prone to degradation until they have reached the target of interest. This is important for successful gene therapy, as macrophages, a preferred target cell, contain large amounts of nucleases within their lysosomes, making it likely that without the protection of these disclosed systems, that the DNA payload delivered to a cell would be degraded.

2. Methods of Using Multicompartment Delivery Systems

In some embodiments, the method of imaging and treating a tissue with a multicompartment delivery system disclosed herein comprises (a) administering an effective amount of the multicompartment delivery system to a subject, the delivery system comprising one or more inner compartments encapsulated within an outer compartment, the one or more inner compartments being about 10 nm to about 300 nm and the outer compartment being from out 0.5 microns to about 20 microns, the one or more inner compartments further comprising a first material having a first physical property, the outer compartment comprising a second material having a second physical property that is different from the first physical property, the one or more inner compartments encapsulates a first agent; (b) allowing the multicompartment delivery system to selectively bind to a target tissue or a cell; and (c) delivery of therapeutic agent. (d) detecting the imaging agent in the subject.

In some embodiments of this method, the inner compartment is in the size range of about 10 nm to about 30 nm. In other embodiments, the first agent is an imaging agent. In still other embodiments, the first agent is colloidal gold, iron-oxide crystals, quantum dots, fluorophores, radiolabels, X-ray contrast agents, and positron emission tomographic agents.

In still other embodiments, the first agent is a therapeutic agent. In some aspects of the disclosure, the first agent is selected from the group consisting of chemotherapeutics, antibiotics, antivirals, small molecules, siRNA, and DNA.

In some embodiments, the outer compartment encapsulates a second agent. In some aspects, the second agent is an imaging agent. This imaging agent can be selected from the group consisting of fluorophores, radiolabels, X-ray contrast agents, and positron emission tomographic agents. In other aspects, the second agent is a therapeutic agent. The outer compartment or inner compartment of the delivery vehicle can encapsulate the one or more imaging agents. As used herein, the term "encapsulate" means to enclose within or associate with the polymeric carrier. The encapsulation can include association of a molecule or compound at the surface of the polymeric carrier or within the polymeric carrier. Such imaging agents include fluorophores, radiolabels, X-ray contrast, RAMAN spectroscopy agents, and positron emission tomography agents. Examples of fluorophores include rhodamine, fluorescein, isothiocyanate, phycoerythrin, phycocyanin, fluorescamine, and metal chelates. Examples of radiolabels include $^{3}H$, $^{123}I$, $^{125}I$, $^{131}I$, $^{32}P$, $^{35}S$, $^{14}C$, $^{51}Cr$, $^{36}Cl$, $^{57}Co$, $^{55}Fe$, $^{59}Fe$, $^{90}Y$, $^{99}$ mTc (metastable isomer of Technetium 99), and $^{75}Se$.

Furthermore, X-ray contrast agents include Diatrizoate (Hypaque 50), Metrizoate (Isopaque 370), Ioxaglate (Hexabrix), Iopamidol (Isovue 370), Iohexyl (Omnipaque 350), Ioxilan (Oxilan 350), Iopromide (Ultravist 370), and Iodixanol (Visipaque 320). Other agents include 2,2,6,6-tetramethylpiperidine-1-oxyl (TEMPO) group, DID fluorescent dye analogs, and perdeuterated alkyl or aryl phosphonium groups. Methods of encapsulating imaging agents within a particle are known in the art. For instance, the solvent displacement method has been used to encapsulating nucleic acids, small molecules, and peptides (see, e.g., Oster et al. *Journal of Controlled Release* (2006) 111(3): 371-381; Ribeiro et al. *Food Hydrocolloids* 22(1): 12-17).

In still other aspects, the second agent is selected from the group consisting of chemotherapeutics, antibiotics, antivirals, small molecules, anti-inflammatory agents, siRNA, and DNA.

In some embodiments the first material is poly(epsilon-caprolactone). In other embodiments, the first material is hydrophilic. In still other embodiments, the first material is aqueous. In still others, the second material is hydrophobic. In some aspects, the second material is safflower oil.

In still other embodiments, the outer compartment is encapsulated within an exterior compartment. In some aspects of the disclosure, the exterior compartment comprises an aqueous material.

In some embodiments, a target-specific binding agent is attached to the surface of the outer compartment. In some aspects, the target-specific binding agent is selected from the group consisting of antibodies and binding fragments thereof, peptide sequences, and ligands and binding fragments thereof. In still other aspects, the target-specific binding agent is an EGFR-specific antibody. In other aspects, the target-specific binding agents bind to alpha-V-beta III integrin receptor.

Derivatization of organic polymers can be performed to expose selected reactive groups at their surface (see, e.g., Townsend, S. A, et al. *Biomaterials* (2007) 28(34): 5176-5184; Weiss, B., et al. *Bioconjugate Chemistry* (2007) 18(4): 1087-1094; and Gindy, M. E., et al. *PMSE Preprints* (2006) 95:989-990). Furthermore, attaching target-specific binding agents, such as proteins, peptides, antibodies, and small molecules, to a polymer is known in the art (see, e.g., U.S. Pat. No. 7,022,336; Bumgarner et al. *J Control Release* (2009) 137(2):90-7; Sy et al. Biomaterials (2010) 31(18): 4987-94; Balmayor et al. *J. R. Soc. Interface* (2011) 10.1098/rsif.2010.0531). A target-specific binding agent can be a small molecule that binds a target, ligand, peptide (e.g., arginine-glycine-aspartate ("RGD") tripeptide), protein, antibody, Fab fragment, F(ab')2 fragments, and peptidomimetic compounds. Exemplary targets include receptors (e.g., alpha-V-beta III integrin receptor and EGFR receptor), phospholipids, glycoproteins, and proteins.

The instant disclosure also teaches methods of treating a disease with a multicompartment delivery system, the method comprising: (a) administering an effective amount of the multicompartment delivery system to a subject, the delivery system comprising one or more inner compartments encapsulated within an outer compartment, the one or more inner compartments comprising a first material having a first physical property, the outer compartment comprising a second material having a second physical property that is different from the first physical property, the one or more inner compartments being about 10 nm to about 300 nm and the outer compartment being from out 0.5 microns to about 20 microns, the one or more inner compartments further comprising a first therapeutic agent; (b) allowing the multicompartment delivery system to selectively bind to a target tissue or cell; and (c) releasing the therapeutic agent.

In some embodiments, the disease is selected from the group consisting of atherosclerosis, Crohn's disease, inflammatory bowel disease, rheumatoid arthritis and cancer. In some embodiments, the one or more inner compartment is in the size range of about 10 nm to about 30 nm. In still other embodiments, the one or more inner compartments or the outer compartments encapsulate an imaging agent. In some aspects, the imaging agent is selected from the group consisting of colloidal gold, iron-oxide crystals, quantum dots, fluorophores, radiolabels, X-ray contrast agents, and positron emission tomographic agents.

In some embodiments, the therapeutic agent is selected from the group consisting of chemotherapeutics, anti-inflammatories, fatty acids, antibiotics, antivirals, small molecules, siRNA, and DNA. In still other embodiments, the method comprises a second therapeutic agent, wherein the second therapeutic agent is selected from the group consisting of chemotherapeutics, anti-inflammatories, fatty acids, antibiotics, antivirals, small molecules, siRNA, and DNA. In some aspects, the second therapeutic agent is encapsulated by the outer compartment. In still other aspects, the second therapeutic agent is encapsulated by the inner compartment.

In other embodiments of the instant disclosure, the first material is poly(epsilon-caprolactone). In still other embodiments, the first material is hydrophilic. In some aspects, the first material is aqueous. In still other embodiments, the second material is hydrophobic. In some aspects, the second material is safflower oil.

In certain embodiments, the outer compartment is encapsulated within an exterior compartment. The exterior compartment can comprise an aqueous material. In some embodiments, a target-specific binding agent is attached to the surface of the outer compartment. In some aspects, the target-specific binding agent is selected from the group consisting of antibodies and binding fragments thereof and peptide sequences. In still another aspect, the target-specific binding agent is an EGFR-specific antibody. In yet another aspect, the target-specific binding agents bind to alpha-V-beta III integrin receptor.

In some embodiments, the first agent is a gene construct. In some embodiments, the methods further comprise expressing the gene construct in the target tissue or cell. In some aspects, the gene construct encodes IL-10. In other aspects, the gene construct causes apoptosis in the target tissue or cells. In still other aspects, the gene construct is siRNA. In preferred embodiments of the instant disclosure, the target cell is a macrophage.

Interleukin-10 (IL-10)-expressing plasmid DNA, were formulated with gelatin nanoparticles that were encapsulated in a PCL microsphere. The same delivery vehicle was used to orally administer systems disclosed herein to silencing the expression of tumor necrosis factor-α (TNF-α) in the treatment of inflammatory bowel disease. An illustration of NiMOS and scanning electron micrographs of siRNA encapsulating gelatin nanoparticles and microspheres is shown in FIG. 3A. Using a solvent displacement method, spherical gelatin nanoparticles, encapsulating siRNA with a mean diameter of 279.2±3.2 nm, were produced (see, e.g., Oster et al. *Journal of Controlled Release* (2006) 111(3): 371-381; Ribeiro et al. *Food Hydrocolloids* 22(1): 12-17). For additional protection from pH and enzymatic degradation during the gastrointestinal transit, the nanoparticles were further encapsulated in PCL microspheres to create NiMOS. These were of fairly uniform shape and size with a relatively smooth surface morphology, and diameters ranging from 2.4 µm to 3.2 µm for blank and siRNA encapsulating microparticles, respectively (FIG. 3C).

To ensure that siRNA was not affected during the manufacturing processes and that particles can efficiently protect this payload in the presence of degrading enzymes, the stability of extracted siRNA was evaluated by agarose gel electrophoresis. Encapsulation does not affect the structure or size of siRNA (FIG. 3B). For example, siRNA from gelatin nanoparticles (lane 5) and NiMOS (lanes 7, 8) had the same size as control siRNA (lane 2). Furthermore, protease addition had no adverse effect on siRNA (lane 3). Additionally, NiMOS appeared to have a protective effect on the payload. This was demonstrated by the band in lane 7; NiMOS were exposed to RNAse A followed by inactivation of the enzyme and extraction of the siRNA revealing a fragment with the same size as control counterparts. However, siRNA released from gelatin nanoparticles was completely degraded when exposed to protease and RNAse, (lanes 6, 9). Exposure of NiMOS to protease alone did not liberate siRNA (no band; lane 11). Quantification of encapsulated siRNA revealed a loading efficiency of 90.2±5.4% in gelatin nanoparticles. Final siRNA loading efficiency in NiMOS was measured to be 55.2±2.8% of the added siRNA.

3. Pharmaceutical Formulations

Toxicity and therapeutic efficacy of such compounds can be determined by standard pharmaceutical procedures in cell cultures or experimental animals, e.g., for determining the $LD_{50}$ (The Dose Lethal To 50% Of The Population) And The $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the methods described herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the disclosed systems and methods may be formulated in conventional manner using one or more physiologically acceptable carriers or excipients. Thus, the compounds and their physiologically acceptable salts and solvates may be formulated for administration by, for example, injection, inhalation or insulation (either through the mouth or the nose) or oral, buccal, parenteral or rectal administration.

For such therapy, the compounds can be formulated for a variety of loads of administration, including systemic and topical or localized administration. Techniques and formulations generally may be found in Remington's Pharmaceutical Sciences, Meade Publishing Co., Easton, Pa. For systemic administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ation oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Embodiments of the multicompartment systems disclosed herein can be designed for oral delivery to a subject. For example, the multicompartment delivery systems can comprise solid alginate and/or gelatin nanoparticles. The hydrophilic nanoparticles can be encapsulated in a microsphere comprising a hydrophobic material such as poly(epsilon-caprolactone) (PCL) or poly(D,L-lactide-co-glycolide) (PLGA). FIG. 3 shows scanning electron microscopy images of these multi-compartmental delivery systems.

Preparations for oral administration may be suitably formulated to give controlled release of the active compound. For buccal administration the compositions may take the form of tablets or lozenges formulated in conventional manner. For administration by inhalation, the compounds for use according to the present disclosure are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds can be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, oligomers can be formulated into ointments, salves, gels, or creams as generally known in the art. A wash solution can be used locally to treat an injury or inflammation to accelerate healing.

In clinical settings, the multicompartment delivery systems in the instant disclosure can be introduced into a patient by any of a number of methods, each of which is familiar in the art. For instance, the multicompartment delivery systems can be introduced systemically, e.g., by intravenous injection.

Enhanced protection of nucleic acid from extracellular and intracellular barriers is an issue. To address this issue, nucleic acid-encapsulated solid nanoparticles were designed that are further encased in the innermost water phase of the water-in-oil-in-water (W/O/W) multiple emulsion to develop nanoparticles-in-emulsion (NiE) multi-compartmental delivery system.

4. Macrophage-Targeted Delivery

The idea that macrophages behave as a Trojan horse vector comes from the knowledge that micro-organisms, such as bacteria and viruses, use monocytes and macrophages to proliferate and hide from immune-surveillance system. Particularly in the case of HIV-1 progression, there is mounting evidence depicting the role of macrophages in disease progression, pathogenesis, and latent reservoir formation. Like other retroviruses and lentiviruses, HIV-1 has the ability to infect and replicate in non-diving cells such as cells of monocyte/macrophage lineage; although CD4+ T-lymphocytes appear to be the primary target of HIV virus. The virus may affect the macrophages by influencing the cytokine production profile and this may result in chronic inflammation and extensive tissue damage. Interestingly, the infected macrophages appear to be resistant to the toxic effects of the virus and thus serve as a Trojan horse to the HIV virus.

The methods and systems described in the instant disclosure can be used for a variety of purposes including imaging, diagnostics, and treatment of conditions and diseases. Furthermore, the multicompartmental delivery systems can be utilized for gene therapy, gene silencing, cancer treatments, and vaccination. The systems and methods described herein can be targeted to any tissue or cell type. One such type of cell are macrophages.

Nanoparticle Systems for Macrophage-Targeted Delivery

With the advancement in the applications of nanotechnology for medical diagnosis and therapy over past two decades, the ability to modify the surface of the nanoparticles to enhance the specificity of the delivery system for a particular cell/tissue/organ has been developed to an extent that it can be exploited to practice the methods disclosed herein.

The over or under-activity of macrophages can result in the onset and/or progression of pathologic conditions, including, but not limited to, growth and spread of malignant tumors, sepsis, chronic inflammation in rheumatoid arthritis, lysosomal storage disease, atherosclerosis and major infections including HIV/AIDS and tuberculosis.

There are two approaches to targeting: passive or active targeting. Passive targeting refers to the accumulation of the drug or drug-carrier nanosystem by exploiting the pathophysiological condition and anatomical route. For example nanoparticle systems that are >100 nm are readily opsonized and removed from the circulation by reticuloendothelial system (RES) and degraded by the macrophages in the liver and spleen. Thus, the tendency of unmodified nanoparticles to localize in the RES has been exploited as a way to passively deliver the pay load to macrophages. Nanoparticles have been observed to passively accumulate at inflamed sites due to the enhanced permeation and retention (EPR) effect. The presence of macrophages at these sites presents an opportunity to passively target these cells.

The presence of macrophages at these sites has been successfully exploited for drug/gene delivery purposes (see, e.g., Griffiths et al. *Gene Therapy* (2000) 7: 255-262; Burke et al. *Journal of Leukocyte Biology* (2002) 72:417-428). Additionally, particle hydrophobicity, size, surface charge, and shape characteristics are also exploited to enhance macrophage specific delivery. For instance, highly hydrophobic nanoparticles, such as those made with polystyrene, are efficiently internalized in macrophages relative to hydrophilic nanoparticles.

Active targeting approaches are based on the surface modification of the systems with an agent (e.g., ligand, antibody, peptide) that has the selective affinity for recognizing and interacting with the particular cell type, tissue, or organ in the body. The phenomenon of active targeting can be achieved by utilizing the presence of various receptors and lipid components on the plasma membrane of cells. Macrophages are a preferred cell type for the systems disclosed herein. These receptors may be uniquely expressed on specific cells or may show a differentially higher expression on diseased cells in comparison to the normal cells. Table 1 below briefly describes some of the key properties of different receptors that are present on the surface of macrophages and can be utilized for actively targeting these cells. These different receptors can be down-regulated or upregulated using known gene therapy techniques. In addition, such receptors can be used as targets for multicompartment delivery systems. Such systems can have target-specific binding agents attached to the surface of the inner or outer compartment. The target-specific binding agents can be ligands for a receptor, peptidomimetic compounds that bind to a receptor, or small molecules capable of binding to a receptor.

TABLE 1

Examples of Receptor Systems Utilized for Targeting Macrophages

| Macrophage-Receptor Targeted | Brief Description |
|---|---|
| Mannose Receptor | C-Type lectin |
| | Involved in pathogen recognition |
| | Ligand binding to the receptor is dependent on $Ca^{2+}$ concentration |
| | Facilitates receptor-mediated endocytosis |
| Scavenger Receptor | Receptors bind a variety of poly-anionic macro-molecules and modified (acetylated) LDL |
| | Three classes of receptor are known, SR-A, B, and C |
| | Scavenger receptors are implicated in pathological deposition of cholesterol during atherogenesis |
| Dectin-1 Receptor | C-Type lectin. |
| | Unlike, other lectins, does not require $Ca^{2+}$ co-ordination for calcium binding. |
| | Involved in pattern recognition & phagocytosis of unopsonized β-glucan particles and soluble β-glucan (component of yeast cell wall). |
| Tuftsin peptide | Tetra-peptide sequence L-Thr-L-Lys-L-Pro-L-Arg (TKPR) |
| | Synthesized by the enzymatic processing of CH2 domain of the Fc fragment of the heavy chain of IgG molecule |
| | Activates Mφ and enhances their phagocytic ability |
| Hyaluronate | Ligand for CD44 receptor |
| | The receptor is a glycoprotein and is known to be involved in phagocytosis of large particles |

The multicompartment delivery systems are hydrophobic in certain embodiments. Since multiple emulsion globules are hydrophobic, they are readily internalized by intestinal macrophages upon oral administration through the Peyer's patch. Furthermore, when making these multicompartmental delivery systems, they can be generated in sizes that are preferentially taken up by macrophages. Once internalized by macrophages, these cells can travel and deliver the transfected protein in different parts of the body through systemic circulation. Alternatively, this method can also silence critical genes in activated macrophages and promote pro- or anti-inflammatory status as desired for effective disease treatment of disease. Also, uptake by macrophages and efficient intracellular delivery also provides an opportunity for vaccination using peptides, proteins, attenuated microorganisms as antigens as well as DNA- and RNA-based vaccines that will require transfection and production of the appropriate human and cellular immune responses.

Targeted Systems for Delivery of Small Molecule and Biological Therapeutics

The role of macrophage cells in various disorders such as HIV/AIDS, inflammation related disorders, cancer, and infectious diseases makes it a preferred pharmaceutical target. For example, macrophages are known to phagocytose and kill various microorganisms, but with the advancement in the field of molecular biology, it has been established that many of these pathogens have developed subtle means for residing in the macrophages by mainly avoiding phagocytosis or developing lysosomal tolerance.

The drugs available for such diseases suffer from the problem of side effects and solubility. Therefore, nanoparticle based drug delivery systems can improve the therapeutic index of such drugs by lowering the toxicity and enhancing the targeting ability to macrophages. See Table 2 for examples of nano-platform systems containing small molecule drugs for targeting macrophages.

TABLE 2

Examples of Small Molecule Therapeutics Encapsulated in Macrophage Targeted Nano Delivery Systems

| Formulation Type | Composition | Particle Size | Active Molecule | Disease Condition |
|---|---|---|---|---|
| Mannosylated solid lipid nanoparticles | | Not available | Rifabutin | Mycobacterium tuberculosis |
| Mannan-caoted gelatin particles | | 120 ± 12 nm | Didanosine | HIV/AIDS |
| O-Palmitoyl mannan-coated emulsions (nano sized lipid particles) | Trilaurin/ phosphatidylcholine | 0.32 ± 0.02 μm | Amphotericin B (AmB) | Visceral Leishmaniasis |
| Hexyl-cyanoacrylate nanoparticles | | 230 ± 20 nm | Azidothymidine | HIV/AIDS |
| Acetylated LDL microemulsions | DPPE/DPPC/Seal oil | 27-32 nm | Azidothymidine and pro-drug forms | HIV/AIDS |

In some embodiments disclosed herein, macrophages that have taken up the multicompartmental delivery vehicles of the disclosed herein can be used to carry the payload delivered by said vehicle to a target site within the body, such as a tumor or site of inflammation. The payload can be a therapeutic treatment, such as, but not limited to, anti-inflammatory therapeutics, including, but not limited to steroids, small molecule drugs (i.e. bisphosphonates), fatty acids, and antioxidants, as well as chemotherapy, antibiotics, peptides, vaccines, small molecules, proteins, and antibody therapeutics. The present methodologies can also treat a range of anti-inflammatory diseases or conditions. By "inflammatory disease" or "inflammatory condition" as used herein is meant any disease, condition, trait, genotype or phenotype characterized by an inflammatory or allergic process as is known in the art, such as inflammation, acute inflammation, chronic inflammation, respiratory disease, atherosclerosis, restenosis, asthma, allergic rhinitis, atopic dermatitis, septic shock, rheumatoid arthritis, inflammatory bowl disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses, and any other inflammatory disease, condition, trait, genotype or phenotype that can respond to the modulation of disease related gene expression in a cell or tissue, alone or in combination with other therapies. In yet other embodiments, the multicompartmental delivery systems disclosed herein are used to deliver a payload of a therapeutic treatment to a target cell, wherein the small molecule drug induces apoptosis in the target cell.

Biological therapies such as therapeutic gene delivery or gene silencing can be designed to target and exploit macrophages. In some embodiments, the therapeutic gene can be transferred into the cells, which are then used as "guided missiles."

Macrophages are capable of secreting various biological products (see Table 3 below). Depending on the products being secreted, if the process is left unchecked, this can result in tissue damage and fibrosis, which are characteristic of chronic inflammation. As the macrophage is capable of a number of processes in addition to secreting various biomolecules, it is an ideal target for gene therapy for treatment of a variety of diseases and conditions, including, but not limited to, inflammation, cancer, Crohn's disease, inflammatory bowel disease, and atherosclerosis.

TABLE 3

Select Functions and Secreted Bio-Molecules from Activated Macrophages

Microbicidal Activity
Tumoricidal Activity
Chemotaxis
Phagocytosis/Pinocytosis
Glucose Transport and Metabolism
Generation of Gaseous Mediators Reactive nitrogen intermediates (e.g., NO)
Reactive oxygen intermediates
Enzymes Neutral proteases, elastase, lysozyme, acid hydrolases, collagenases, plasminogen activator, arginase, lipases, phosphatases
1α-hydroxylase
Plasma Proteins Complement components (C1-C5, properdin)
Coagulation factors (factors V, VIII, tissue factor)
Fibronectin
Cytokines and Chemokines IL-1, IL-6, IL-10, IL-12, IL-15, IL-18, TNF- α, INF- α, TGF-β, GM-CSF, M-CSF, G-CSF
IL-8, MCP-1, MIP-1 α/β regulated on activation normal T expressed and secreted
Growth Factors Platelet-derived growth factor, endothelial growth factor, fibroblast growth factor
Lipid Mediators Eicosanoids The targets enumerated in Table 3 can be either up or downregulated depending on the desired result. For example, increasing expression of anti-inflammatory cytokines can be accomplished by delivering a gene construct to the cell using the multicompartmental delivery systems disclosed in the instant application. This would result in a reduction of the inflammatory response of the macrophages. In a particular embodiment of the instant disclosure, the anti-inflammatory cytokine to be upregulated is IL-10.

To reduce the expression of a secreted biomolecule, siRNA can be administered to the cell using the multicompartmental delivery systems disclosed in the instant application. In another embodiment of the instant disclosure, the inflammatory cytokine to be downregulated or silenced is TNF-α.

Macrophage-Targeted Nano-Systems for Imaging

The arrangement and spacing of atoms at scale of nanometer imparts unique physical and chemical properties to the material. Particles such as colloidal gold, iron-oxide crystals, and quantum dots are some of the examples of inorganic nanoparticles that are in the size range of 1-30 nm. Methods of making such nanoparticles are known in the art (see, e.g., Luna Martinez et al. *Mater. Sci. Forum: Adv. Elec. Microscop. Nanomat.* (2010) 644: 51-55; Gardea-Torresdey et al. *Journal of Nanoparticle Research* (1999) 1(3): 397-404; Zhou et al. *Chem. Mater.* (1999) 11 (9): 2310-2312). These particles have been explored for their ability to act as imaging/contrast enhancing agents for multi-modality non-invasive imaging techniques such as magnetic resonance imaging (MRI), positron emission tomography (PET), and computed tomography (CT). Also, besides the small particle size, long blood circulation half-lives and opportunity for surface modification allows to improvements in signal intensity and specificity, making them very attractive diagnostic or contrast enhancing agents.

Macrophages are suitable imaging targets in diseases such as inflammation, atherosclerosis, and rheumatoid arthritis. This is because these cells are present in abundance and also are involved in multiple functions leading to inflammation and angiogenesis. Therefore, monitoring their role in such conditions can provide valuable insight into the progression of a disease.

Nanoparticles designed to target macrophage cells have the potential to improve the detection and characterization of the human aortic atherosclerosis. Specific examples where the efficacy of the nanoparticles as contrast agents and targeting macrophages has been demonstrated in an in vivo animal model will be discussed in the examples of the instant disclosure. Table 4 below considers select examples of nano-platform systems, containing suitable imaging agents, that have been used to target macrophages and demonstrated the advantage of such systems in the treatment of atherosclerosis and rheumatoid arthritis disease models.

TABLE 4

Nanoparticle Systems Targeting Macrophages in Atherosclerosis and Rheumatoid Arthritis

| Nanoparticle System | Particle Size | Disease State |
|---|---|---|
| Crystalline ethyl-3,5bis(acetylamino)-2,4,6-triiodobenzoate iodinated particles dispersed in surfactant for stabilization. | 259 nm | Atherosclerosis |
| Dextranated and DTPA modified magnetofluorescent labeled with $^{64}$Cu. | 20 nm | Atherosclerosis |
| POPC, DPPE-NBD, DPPE-Biotin, Gd-DOTA-BSA. | 125 nm, 89 ± 13 nm and 107.3 ± 0.21 nm | Atherosclerosis |
| Self-assembled gold coated iron oxide NPs stabilized with dextran | ~30 nm | Atherosclerosis |
| Silica NPs containing a luminescent [Ru(bpy)$_3$]Cl$_2$ core and a paramagnetic monolayer coating of a silylated Gd complex. | 37 nm | Rheumatoid arthritis |
| Ultra-Small Iron Oxide NP | ~30 nm | Antigen-induced arthritis |

POPC = [palmitoyl-oleoyl phosphatidylcholine], DPPE-NBD = [1,2-dipalmitoyl-sn-glycero-3-phosphoethanolamine-N-7-nitro-2-1,3-benzoxadiazol-4-yl, DPPE-Biotin = [1,2-dipalmitoyl-sn- glycero-3-phosphoethanolamine-N-Biotinyl], bpy = [2,2'-bypyridine].

Delivery of Biological Therapeutics

The classical activation state is characterized by killing of intracellular pathogens and tumor resistance and can be induced by interferon-γ (IFN-γ) alone or in conjunction with microbial products such as lipo-polysaccharide (LPS) or cytokine such as tumor-necrosis factor alpha (TNF-α). Activation of macrophage via the classical pathway is marked by high antigen presentation capacity, high IL-12, IL-23, nitric oxide (NO), and reactive oxygen species production.

Figure 4:
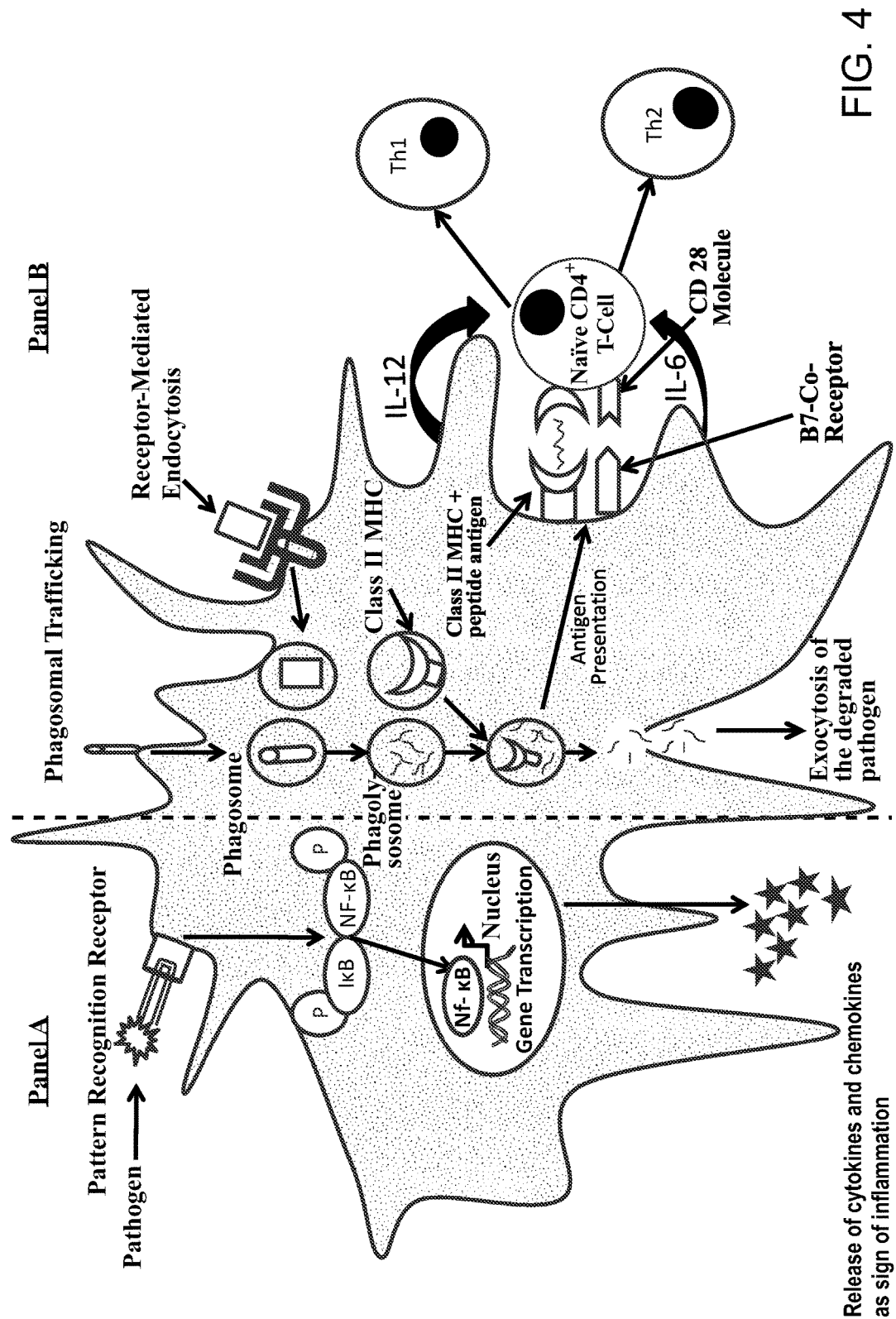
FIG. 4: The diagram above depicts the key functions of a macrophage cell. Panel A shows the ability of macrophages to detect the presence of bacteria (pathogen) via specific receptors (pathogen recognition receptors or toll like receptors (TLR)) on its surface, which leads to a cascade of the down-stream signals that ultimately lead to release of cytokines and chemokines to signal other cells about bacterial invasion. Panel B highlights the ability of these cells to phagocytose, either via non-specific or receptor-mediated endocytosis, and degrades the bacteria as seen in the phagolysosomal compartment. The degraded bacterial fragments can be excreted out of the cell via process called exocytosis. Also, the degraded antigenic peptide products can be displayed at the cell surface with the help of class II MHC molecule. This process helps in communicating with the T-helper cells. However, naïve T cell requires a secondary signal for activation, which is provided by interactions between B7 receptor on macrophages and CD28 ligand molecule on T-cell. Upon activation, these cells can further lead to generation of Th1 and Th2 immune response. In addition, macrophages are also capable of releasing cytokines such as IL-6, 12 that can influence adaptive immune response. NF-κB-Nuclear Factor-κB, IκBInhibitor of NF-κB, IL-6-Interleukin-6, IL-12-Interleukin-12.

The alternative state can be induced by cytokines such as IL-4 and IL-13 and mainly results in anti-inflammatory responses and resolution of injury. Furthermore, the alternate activation stage is characterized by an increase in the IL-10 and IL-1ra cytokines, mannose and scavenger receptors, arginase production and decrease in the production of inducible nitric oxide synthase enzyme. FIG. 4 below highlights the central role played by macrophages in mediating innate as well as adaptive immune response.

The expression of inflammatory cytokines, including but not limited to, tumor necrosis factor (TNF-α), can be down-regulated/silenced using the siRNA (small interfering RNA) approach. Other embodiments of the systems and methods disclosed herein include treating inflammation by delivering plasmid gene encoding for anti-inflammatory cytokine protein such as IL-10 to macrophages, and comparing it to the silencing effect of TNF-α.

Table 5 describes some of the inflammatory mediators that are secreted by macrophages. Depending on the desired effect, the methods described herein can be used to modify the expression of any one of these mediators in order to control a disease state.

TABLE 5

Inflammatory mediators secreted by macrophages

| |
|---|
| LTB$_4$, LTC$_4$, LTD$_4$, 5-hydroxyeicosatetraenoic acid and thromboxanes |
| Platelet-activating factor |
| Platelet-derived growth factor (PDGF) |
| PGE$_2$, PGF$_2$ and PGD$_2$ |
| Histamine |
| Macrophage-derived mucous secretagogues (MMS-68) |
| Proinflammatory cytokines: IL-1, TNF-α, IL-6, IL-8 |
| Chemokines: MIP1α, RANTES, MIP1β, MCP-1, MCP-3 |

TABLE 5-continued

Inflammatory mediators secreted by macrophages

Immunoregulatory cytokines: IL-10, IL-12, IL-16 (lymphocyte chemoattractant factor), GM-CSF
Nitric oxide (NO), endothelins, superoxide anions, b-glucuronidase and neutral proteases GM-CSF, granulocyte macrophage colony-stimulating factor; IL, interleukin; LTB$_4$, leukotriene B$_4$; LTC$_4$, leukotriene C$_4$; LTD$_4$, leukotriene D$_4$; MCP, monocyte chemotatic protein; MIP, macrophage inflammatory protein; PGD$_2$, prostaglandin D$_2$; PGE$_2$, prostaglandin E$_2$; PGF$_2$, prostaglandin F$_2$; RANTES, regulated on activation normal T cell expressed and secreted; TNF-α, tumor necrosis factor α.

IL-10 is produced by T cells, B cells, antigen presenting cells, mast cells and granulocytes amongst which macrophages are the major producers of IL-10. IL-10 plays a significant role in immune regulation by its action on different cell types (See Table 6). When exposed to IL-10, monocytes and macrophages synthesize and release soluble immune mediators which bring about resolution of inflammation and help in tissue repair. These mediators include IL-1RA and soluble TNF-α receptor. Additionally, IL-10 inhibits the release of anti-inflammatory cytokines including IL-1β, IL-6, G-CSF, GM-CSF and TNFα.

Inflammation recruits macrophages that increase inflammation and can eventually cause tissue destruction. The instant disclosure describes methods of modulating inflammation in order to stop the inflammatory cascade, enabling control and resolution of inflammation. For example, in a particular embodiment, the anti-inflammatory cytokine IL-10 is delivered to a macrophage using the disclosed multicompartment delivery vehicle. Once within the macrophage, IL-10 is expressed by the cell, thereby reducing the inflammatory response caused by the macrophage. In other embodiments, siRNA is delivered to a macrophage in order to stop the expression of inflammatory proteins secreted by the macrophage. A summary of the effects of IL-10 on different immune cell types appears in Table 6.

TABLE 6

Effect of IL-10 on different immune cell types.

| Cell Population | Suppression | Induction |
|---|---|---|
| Langerhans cells | Antigen presentation | |
| Dermal dendritic cells | CD86 expression, antigen presentation | |
| Monocytes/ macrophages | TNF-α, IL-1, IL-6, IL-8, IL-12 production, expression of MHC class II, CD86, CD54, CD40, antigen presentation | IL-1RA production, Soluble TNF receptor production |
| Eosinophils | IL-8, GM-CSF liberation | |
| Neutrophils | TNF-α, IL-1, IL-8 production | IL-1RA production |
| Mast cells | TNF-α production | Growth, Antigen-induced histamine liberation |
| T Cells | IL-2, and IFN-γ production, mitogen-induced proliferation | |
| NK cells | | Cytotoxicity |
| B cells | | Growth, IgE synthesis |
| Keratinocytes | Growth, IL-6 secretion capacity (?) | |
| Endothelial cells | | E-selectin expression |

In another embodiment, an IL-10 gene construct is administered utilizing the multicompartment delivery system disclosed herein. Once the multicompartment delivery system has been administered, it is allowed to selectively bind to a target tissue or a cell where it delivers its payload into the cell. Certain embodiments further comprise encapsulating the IL-10 gene construct in a nanoparticle. In some aspects the nanoparticle is designed to target an organelle within the cell. In certain aspects the organelle is the nucleus. In other embodiments, the multicompartment delivery system is comprises a second agent selected from the group consisting of a diagnostic, imaging, or therapeutic agent.

Gene Therapy Strategies

Gene therapy involves the delivery of genes to specific cells of the body where the gene encoding a protein is expressed. The resulting high concentrations of the desired protein should result in the treatment or prevention of a disease. Initially gene therapy was restricted only to genetic diseases where an abnormal or missing gene was delivered to replenish function of the missing gene. However, gene therapy can also be used for treatment of non-genetic diseases by supplementing genes encoding proteins capable of modulating cellular function.

Different approaches for delivery of genes into cells followed by expression of therapeutic protein are delivery of genes through direct injection in to target tissue, gene delivery through viral vectors and gene delivery through non-viral vectors.

The compositions and methods disclosed herein can be used to perform gene therapy on diseased tissues and cells. By "gene", or "target gene", is meant a nucleic acid that encodes an RNA, for example, nucleic acid sequences including, but not limited to, structural genes encoding a polypeptide. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, Science, 300, 258-260.

Synthesis of nucleic acids greater than 100 nucleotides in length is difficult using automated methods, and the therapeutic cost of such molecules is prohibitive. In this invention, small nucleic acid motifs ("small" refers to nucleic acid motifs no more than 100 nucleotides in length, no more than 80 nucleotides in length, and no more than 50 nucleotides in length; e.g., individual siNA oligonucleotide sequences or siNA sequences synthesized in tandem) are preferably used for exogenous delivery. The simple structure of these molecules increases the ability of the nucleic acid to invade targeted regions of protein and/or RNA structure. Exemplary molecules of the instant invention are chemically synthesized, and others can similarly be synthesized.

Oligonucleotides (e.g., certain modified oligonucleotides or portions of oligonucleotides lacking ribonucleotides) are synthesized using protocols known in the art, for example as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. All of these references are incorporated herein by reference.

The synthesis of oligonucleotides makes use of common nucleic acid protecting and coupling groups, such as dimethoxytrityl at the 5'-end, and phosphoramidites at the 3'-end.

In a non-limiting example, small scale syntheses are conducted on a 394 Applied Biosystems, Inc. synthesizer using a 0.2 mu.mol scale protocol with a 2.5 min coupling step for 2'-O-methylated nucleotides and a 45 second coupling step for 2'-deoxy nucleotides or 2'-deoxy-2'-fluoro nucleotides. Alternatively, syntheses at the 0.2 mu.mol scale can be performed on a 96-well plate synthesizer, such as the instrument produced by Protogene (Palo Alto, Calif.) with minimal modification to the cycle. A 33-fold excess (60 mu.L of 0.11 M=6.6 mu.mol) of 2'-O-methyl phosphoramidite and a 105-fold excess of S-ethyl tetrazole (60 mu.L of 0.25 M=15 mu.mol) can be used in each coupling cycle of 2'-O-methyl residues relative to polymer-bound 5'-hydroxyl. A 22-fold excess (40 mu.L of 0.11 M=4.4 mu.mol) of deoxy phosphoramidite and a 70-fold excess of S-ethyl tetrazole (40 mu.L of 0.25 M=10 mu.mol) can be used in each coupling cycle of deoxy residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); and oxidation solution is 16.9 mM I.sub.2, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-benzodithiol-3-one 1,1-dioxide, 0.05 M in acetonitrile) is used.

The method of synthesis used for RNA including certain siNA molecules of the invention follows the procedure as described in Usman et al., 1987, J. Am. Chem. Soc., 109, 7845; Scaringe et al., 1990, Nucleic Acids Res., 18, 5433; and Wincott et al., 1995, Nucleic Acids Res. 23, 2677-2684 Wincott et al., 1997, Methods Mol. Bio., 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 mu.mol scale protocol with a 7.5 min coupling step for alkylsilyl protected nucleotides and a 2.5 min coupling step for 2'-O-methylated nucleotides.

Alternatively, syntheses at the 0.2 mu.mol scale can be done on a 96-well plate synthesizer, such as the instrument produced by Protogene (Palo Alto, Calif.) with minimal modification to the cycle. A 33-fold excess (60 mu.L of 0.11 M=6.6 mu.mol) of 2'-O-methyl phosphoramidite and a 75-fold excess of S-ethyl tetrazole (60 mu.L of 0.25 M=15 mu.mol) can be used in each coupling cycle of 2'-O-methyl residues relative to polymer-bound 5'-hydroxyl. A 66-fold excess (120 mu.L of 0.11 M=13.2 mu.mol) of alkylsilyl (ribo) protected phosphoramidite and a 150-fold excess of S-ethyl tetrazole (120 mu.L of 0.25 M=30 mu.mol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5-99%. Other oligonucleotide synthesis reagents for the 394 Applied Biosystems, Inc. synthesizer include the following: detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM I.sub.2, 49 mM pyridine, 9% water in THF (PerSeptive Biosystems, Inc.). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Various cytokine targeted protein and gene therapies have been explored in recent past. Antagonists of pro-inflammatory cytokines such as soluble TNF receptor molecule, IFN-γR-IgG fusion molecules and IL-12 receptor antagonist have been found useful in normalizing inflammatory response. Protein therapies, such as soluble TNF-receptor (etanercept), anti-TNF antibody (infliximab), IL-1 receptor antagonist (IL-1Ra), were found to be efficacious but these required repeated high dose injections/infusions because of very short protein half life. Another limitation of protein therapy is due to the high systemic concentration of the protein therapeutic after injection. This may lead to undesired side effects of the therapeutic protein molecule at sites other than the target site in the body. These limitations can be overcome if genes encoding therapeutic protein are expressed in target cells leading to levels of protein which are high in the target tissue when compared to levels of protein in systemic circulation.

The present disclosed multicompartment delivery systems improve specificity of gene therapy approaches. Due to the higher specificity of targeted gene therapy, the methods disclosed herein lead to reduced systemic side effects. Furthermore, repeated administration of therapeutic proteins is not necessary when gene therapy is used since a single copy of plasmid DNA delivered inside a cell can undergo multiple expression cycles over a prolonged period of time. This allows for reduced dosing frequency.

Effective gene delivery systems would protect DNA from degradation and prevent their clearance by reticular endothelial systems. Furthermore, the gene delivery system should release its payload into the cytosol by endosomal escape, should facilitate nuclear entry of DNA and bring about high levels of gene transfection for a prolonged period of time.

The multicompartment systems disclosed herein can comprise polymers. In certain embodiments, the polymers can be chemically modified. For instance, chemical modification of cationic polymers can be carried out. In the case of poly(L-lysine), aggregation of positively charged particles can be reduced by increasing aqueous solubility of poly(L-lysine). This can be achieved by attachment of dextran to the epsilon amino groups of poly(L-lysine). In the case of PEI, aqueous solubility can be increased by covalent coupling of PEG with amino groups of PEI. Also it was found that modification of poly(L-lysine) with PEG can reduce its cytotoxic effect on cells in culture.

In certain embodiments, non-condensing polymers are capable of encapsulating DNA by non-electrostatic interaction. These polymers posses either a neutral charge or a slight negative charge, which helps protect DNA from exogenous nucleases. Absence of positive charge prevents electrostatic interactions between polymer and negatively charged DNA, making DNA encapsulation more feasible. Also, since the DNA is encapsulated within polymeric matrix, repulsion between the DNA payload and the cell membrane which may prevent endocytosis is restricted. Moreover, absence of positive charge limits recognition of non-condensing polymeric delivery vehicle by the mononuclear phagocyte system and hence limits early clearance of the delivery vehicle. In addition, non-cationic charge on polymer also avoids possibility of activation of innate immune system by mononuclear phagocyte system causing acute inflammatory response.

DNA encapsulating polymers like PEG, poly(ethylene oxide) (PEO), poly(D,L-lactide-co-glicolide) (PLGA), poloxamer block copolymers, gelatin and cellulose derivatives have been studied previously and have shown noticeable gene transfection efficiency in various studies. PEG and PEO bring about DNA encapsulation by means of hydrogen bonds between nucleotide bases and phosphate groups of DNA and molecules of polymeric matrix. Poloxamers (Pluronics®) which are PEO-based copolymers have also been used for DNA encapsulation.

Type B gelatin-based nanoparticle vector for gene transfection has shown efficient systemic and local delivery, intracellular trafficking, and expression in various local and systemic studies (see, e.g., Magadala et al. *AAPS J.* (2008) 10(4): 565-576). Nanoparticles formulated from Type B gelatin have several advantages like biocompatibility, biodegradability, high DNA loading capacity, high gene transfection efficiency, high cellular uptake by non specific or receptor mediated endocytosis. Type B gelatin, which is obtained by alkaline hydrolysis, has an isoelectric point between 4.8 and 5. At neutral pH Type B gelatin has net negative charge on its surface hence type B gelatin and DNA interact in a charge independent manner and DNA gets physically entrapped in hydrogel like matrix of gelatin biopolymer. These properties of gelatin make it a polymer of choice for its use as an efficient and safe non-viral gene transfection vector.

Nanoparticles-in-Emulsion (NiE) Formulations

One of the biggest challenges facing the drug delivery industry today is the delivery of biological molecules such as peptides, proteins and nucleic acid based biological molecules through oral administration. Oral administration of a drug has advantages such as ease of administration, ease of dosage regulation and frequency, and reduction in overall cost of therapy. For successful oral delivery of bio-molecules like nucleic acids, delivery vehicles should be designed such that they can provide protection to the encapsulated payload from physiological environment of GI tract until they release the payload at the absorbing mucosal membrane of GI tract for cellular uptake of bio-molecule to show its therapeutic action.

For gene therapy of local and systemic diseases, successful gene transfection in the GI tract can not only bring about production of encoded protein at the local site of transfection, but can also bring about release of synthesized protein in systemic circulation. The GI tract can also be utilized as a target for the delivery of DNA vaccines, where encoded protein antigen can bring about the development of local and systemic immune responses. Although successful controlled release of small molecules like therapeutic proteins and peptide antigens through water in oil in water multiple emulsion in the intestine has been reported by several research groups, there have been only few studies confirming efficient gene delivery and transfection by utilization of multiple emulsion system as a gene delivery vehicle.

Although proven successful for protein delivery, in case of gene delivery, enhanced protection for DNA is essential because DNA needs to be protected not only from intestinal nucleases, but must also reach the nucleus of the target cell in order to bring about effective gene transfection. To address this issue, DNA can be provided with additional protection by encapsulation within nanoparticles, which can be then encapsulated in the innermost aqueous phase of a multiple emulsion. In this manner, a multi-compartmental DNA delivery vehicle can be formulated which can provide enhanced protection and controlled release property to encapsulated gene. Multiple emulsion globules containing plasmid encapsulated nano-particles can release their payload either before its uptake by M cells of Peyer's patches in small intestine or after their engulfment by phagocytic cells present within Peyer's patches. Since multiple emulsion globules are hydrophobic, they are readily internalized by intestinal macrophages, as well as other cell types. Once internalized by macrophages, these cells can travel and deliver the protein in different parts of the body through systemic circulation.

The delivery systems of described herein involve the encapsulation of DNA within nanoparticles, allowing for the loading of a larger DNA payload in the emulsion system. This is because the DNA is protected within the nanoparticles and thus can withstand the high shear homogenization steps that occur during the process of preparing a multiple emulsion. Based on results obtained from gene transfection studies using gelatin nano-particles, it was believed that if these nanoparticles can be provided with further protection by their encapsulation in the innermost phase of water-in-oil-in-water (W/O/W) multiple emulsion system, controlled and enhanced gene delivery and transfection could be achieved both in vitro and in vivo.

The disclosure is further illustrated by the following examples. The examples are provided for illustrative purposes only. They are not to be construed as limiting the scope or content of the disclosure in any way.

Other Methods of Use of Multicompartment Delivery Systems

Cancer Therapy

Cancer is defined as the rapid and uncontrolled progression of cell growth. Tumor cells achieve this growth by undergoing an array of processes such as angiogenesis, metastases, and immunosuppression. Tumor-associated macrophages (TAM) seem to play a prominent role in tumor survival by helping the tumor to carry out abovementioned processes.

The proof of close association between an abundance of TAMs and poor prognosis in breast, prostate, colon, and cervical cancer has already been established. In a typical scenario a tumor secretes various chemo-attractants such as colony-stimulating factor-1 (CSF-1), chemokines (CCL2, 3, 4, 5, and 8), and vascular endothelial growth factor (VEGF). As a result, monocytes in the blood stream are attracted to the tumor tissue where they differentiate and take up the role of the resident macrophages. Additionally, in comparison to macrophages derived from healthy tissues, these cells seem to have a distinct phenotype.

Figure 5:
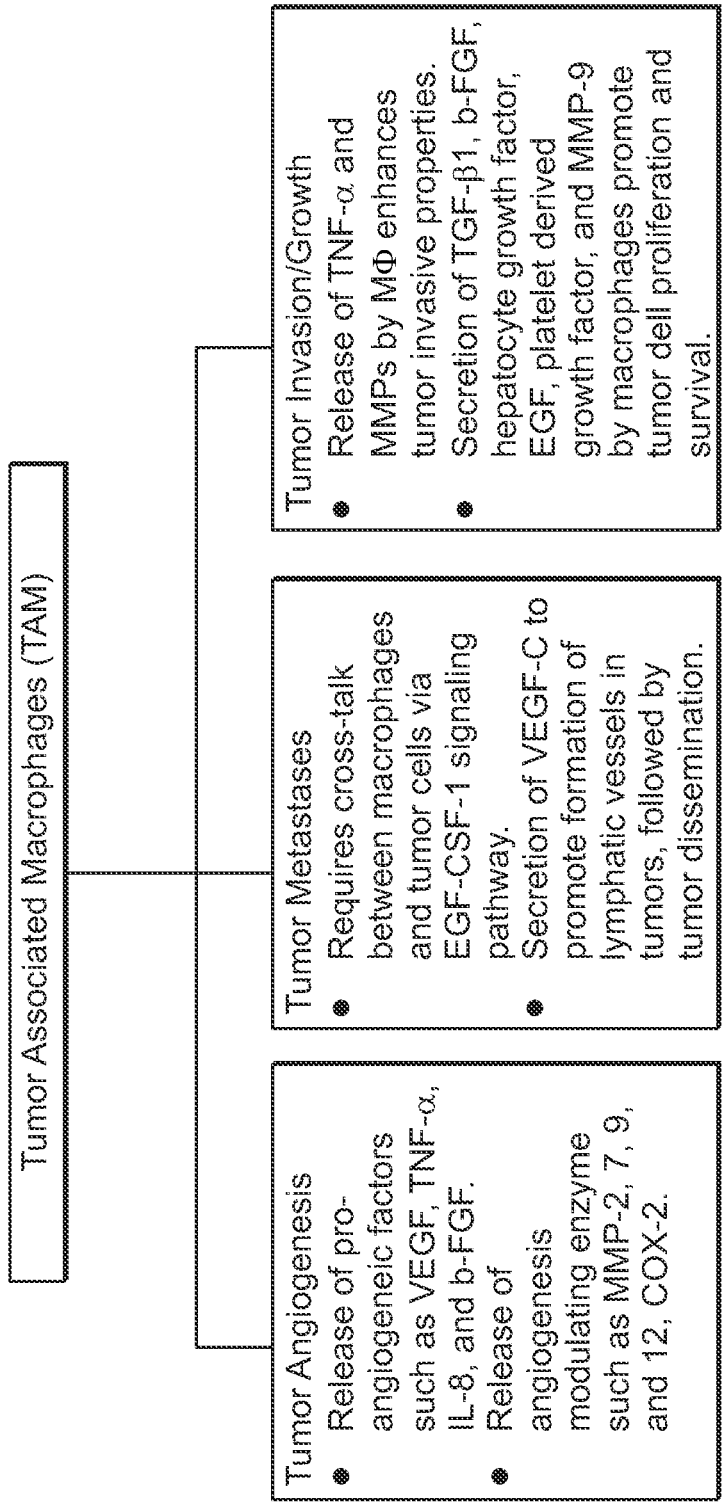
FIG. 5: Different functions of tumor associated macrophages in promoting tumor growth and metastases.

TAMs are characterized by low expression of the differentiation-associated macrophage antigens, carboxypeptidase M and CD51, high constitutive expression of interleukin (IL-1) and IL-6, and low-expression of TNF-α. It is believed that tumor-derived cytokines, chemokines, and proteases such as IL-4, 6, 10, TGF-β1, and PGE2 act on macrophages so that they develop into polarized type II or M2 macrophages. As a result, unlike in healthy tissue, the anti-tumor activity of the macrophages is compromised in the tumor micro-environment. Additionally, it has also been reported that hypoxia in the tumor microenvironment can also contribute to reduce the cytotoxic activity of TAM towards tumor cells by promoting the secretion of PGE2 and IL-10. Thus, it appears that upon differentiation, resident macrophages are trained or molded by tumor cells to perform specific functions. The role of TAMs in the above-mentioned processes is summarized in FIG. 5.

It is known in the art that metastatic tumor growth is inhibited if TAMs are killed. It has been shown that even in aggressive and/or metastatic cancers, tumor growth and disease progression is dramatically slowed. The systems and methods described herein enable specific targeting of these macrophages and can be used for effective delivery of apoptotic agents to the these cells. Furthermore, other agents can be included in the multisystem delivery vehicle to allow simultaneous imaging of the tumor(s), thereby allowing monitoring of the disease while simultaneously treating the disease.

As described earlier in the instant disclosure, the systems and methods disclosed herein provide for targeting macrophages. This allows the administration of therapeutics, such as chemotherapy or radioactive molecules for localized radiation therapy. Furthermore, the instant disclosure enables one of skill in the art to administer gene therapy using the multicompartmental delivery systems described herein. Gene constructs can be used to retrain TAMs to attack tumor cells, up or downregulate various biomolecule secretions on the part of the macrophage, as well as to delivery payloads to a tumor site. These aspects have been described throughout this disclosure.

Nanoparticle distribution within the body is based on various parameters, such as their relatively small size resulting in longer circulation times and their ability to take advantage of tumor characteristics.

EXAMPLES

Example 1

Formulation and Use of W/O/W Systems

W/O/W multiple emulsions are triphasic systems composed of three phases, inner aqueous droplets contained in oil globules surrounded by outer aqueous phase. The W/O/W multiple emulsion was formulated by a two step emulsification. Safflower oil (Jedwards, Inc., Quincy, Mass.), which is rich in omega-3 and omega-6 polyunsaturated fatty acids, was used for the oil phase of the emulsion. Safflower oil contains high levels of tocopherols, which are reported to have a negative effect on levels of pro-inflammatory cytokines tumor necrosis factor alpha and interleukin 1-beta. Tocopherols have shown to exert antioxidant activity and may provide protection against acute inflammation mediated by reactive oxygen species (10). The first step consisted of formulation of W/O primary emulsion using an oil soluble surfactant Span® 80. Naked plasmid (ME) or plasmid encapsulated in the gelatin nanoparticles (NiE) was incorporated in the aqueous phase of the primary emulsion to give the final concentration of 50 µg/ml of the multiple emulsion. A stable primary W/O emulsion with encapsulated naked plasmid DNA or as dispersion with DNA-encapsulated nanoparticles was formed using the Silverson homogenizer L4RT at the speed of 9,000 rpm for 15 minutes. The primary emulsion of dispersion was mixed with additional aqueous phase consisting of a water soluble surfactant Tween® 80 and the formulation was prepared by homogenization at 4,000 rpm for 4 minutes. Increasing the speed to greater than 4,000 rpm during this step resulted in rupture of the multiple emulsion globules.

Approximately 200,000 cells were plated in each well of a six-well plate containing alcohol-sterilized glass cover slip and allowed to adhere for 12 hours prior to treatment with control and test formulations. The cells were fed with multiple emulsions containing 0.0025% (w/v) rhodamine-dextran either solubilized in the inner aqueous phase or encapsulated in gelatin particles which were then added to the internal aqueous phase of W/O/W emulsion. Multiple emulsions prepared with blank aqueous phase or with blank gelatin nanoparticles were used as controls. After 60 minutes, 90 minutes, and 120 minutes following incubation with the control and test formulations, the cells were washed with sterile phosphate buffered saline (PBS, pH 7.4) and the cover slip was removed from the wells and mounted on a clean glass slide.

The microscopy images in FIG. 1 (top) shows that that the rhodamine-dextran containing W/O/W emulsion and NiE formulations were rapidly internalized in murine alveolar macrophages J774A.1 cells. As time progressed, an increase in fluorescence intensity was observed, which became maximum after 120 minutes of exposure. In addition, the microscopy images in FIG. 1 (bottom) shows that maximum gene transfection was observed in cells treated with NiE formulations followed by ME and GNP formulations. Maximum green fluorescence was observed in cells treated with NiE formulation starting 24 hour post treatment with sustained levels at day 2, 3 and 4 followed by a decline at day 5 and 6. These results indicate that NiE formulation was better compared to ME or GNP formulations in causing gene transfection since NiE formulation offer more protection to plasmid DNA during formulation resulting in higher loading efficiency of plasmid DNA per ml of formulation as well as during intracellular transport of plasmid DNA in endosomal/lysozomal compartments.

Example 2

Tuftsin-Modified Alginate Nanoparticles as a Non-Condensing Macrophage-Targeted Summary Macrophage-targeted tuftsin-modified cross-linked alginate nanoparticles were developed for local and systemic anti-inflammatory gene therapy. Plasmid DNA expressing both enhanced green fluorescent protein (GFP) and interleukin-10 (IL-10) were physically encapsulated in the non-condensing alginate matrix. Alginate nanoparticles could efficiently encapsulate the plasmid and protect against DNAse degradation. Furthermore, the tuftsin-modified nanoparticles were efficiently internalized in J774A. 1 macrophage cells with saturation within 1 hour of incubation. Both quantitative and qualitative analysis of transgene expression with GFP-and IL-10-expressing plasmid DNA showed that the tuftsin-modified nanoparticles had significantly greater efficiency than any of the other systems, including scrambled peptide-modified nanoparticles and Lipofectin®, a cationic lipid-based transfection reagent.

Introduction

Local production of the therapeutic protein using transgene expression affords greater control over therapy with fewer side effects than repeated systemic administration of proteins, like antibodies. Although viral and non-viral gene delivery systems have been investigated for anti-inflammatory gene therapy, the challenge has been to develop safe and effective system so that this experimental strategy can be translated into a clinical-viable therapeutic approach.

Herein is described the development of a novel, safe and effective non-viral gene delivery system for IL-10-expressing plasmid DNA and transfection for local and systemic anti-inflammatory therapy. The clinical significance of IL-10 applies in inflammation related diseases including, but not limited to, inflammatory bowel disease, atherosclerosis, and rheumatoid arthritis. The expression of IL-10 in macrophages would result in termination or at least a significant reduction of the inflammatory response associated in such disease models.

Unlike cationic lipids and polymers that form electrostatic complexes with negatively-charged DNA, an alginate carrier was selected as a biocompatible non-condensing polymer for preparation of nanoparticles and the surface was modified with tuftsin for macrophage-selective uptake.

Gene Delivery System for Anti-Inflammatory Therapy

Figure 6:
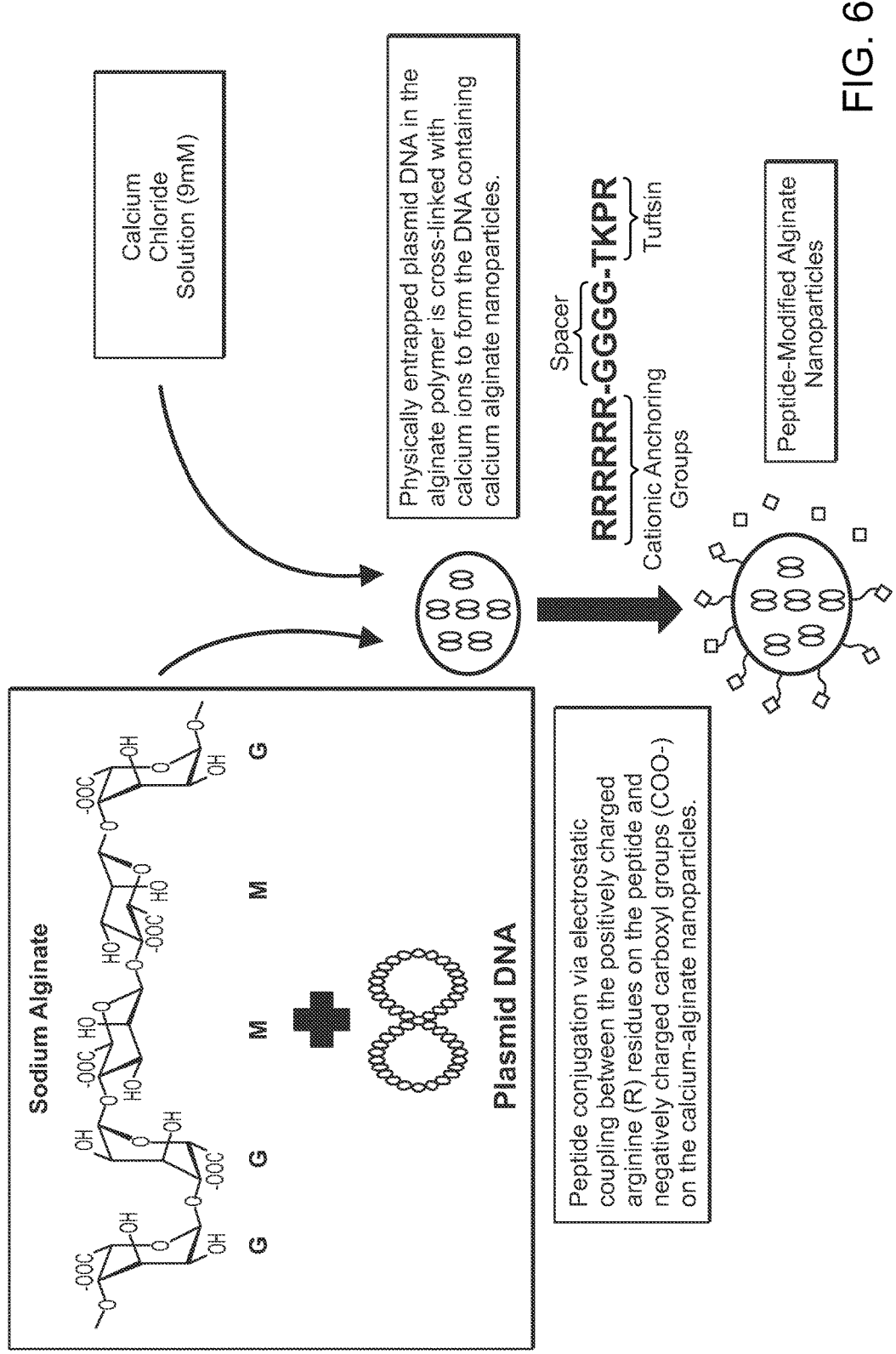
FIG. 6: Schematic illustration for the preparation of tuftsin-modified macrophage-targeted alginate nanoparticles for plasmid DNA encapsulation and delivery.

GFP- or IL-10-expressing plasmid DNA (400 μg) was mixed with an aqueous solution of medium viscosity alginate polymer (0.1% w/v) and stirred for an hour. The plasmid DNA-containing alginate solution was then cross-linked by drop-wise addition of calcium chloride (9 mM). The particles were then surface modified with 1 mg/ml of tuftsin peptide solution to target specific receptors on macrophages (FIG. 6). The control and peptide-modified nanoparticle formulations were characterized for particle size, surface charge, surface morphology, and DNA loading efficiency. Stability of encapsulated DNA was assessed by agarose gel electrophoresis. Toxicity of particles was evaluated by MTS assay in J774A.1 macrophage cell line. Time dependent cell uptake studies were carried out by encapsulating rhodamine-labeled dextran dye in nanoparticles and accessed via flow cytometry and fluorescence microscopy. Quantitative and qualitative transgene expression of GFP was assessed by fluorescence microscopy and ELISA, respectively at 12, 24, 48, 72, and 96 hours post administration. IL-10 transfection was measured by RT-PCR and the Quantikine® ELISA kit from R&D Systems.

The particle characterization studies showed that the DNA-loaded cross-linked alginate nanoparticles formed were spherical in shape with a mean diameter of approximately 300 nm-400 nm. On average, the surface charge of the unmodified formulation and the peptide-modified formulation were −47.7 mV and +19.7 mV, respectively, which also indicated successful peptide conjugation on the surface of the nanoparticles. Both GFP- and IL-10 expressing plasmid DNA were optimally encapsulated with an efficiency of approximately 58% and the stability studies confirmed that DNA remained intact during the formulation process.

Figure 7:
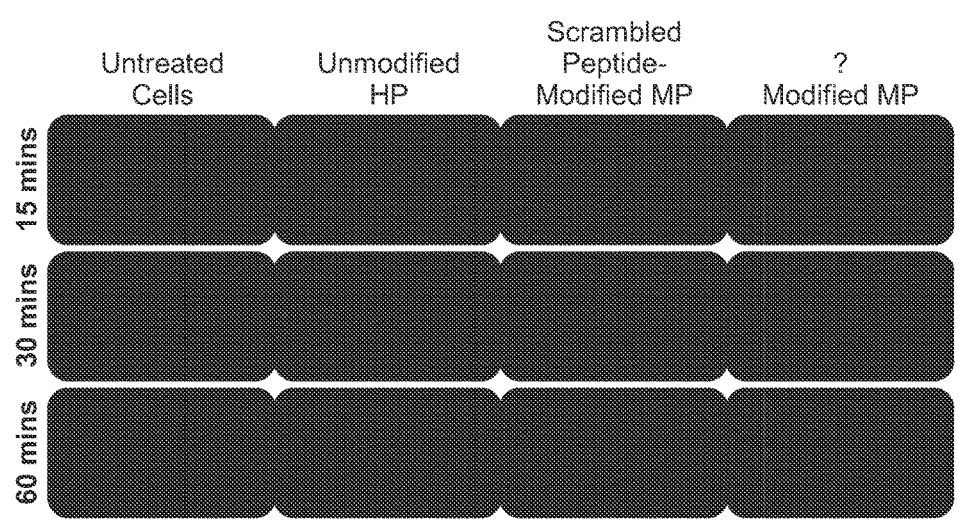
FIG. 7: Time-dependent fluorescence microscopy images of the untreated cells and cells treated with unmodified, scrambled peptide-modified, and tuftsin-modified rhodamine-dextran encapsulated alginate nanoparticles. The images were taken at 15, 30, and 60 minutes post-administration and the original magnification was 40×.

Time-dependent nanoparticle uptake in J774A.1 macrophage cell line was performed to justify the hypothesis that tuftsin-modified formulation should lead to a higher uptake as compared to the unmodified nanoparticles or those modified with a scrambled peptide sequence. Results of particle uptake were evaluated quantitatively and qualitatively by flow cytometry and fluorescence microscopy, respectively (FIG. 7). These studies showed that indeed the particle uptake in J774A. 1 macrophages was higher with tuftsin-modified formulation as compared to all the other controls. Moreover, the higher particle uptake with targeted formulation was observed at earlier time points (i.e, at 15 minutes, 30 minutes, and 60 minutes).

Figure 8:
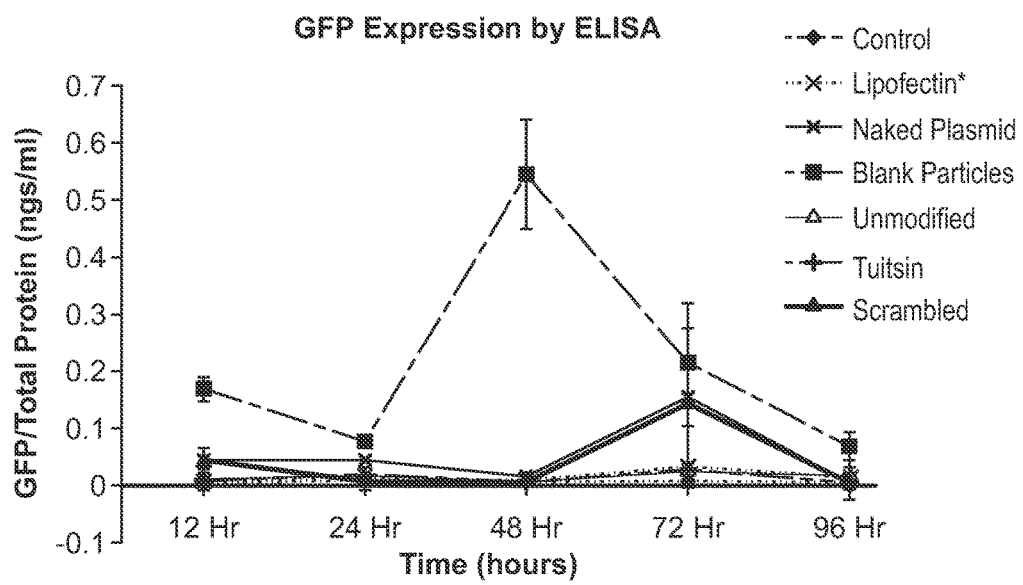
FIG. 8: Time-dependent quantitative analysis of GFP expression in J774A.1 macrophage cell line upon administration of EGFP-N1 plasmid DNA in control and tuftsin-modified alginate nanoparticles.

Both the quantitative and qualitative studies of transgene expression using GFP- and IL-10-expressing plasmid DNA were performed. The results of GFP-specific ELISA (FIG. 8) showed that protein expression was significantly higher in cells treated with tuftsin-modified nanoparticles as compared to the other controls, including positive controls such as Lipofectin® and scrambled peptide sequence (p<0.01; n=3). The qualitative GFP expression analysis by fluorescence microscopy also confirmed that tuftsin-modified nanoparticles showed higher transfection efficiency. Moreover, the protein expression could be observed over a period of more than 4 days following dosing.

Figure 9:
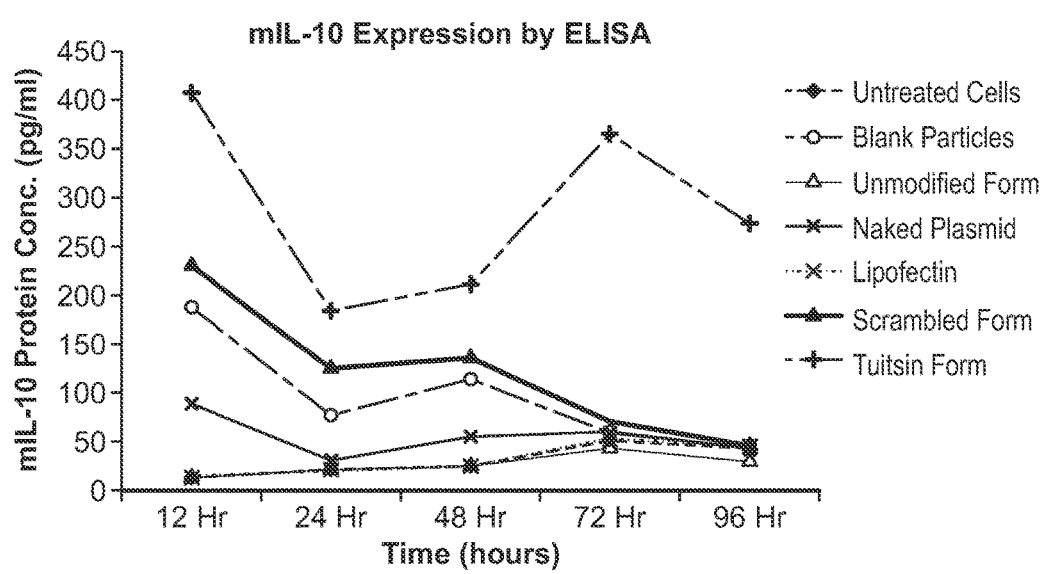
FIG. 9: Quantitative analysis of murine IL-IO transgene expression in J774A. 1 macrophages with controls and tuftsin-modified crosslinked alginate nanoparticles. The expression was monitored over a period of 4 days with mIL-I 0 specific ELISA. (n=4).

IL-10 transgene expression in J774A.1 macrophage cell line was examined and the results were very similar to those observed for GFP expression (FIG. 9).

Example 3

In Vitro Evaluations of Nanoparticles-in-Emulsion Formulations for Gene Delivery and Transfection in Macrophages Summary Gene delivery vehicles capable of transfecting into specific cells leading to sustained production of therapeutically active proteins can serve as a very effective strategy for disease treatment. In this study, solid nanoparticles-in-emulsion (NiE) formulations were developed and evaluated in vitro for gene delivery and transfection in adherent alveolar macrophages. A reporter plasmid expressing enhanced green fluorescent protein (EGFP-N1) was encapsulated in gelatin nanoparticles (GNP), which were further encapsulated in the inner aqueous phase of safflower oil-containing W/O/W multiple emulsions.

Results of this study show that NiE formulations were more efficient in transfection of EGFP-N1 in alveolar macrophages as compared to the control formulations such as DNA dissolved in the aqueous phase of the W/O/W multiple emulsion (ME), DNA encapsulated in GNP, or when DNA was complexed with Lipofectin®, a cationic lipid-based transfection reagent.

Introduction

Gene therapy involves delivery of therapeutic genes into specific cells followed by transcription and translation into biologically-active protein for treatment of different acute and chronic diseased conditions. With the decoding of human genome and recent advances in biological engineering, a large number of therapeutic gene sequences are known. These gene sequences can be used for production of desired protein within specific cells in the body (1). To achieve this purpose, development of a delivery vehicle that is able to efficiently deliver genes into specific cells is useful. Although viral vectors have high gene transfection efficiency, their clinical use has been limited due to cytotoxicity, immunogenicity, and chromosomal integration of delivered genes.

Non-viral gene delivery systems targeted towards macrophages provide a unique way to control acute and chronic inflammatory diseases. In this study, NiE was developed as a novel macrophage-targeted system for gene delivery and transfection, especially following mucosal administration. Such a multi-compartmental delivery system also provides a way to encapsulate different types of therapeutic or imaging payloads in the inner and outer compartments for greater stability or temporal-controlled delivery. The disclosure provides results obtained from in vitro gene transfection experiments using EGFP-N1 plasmid DNA in murine adherent alveolar macrophages J774.A1 cells.

Experimental Methods

Type B GNP was prepared by ethanol-water solvent displacement method as described previously (3). Particle size and charge were determined using Malvern Zetasizer®. W/O/W multiple emulsion was formulated by a two step emulsification process using a Silverson Homogenizer® L4RT (5). For cellular uptake studies, rhodamine-labeled dextran, a water-soluble fluorophore, was incorporated in the internal aqueous phase of ME or encapsulated in GNP, which were then incorporated in the inner aqueous phase. Cellular uptake studies were performed by fluorescence microscopic imaging of control and treated J77A.1 cells. For gene transfection studies, EGFP-N1 was encapsulated in GNP, which was then incorporated in the inner aqueous phase of the ME. EGFP-N1 loading in different formulations was evaluated using PicoGreen® dsDNA reagent. EGFP-N1 stability in different formulations was characterized by using agarose gel electrophoresis. Cells treated with different EGFP-N1 encapsulated formulations and complexed with Lipofectin® was examined for transgene expression qualitatively by fluorescent microscopy and quantitatively by green fluorescent protein (GFP)-specific enzyme-linked immunosorbent assay (ELISA).

Results And Discussion

Figure 10:
FIG. 10: Bright-field and fluorescent microscopy images of NiB (A&B) and ME (C&D) showing stable non-leaky multiple emulsion globules of 5.0 µm or less diameter. Original magnification was 60× Bright-field and fluorescent images in E,F,G and H represent cellular uptake of NiE (E,F) and ME (G,H) in J774A.1 macrophage cells after 2 hours. Original magnification was 40×.

The blank and EGFP-N1-loaded GNP had an average particle size of 164.3 nm and 166.0 nm, respectively. The surface charge of blank and EGFP-N1-loaded gelatin nanoparticles was found to be −10.7 mV and −11.2 mV, respectively. ME and NiE had globule size of 5 μm or less with no signs of leakage of contents from the inner aqueous phase (FIG. 10). Loading efficiency of EGFP-N1 in GNP, ME, and NiE was found to be 99%, 54%, and 70%, respectively. Agarose gel electrophoresis results from all the three formulations showed a single band at 4.7 kb size, which was similar to that of pure EGFP-N1. These results showed that the plasmid was not affected negatively by the formulation processing conditions. Cellular uptake studies showed rapid uptake of ME and NiE formulation with saturation in 2 hour post-treatment (FIG. 10).

Figure 11:
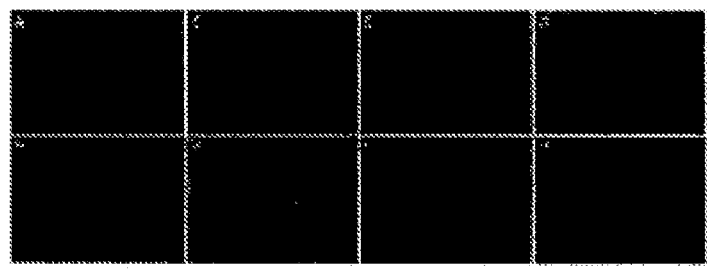
FIG. 11: Differential interference contrast and fluorescent microscopy images showing green fluorescent protein expression of in J774A.1 cells 24 hour post-treatment with EGFP-N1 plasmid DNA complexed with Lipofectin® (A,B), or encapsulated in NiE (C,D), ME (E, F) and GNP (G,H). Original magnification was 40×.

Qualitative green fluorescent protein (GFP) expression was evaluated by fluorescent microscopy. The images were obtained for cells treated with EGFP-N1-loaded GNP, ME, NiE and complexed with Lipofectin®. Maximum green fluorescence was observed in NiE treated J774A.1 macrophage cells followed by treatment with other formulations (FIG. 11).

Figure 12:
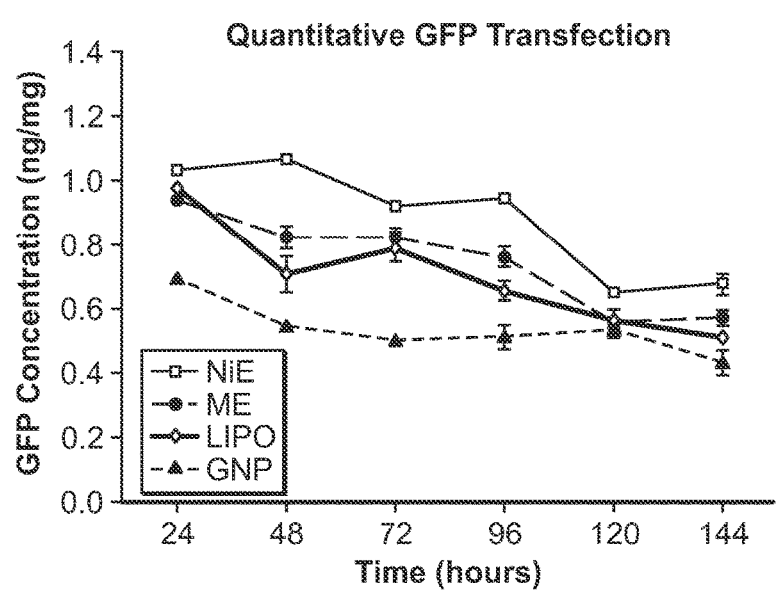
FIG. 12: Quantitative green fluorescent protein (GFP) expression by ELISA showing transgene expression with EGFP-N1 plasmid DNA encapsulated in GNP, ME, and NiB as well as complexed with Lipofectin®. Highest levels of GFP expression was observed with NiE formulation relative to all other tested.

Quantitative GFP expression analysis in J774A.1 macrophages was determined using a specific ELISA. Transfection efficiency was reported as nanograms of GFP produced per milligram of total cellular proteins. The ELISA results, as shown in FIG. 12, indicated that NiE formulation had the highest transfection efficiency as compared to other formulations in this in vitro system with J774A.1 cells.

Description

The results of this study show that solid gelatin nanoparticles can be effectively encapsulated in safflower oil-containing W/O/W multiple emulsion. This NiE system can be used for gene transfection in macrophages and may prove beneficial for mucosal transfection following oral administration.

Example 4

Oral TNF-α Gene Silencing with NiMOS

Summary

This example evaluated down-regulation of TNF-α by oral RNA interference therapy. Control (scrambled sequence) or TNF-α specific small interfering RNA (siRNA) was encapsulated in type B gelatin nanoparticles and further entrapped in poly(epsilon-caprolactone) (PCL) microspheres to form a nanoparticles-in-microsphere oral system (NiMOS). Upon confirmation of the dextran sulfate sodium (DSS)-induced acute colitis model, mice were divided into several treatment groups receiving no treatment, blank NiMOS, NiMOS with scramble siRNA, or NiMOS with TNF-α silencing siRNA by oral administration. Successful gene silencing led to decreased colonic levels of TNF-α, suppressed expression of other pro-inflammatory cytokines (IL-1α, IL-1β, IFN-γ) and chemokines (MCP-1), an increase in body weight, and reduced tissue myeloperoxidase activity. Results of this study establish the clinical utility of a NiMOS-based oral TNF-α gene silencing system for the treatment of inflammatory bowel disease as demonstrated in an acute colitis model.

Introduction

Inflammatory bowel disease (IBD), represented by two main phenotypes—Crohn's disease and ulcerative colitis—is a chronic relapsing condition involving inflammation of the gastrointestinal tract. While its etiology is still unknown, a complex interaction of genetic disposition, environmental conditions, life style, microbial and immune factors have been identified as some of the major aspects leading to IBD (1, 2). Conventional treatment consists of anti-inflammatory and immune-suppressive drugs (3), depending on the patient's clinical state including extent and severity of the disease. Some medications are effective measures to combat inflammation in the acute setting, but ineffective in maintaining remission due to toxicity, dependency and higher relapse rates. Another treatment option is surgical removal of the inflamed intestinal tissue; however patients have to undergo a great deal of mental stress and physical suffering. Due to the limitations in efficacy and safety associated with the current treatment options, development of novel biological therapies involving selective blockage of mucosal inflammatory pathways, offer potential for more effective treatment options in IBD.

Tumor necrosis factor-alpha (TNF-α) plays a central role in the mediation of inflammation in IBD (5). While systemic anti-TNF-α works well in patients refractory to conventional therapy, serious contraindications and side effects including opportunistic infections, antibody formation against anti-TNF-α in conjunction with decreased efficacy of the therapy, and increased occurrence of infusion reactions have been reported (6, 8, 9). The gastrointestinal tract offers an ideal target for gene therapy due to the large surface area and access to the luminal site of inflammation via oral and rectal routes of administration.

RNA interference therapy utilizes short interfering RNA (siRNA), usually composed of 20-25 nucleotides, and is involved in a gene-silencing mechanism through RNA interference where siRNA can ultimately block the expression of a specific gene, e.g. those expressed in diseases. Thus, application of siRNA offers an alternative therapeutic strategy to overcome a disease. Currently, the biggest hurdle in gene silencing remains delivery and stability due to rapid degradation of siRNA in the cytoplasm and plasma. For this purpose, encapsulation and delivery mechanisms have been employed involving various systems including viral vectors, nanoparticles 18, polymer-based vehicles or liposomal vesicles.

Disclosed herein is the development of multicompartmental nanoparticles-in-microsphere system (NiMOS) using gelatin nanoparticles encapsulating reporter and therapeutic protein expressing plasmid DNA encased in a PCL shell and shown successful transfection in rodent models. Here, the control (scrambled TNF-α) was encapsulated in gelatin nanoparticles (forming NiMOS). TNF-α specific siRNA was also encapsulated in gelatin nanoparticles. This was done in order to evaluate the potential of oral delivery for TNF-α gene silencing in IBD by administration in a DSS-induced acute colitis mouse model.

Materials

Type-B gelatin (MW 40,000-50,000, 100-115 mM of free carboxylic acid per 100 g of protein, pI of 4.7-5.2) of 225 bloom strength and Poly(vinyl alcohol) (PVA) (degree of hydrolysis 86.7-88.7%, MW ~67,000) were obtained from Sigma Chemical Company, (St. Louis, Mo.). Poly(epsilon-caprolactone) (PCL) (MW 10,000-20,000 as verified by gel permeation chromatography) was purchased from Polysciences, Inc. (Warrington, Pa.). Reagent grade dichloromethane, haematoxylin and eosin were purchased from Fisher Scientific (Pittsburgh, Pa.). Reagent grade absolute ethanol was obtained from Acros Organics (Parsipanny, N.J.). For encapsulation efficacy studies and gel electrophoresis bovine pancreatic protease with an activity of 6.9 units/mg was obtained from Sigma Chemical Company (St. Louis, Mo.). Desalted and annealed siRNAs were obtained from Dharmacon (Lafayette, Colo.). The sequences were as follows: TNF-α siRNA, 5'GACAACCAACUAGUG-GUGCdTdT3'; scramble siRNA, 5'GACAACCA-GGGCGUGGUGCdTdT3'14. Only sense sequence is shown. For the animal studies, dextran sodium sulfate (DSS) (MW 36,000-50,000) was purchased from MP Biomedicals United States (Solon, Ohio). All other reagents and chemicals were of analytical grade. Aqueous solutions were prepared exclusively in deionized distilled water (Nanopure II, Barnstead/Thermolyne, Dubuque, Iowa). Balb/c mice were purchased from Charles River laboratories (Wilmington, Mass.). RNAse A and Superscript III were obtained from Invitrogen (Carlsbad, Calif.).

Methods

Formulation of Gelatin Nanoparticles and NiMOS Encapsulating siRNA

Gelatin nanoparticles were prepared as described previously. In brief, siRNAs were mixed with aqueous gelatin solutions of pH 7.00 and pre-incubated for 10 min at room temperature followed by controlled precipitation of siRNA-containing or blank gelatin solutions with the aid of ethanol as the non solvent. In the final blend, the ethanol-to-water volume ratio was kept constant at 65:35. The resulting nanoparticles were centrifuged at 32,000 rpm for 45 min, washed with deionized water and lyophilized.

Nanoparticle-in-microspheres-oral delivery systems (Ni-MOS) were manufactured by utilizing a "double emulsion-like" technique, as described herein.

Characterization of Gelatin Nanoparticles and NiMOS Encapsulating siRNA

Particle Size Analysis

Freshly prepared nanoparticle formulations were characterized for the mean particle size of the droplets using the Malvern Zetasizer Nano ZS 90 apparatus (Westborough, Mass.) at a 90° scattering angle. NiMOS were characterized for particle size and size distribution using Multisizer™ 3 from Beckman Coulter (Fullerton, Calif.). All measurements of particle size were carried out at room temperature.

Scanning Electron Microscopy (SEM)

Lyophilized blank or loaded gelatin nanoparticles and NiMOS were mounted on an aluminum stub and sputter coated with gold-palladium to minimize surface charging. Samples prepared in this manner were evaluated according their surface morphology with a Hitachi S-4800 (Pleasanton, Calif.) field emission scanning electron microscope.

Determination of siRNA Loading in Gelatin Nanoparticles and NiMOS siRNA-loaded gelatin nanoparticles and NiMOS were prepared as discussed above. Encapsulation efficiency of siRNA in these formulations was determined by dissolving a known amount of sample in phosphate buffered saline (PBS, pH 7.4) containing 0.2 mg/ml protease at 37° C. until a clear solution was obtained. Released siRNA was quantified using the PicoGreen® assay (Invitrogen, Carlsbad, Calif.) according to the manufacturer's protocol. The intensity of fluorescence which is proportional to the PicoGreen® bound siRNA was measured at an excitation of 485 nm and emission of 520 nm wavelengths using a Perkin Elmer LS50B spectrophotometer (Norwalk, Conn.). FLWIN-LAB® software was used for processing and analysis of resulting data.

Evaluation of siRNA loading in NiMOS was carried out as described before (23). Briefly, a known amount of the previously described samples was added to a known amount of dichloromethane to dissolve the PCL matrix and release the gelatin nanoparticles. To this organic PCL-dicholoromethane mixture, an equal amount of distilled deionized water was added to separate the nanoparticles from the organic solution. After careful separation of the aqueous from the organic phase, gelatin nanoparticles underwent the same procedure as described above to measure the final siRNA loading efficiency in the NiMOS using the PicoGreen® quantitation assay.

siRNA Stability

To ensure that the manufacturing process of gelatin nanoparticles of NiMOS did not affect the integrity of siRNA, stability of encapsulated siRNA was assessed by agarose gel electrophoresis. Additionally, the integrity of the payload in the presence of RNAse A was determined. A sample of siRNA containing NiMOS was treated with RNAse A for 20 min at 37° C. followed by inactivation of the enzyme and extraction of siRNA from loaded nanoparticles by protease digestion of the gelatin matrix that were extracted in the same manner as discussed above. After siRNA release from microspheres and nanoparticles, samples were added to the wells of a 4% (w/v) pre-stained E-gel™ system and run against a 10 bp ladder, naked siRNA, naked siRNA treated with protease, and naked siRNA treated with protease and RNAse A as controls. After a 45 min run at 70V, the image was recorded under UV light and processed.

Experimental Animals

All animal studies involved were performed in accordance with the experimental protocol approved by the Institutional Animal Care and Use Committee at Northeastern University (Boston, Mass.). Female Balb/c mice (6-8 weeks, ~18-20 g) were purchased from Charles River Laboratories (Wilmington, Mass.). Animals were randomly assigned to groups of 4 mice per cage and acclimatized for 10 days before begin of the study. The mice were housed in rooms at a controlled temperature of 22° C. and 26% humidity, respectively, with light-dark cycles of 12 hours and fed with water and a standard pellet at libitum except when fasted overnight to prepare for the oral gavage.

Induction of Acute Colitis Using Dextran Sodium Sulfate (DSS)

Animals were randomly assigned to ten groups (n=4). Acute colitis was induced in mice by addition of 3.5% (w/w) dextran sodium sulfate (DSS) in their drinking water for the duration of the study, while one control group (n=8) received regular tab water throughout the course of the study. DSS solutions were freshly prepared on a daily basis and mice were monitored daily for their health condition. The acute disease model was confirmed by evaluation of weight loss, stool consistency, rectal bleeding, and tissue histology. At days 10 and 14 of the study, animals were sacrificed by $CO_2$ inhalation followed by cervical dislocation and tissue was processed as described below.

Oral siRNA Administration in DSS Colitis-Induced Balb/c Mice

On days 2, 4, and 6 of the study, mice of each group including all controls were fasted overnight followed by treatment with blank NiMOS (particles containing no siRNA) or microparticles containing 750 pmol siRNA (TNF α or TNFα scrambled sequence) per animal by oral gavage using a blunt-tipped feeding needle inserted into the esophagus adding up to three doses of NiMOS formulations per group. An additional control group consisted of animals receiving no oral treatment throughout the course of DSS exposure (DSS control).

At predetermined time points of 3 and 7 days post-administration (days 10 and 14, respectively), 4 animals per time point and group were sacrificed using $CO_2$ inhalation followed by cervical dislocation. After euthanasia, the large intestine was surgically removed and carefully washed with PBS for histological analysis of the tissue sections and determination of cytokine and murine TNFα-mRNA levels by Multiplex ELISA and real-time PCR, respectively.

Isolation of RNA from Colon Tissue and Quantitative Polymerase Chain Reaction

Tissue samples obtained from the large intestine were stored in RNAlater® (Applied Biosystems Inc., Foster City, Calif.) at 4° C. for 2 days to allow enough time for tissue penetration followed by removal of excess liquid and storage of tissue at −70° C. until processing. RNA was isolated from tissue samples using the guanidine isothiocyanate method supplied in the RNAqueous®-4PCR kit (Applied Biosystems Inc., Foster City, Calif.) according to the manufacturer's protocol. The isolated RNA from the tissue samples described above was quantified by using the NanoDrop 1000 (Thermo Fisher Scientific Inc., Wilmington, Del.) UV-Vis spectrophotometer.

Synthesis of cDNA from Isolated mRNA by Reverse Transcription

After determinations of the total RNA concentration, the samples were stored at −70° C. until further use. cDNA was synthesized from RNA using the Superscript III First-Strand Synthesis SuperMix for qt-PCR (Invitrogen, Carlsbad, Calif.) as recommended by the manufacturer. The preparation for reverse transcription of RNA samples was performed on ice and in accordance with the manufacturer's recommendation. A volume corresponding to 1 µg of RNA as determined by UV spectrophotometric analysis was used for the synthesis process. Samples containing cDNA were diluted to a final volume of 100 µl and stored at −20° C. until further use.

Quantitative Analysis of cDNA by Polymerase Chain Reaction (PCR)

Quantitative real time PCR was performed on cDNA samples obtained from large intestinal tissue to determine the levels of mRNA transcript. L32 gene expressing the L32 ribosomal protein served as a control. Pre-diluted cDNA was mixed with 0.2µ of primer pair detecting the murine TNF-α or L32 construct and SYBR® Green PCR master mix and pipetted into an ABI Prism™ 96-well optical reaction plate with barcode (Applied Biosystems, Foster City, Calif.). The sequences of the primers used were as follows: (1) murine L32 5'AGCAACAAGAAAACCAAGCACAT3' and 5'TTGACATTGTGGACCAGGAACT3', (2) murine TNF-α 5'CATGAGCACAGAAAGCATGATC3' and 5'CCTTCTCCAGCTGGAAGACT3'. The quantitative PCR reaction was performed in the 7300 Real-Time PCR System from Applied Biosystems using the following cycle program: 40 cycles 95° C. for 15 seconds; 60° C. for 1 minute. Results obtained from the PCR reaction were analyzed by comparative Ct analysis to determine the relative amount of murine TNF-α cDNA in the samples.

Determination of Tissue Murine Cytokine Expression Levels by ELISA

For subsequent ELISA and measurement of myeloperoxidase activity, samples of the entire large intestine were homogenized in lysis buffer (1 M Tris, pH 7.4; 0.5 M EDTA, pH 8.0; 5 M NaCl, 10% (w/v) Brij, 10% (v/v) Tween 20), supplemented with proteinase inhibitor, on ice to extract the proteins from the tissue samples. Protein containing supernatant was separated by centrifugation at 13000 g for 30 min at 4° C. and stored at −70° C. until analysis. The Q-Plex™ Mouse Cytokine Screen ELISA obtained from Quansys Biosciences (Logan, Utah) was used to measure changes in concentration of a series of pro- and anti-inflammatory cytokine (TNF-α, IL-1α, IL-1β, IL-2, IFN-γ, IL-5, IL-6, IL-12p70, IL-17, MIP-1α, MCP-1, and GMCSF) in the large intestine of colitis-induced Balb/c mice according to the manufacturer's protocol. Luminescence intensity of each sample was measured and the concentration of each cytokine was analyzed with a five-parameter curve fitting using the Q-View™ software (Quansys Biosciences). Cytokine concentrations obtained from the multiplex ELISA were normalized against the total protein content of each individual sample as determined by bicinchoninic acid assay (Pierce, Rockford, Ill.). Values are expressed as pictogram (pg) or femtogram (fg) of murine cytokine expressed per mg of total protein content of each sample and represent mean±S.D. of 4 mice.

Histological Analysis of Tissue Sections by H&E Staining

Tissue samples were evaluated for mucosal architectural change, cellular infiltration, inflammation, external muscle thickening, presence of crypt abscess, goblet cell depletion, signs of edema, surface epithelial cell hyperplasia, and signs of epithelial regeneration by using light microscopy of hematoxylin and eosin survey staining (25, 35). These values were used to assess the degree of mucosal damage and repair in treatment and control groups. Tissue samples harvested from distal regions of the non-/inflamed colon were stored in 10% formalin solution at 4° C. for at least 2 days to fix the tissue. After that, samples were washed with PBS to remove excessive formalin solution and then transferred to 30% (w/w) sucrose solution for 2 days to prepare for subsequent cryosectioning of the tissue with the purpose of protection from freezing damage. Tissue sections with a thickness of 7 µm were stained with haematoxylin and eosin according to protocols supplied by the manufacturer followed by imaging using bright-field microscopy (Olympus BX51TRF, Olympus America, Center Valley, Pa.).

Determination of Tissue Myeloperoxidase Activity

Tissue myeloperoxidase activity was detected with the FluoroMPO kit purchased from Cell Technology, Inc. (Mountain View, Calif.). In preparation of this, tissue samples were minced in hexadecyltrimethylammonium bromide buffer (0.5% in 50 mM phosphate buffer) on ice and homogenized. The homogenate was sonicated, subjected to a freeze-thaw cycle and centrifuged at 10,000 rpm for 3 minutes. A certain known amount of the tissue lysate supernatant was combined with the detection mix containing $H_2O_2$, a non-fluorescent detection reagent and 1× assay buffer. The detection reagent is oxidized in the presence of hydrogen peroxide and MPO to produce its fluorescent analog which was measured at an excitation wavelength of 530 nm and emission at 590 nm. Reported values a normalized to mg of total protein content of the sample.

Statistical Analysis

All data shown are represented as mean±standard deviation (S.D.). Statistical differences between control and treatment groups were determined using the Student's t test.

Results

NiMOS for Oral TNF-α Gene Silencing

Figures 13A, 13B:
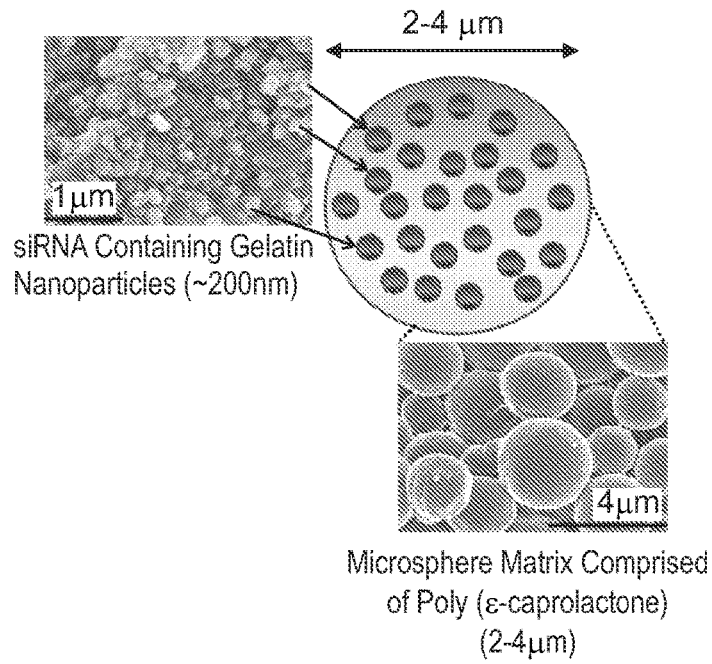
FIG. 13A-B: Formulation of siRNA-encapsulated nanoparticles and NiMOS. a) Schematic representation of the NiMOS including scanning electron micrographs of small interfering RNA (siRNA)-encapsulated type B gelatin nanoparticles and siRNA-containing NiMOS. The magnification is represented by the scale bar in the lower right corner of each image. b) Qualitative agarose gel (4% (w/v)) electrophoresis to show stability of siRNA in the NiMOS. Lane I: 10 bp ladder; lane 2: naked siRNA; lane 3: naked siRNA treated with protease; lane 4: naked siRNA treated with protease and RNAse A; lane 5: siRNA extracted from gelatin nanoparticles; lane 6: siRNA extracted from gelatin nanoparticles and then treated with RNAse A; lane 7: siRNA extracted from NiMOS; lane 8: siRNA extracted from NiMOS pre-treated with RNAse A; lane 9: siRNA extracted from NiMOS and then treated with RNAse A; lane 10: 10 bp ladder; and lane II: NiMOS treated with protease only. c) The siRNA-encapsulated gelatin nanoparticles had an average diameter of less than 300 nm with a narrow size distribution, and an encapsulation efficiency of approximately 90:1:5%. siRNA-encapsulated NiMOS had an average diameter of 2.4:1:0.9 um with a narrow size distribution. Encapsulating efficiency of siRNA decreased to approximately 55±3% in NiMOS.

An illustration of NiMOS and scanning electron micrographs of siRNA encapsulating gelatin nanoparticles and microspheres is shown in FIG. 13A. Using the solvent displacement method, spherical gelatin nanoparticles encapsulating siRNA with a mean diameter of 279.2 nm±3.2 nm were produced. For additional protection from pH and enzymatic degradation during the gastrointestinal transit, the nanoparticles were further encapsulated in PCL microspheres to create NiMOS. These were of fairly uniform shape and size with a relatively smooth surface morphology, and diameters ranging from 2.4 μm to 3.2 μm for blank and siRNA encapsulating microparticles, respectively (FIG. 13C).

To ensure that siRNA was not affected during the manufacturing processes and that particles can efficiently protect this payload in the presence of degrading enzymes, the stability of extracted siRNA was evaluated by agarose gel electrophoresis. Based on these studies, encapsulation does not appear to affect the structure or size of siRNA (FIG. 13B). For example, siRNA from gelatin nanoparticles (lane 5) and NiMOS (lanes 7, 8) had the same size as control siRNA (lane 2). Furthermore, protease addition had no adverse effect on siRNA (lane 3). Additionally, NiMOS appeared to have a protective effect on the payload. This was demonstrated by the band in lane 7; NiMOS were exposed to RNAse A followed by inactivation of the enzyme and extraction of the siRNA revealing a fragment with the same size as control counterparts. However, siRNA released from gelatin nanoparticles was completely degraded when exposed to protease and RNAse, (lanes 6, 9). Exposure of NiMOS to protease alone did not liberate siRNA (no band; lane 11). Quantification of encapsulated siRNA revealed a loading efficiency of 90.2±5.4% in gelatin nanoparticles. Final siRNA loading efficiency in NiMOS was measured to be 55.2±2.8% of the added siRNA.

Acute DSS-Induced Colitis Model

Figure 14A:
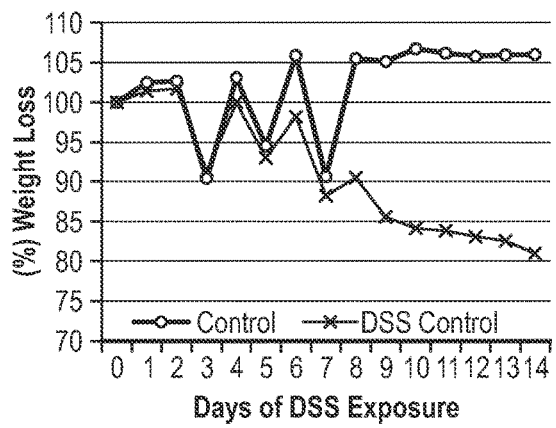
FIG. 14A-C: Dextran sulfate sodium-induced acute colitis murine model. a) Percent weight loss in 6-8 weeks old female Balb/c mice fed with 3.5% (w/w) dextran sulfate sodium (DSS) to induce acute colitis in comparison to weight of the control mice fed with regular drinking water. Dips in the curve body correspond to weight measurements immediately following the fasting periods. b) Tissue myeloperoxidase activity per mg total protein content in the same group of mice. c) Bright-field images of H&E stained sections of the colon harvested from each group. Images are shown at 10× and 40× of original magnifications. Sections from the control group exhibit features normal. and healthy colon tissue. Intestinal tissues from the DSS control group showed a significant level of infiltration of white blood cells, abnormal mucosal architecture and goblet cell depletion.
Figure 14B:
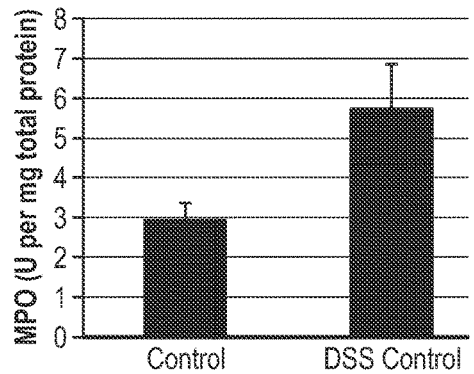
Figure 14C:
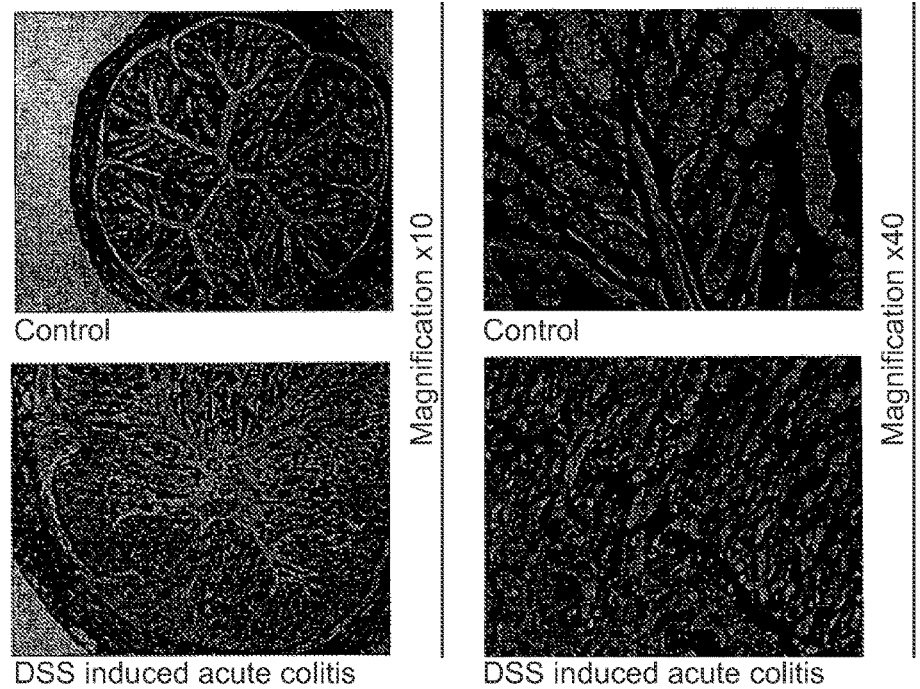

After 5 days of DSS administration in drinking water, mice showed typical symptoms of IBD including weight loss (FIG. 14A), diarrhea, rectal bleeding, and signs of inflammation as evidenced by elevated myeloperoxidase levels (FIG. 14B), a significant degree of white blood cell infiltration, and abnormal mucosal architecture including goblet cell depletion (FIG. 14C).

TNF-α Gene Silencing

Figure 15A:
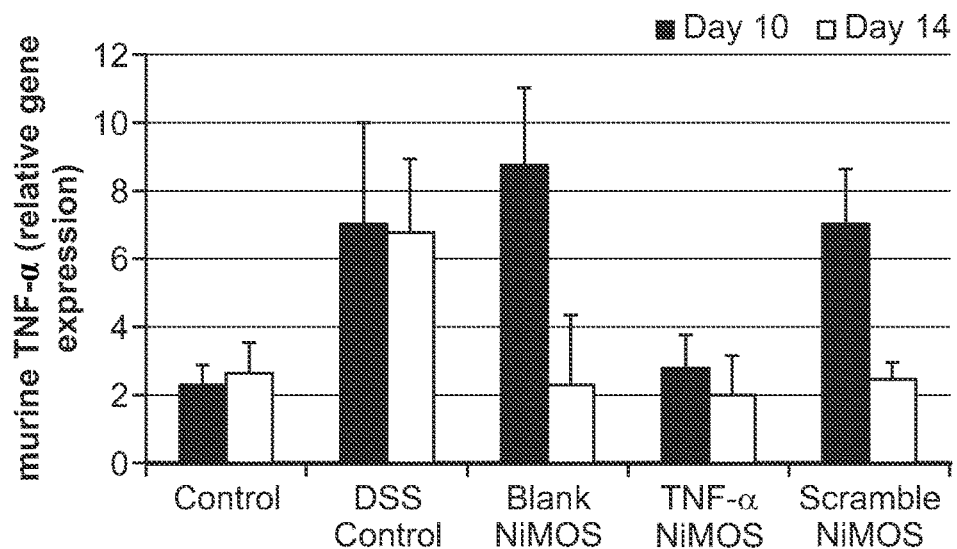
FIG. 15A-B: In vivo TNF-gene silencing. Murine TNF-expression upon oral delivery of siRNA against TNF-11 using NiMOS in a dextran sulfate (DSS)-induced acute colitis mouse model. a) Quantitative real time-PCR analysis performed on samples of the large intestines obtained from control and experimental treatment groups showing lower mRNA transcript upon oral administration of siRNA with NiMOS. b) Levels of 1NF-a as determined by ELISA. Values are represented as mean±S.D. (n=3-4). Control=naive, no colitis; DSS Control=colitis, no treatment; Blank NiMOS=colitis, blank microspheres; TNF-NiMOS=colitis, TNF-siRNA containing microspheres; Scramble NiMOS=colitis, scramble siRNA containing microspheres.

Quantitative real time PCR (qPCR) analysis was performed to assess expression of murine TNF-α at the mRNA level on day-10 and 14 of the study (FIG. 15A). On day-10, the TNF-α mRNA transcript was lowest in the treatment group receiving TNF-α siRNA encapsulating NiMOS. At this time point, the highest values were observed in the control group administered with blank NiMOS. No significant differences were observed on day-14 in TNF-α mRNA levels of animals receiving blank, scramble, or TNF-α NiMOS.

Figure 15B:
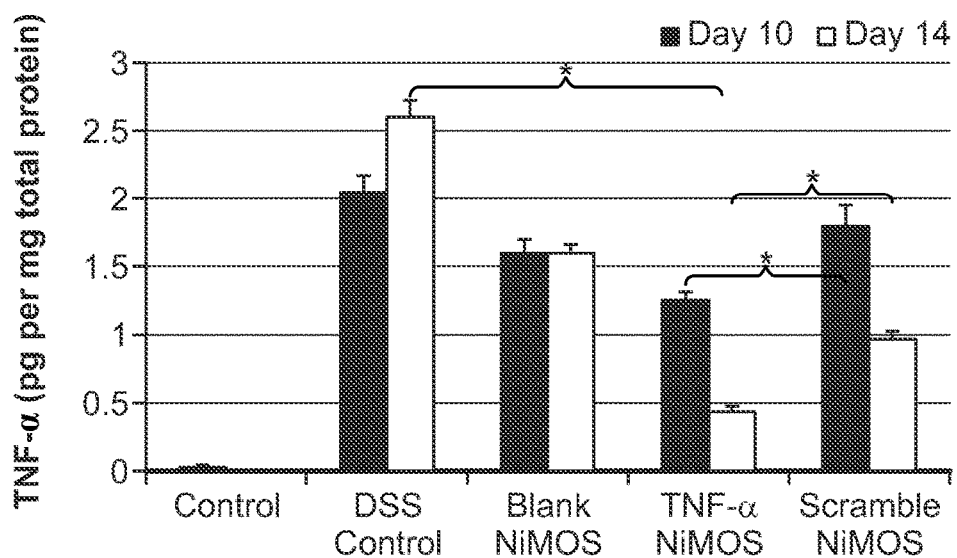
Figure 16A:
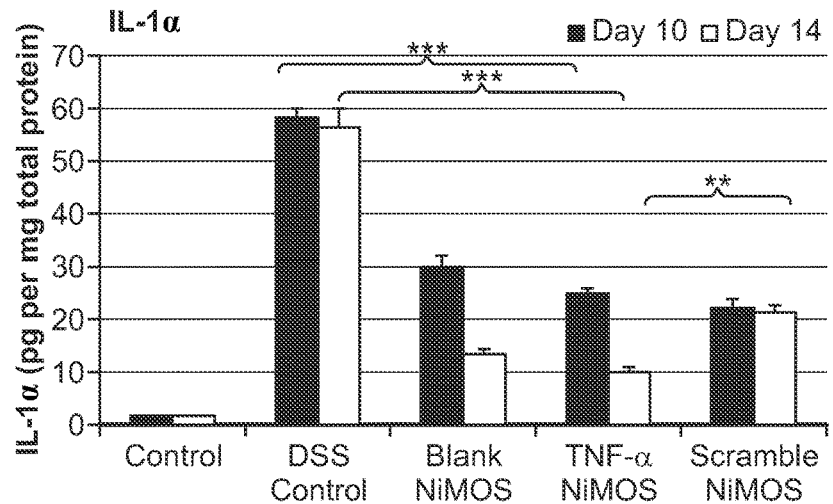
FIG. 16A-I and FIG. 16K: Cytokine and chemokine profiles in the GI tract. The cytokine expression profile upon administration of three doses of NiMOS (blank or encapsulating TNF-siRNA, scramble siRNA) to animals under continuous dextran sodium sulfate (DSS) exposure was determined using a chemiluminescent ELISA Q-Plex™ Mouse Cytokine Screen (Quansys Biosciences, Logan, Utah). Concentrations of a) Interleukin-I alpha (IL-1), b) Interleukin I beta (IL-1β), c) Interleukin 2 (IL-2), d) Interferon gamma (IFN-), e) Interleukin 5 (IL-5), f) Interleukin 6 (IL-6), g) Interleukin 12 p70 (IL-12 p70), and h) Interleukin 7 (IL-7) in the large intestine are shown. Levels of pro-inflammatory cytokines are low in the healthy control group at both time points as compared to inflamed tissue. The highest concentration of pro-inflammatory cytokines was observed in animals treated with blank or scrambled siRNA containing NiMOS. Levels were lowest in groups receiving TNF-silencing siRNA. Profiles of proinflammatory chemokine in colonic tissue of control and treatment group mice with induction of acute DSS colitis. (i) levels of chemokines three days post-administration or day 10 of the study and (k) protein concentrations on day 14 of the study. Granulocyte macrophage colony-stimulating factor (GMCSF); monocyte chemotactic protein-I (MCP-I); monocyte inflammatory protein I alpha (MIP-1). Values expressed as mean±S.D. (n=4).
Figure 16B:
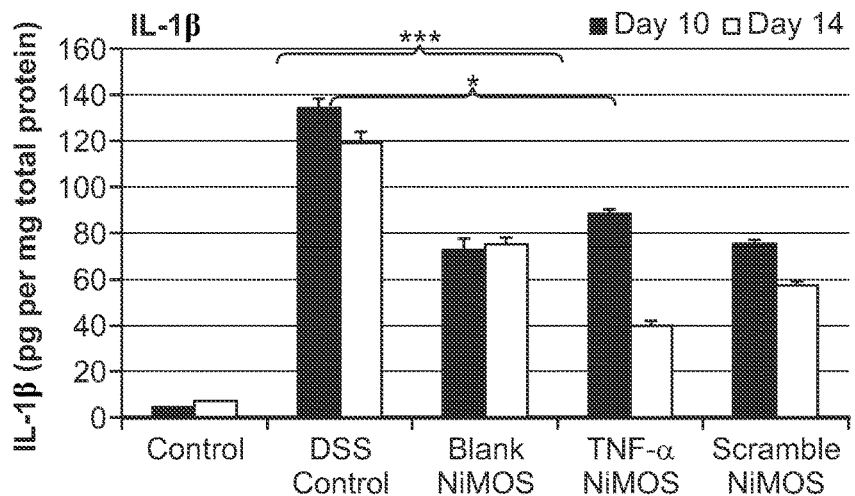
Figure 16C:
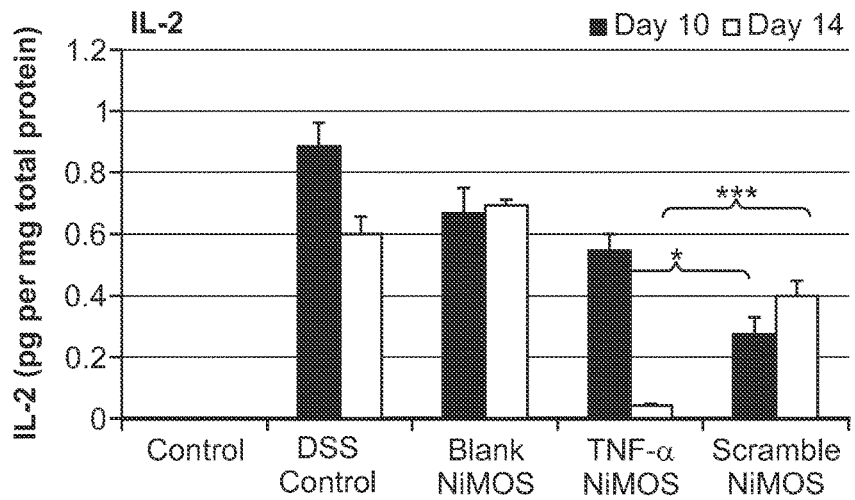
Figure 16D:
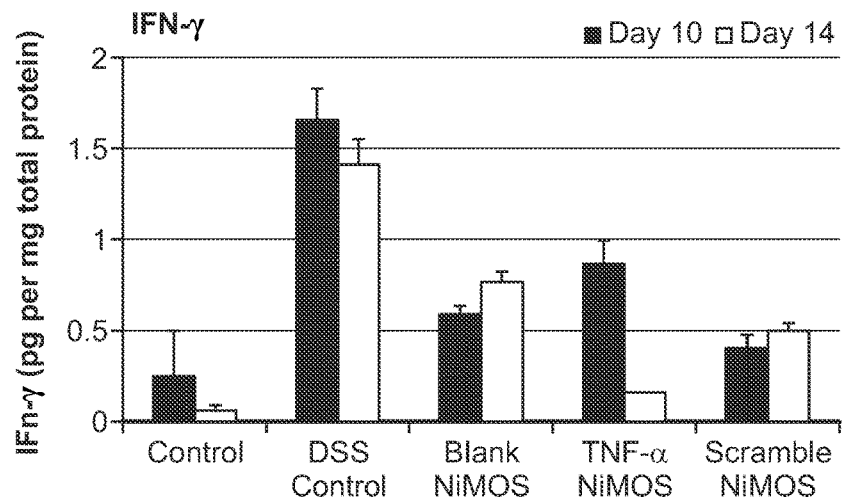
Figure 16E:
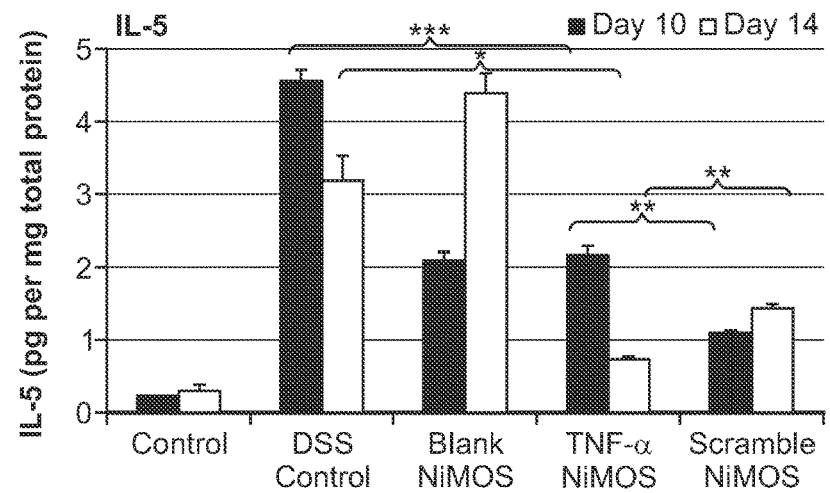
Figure 16F:
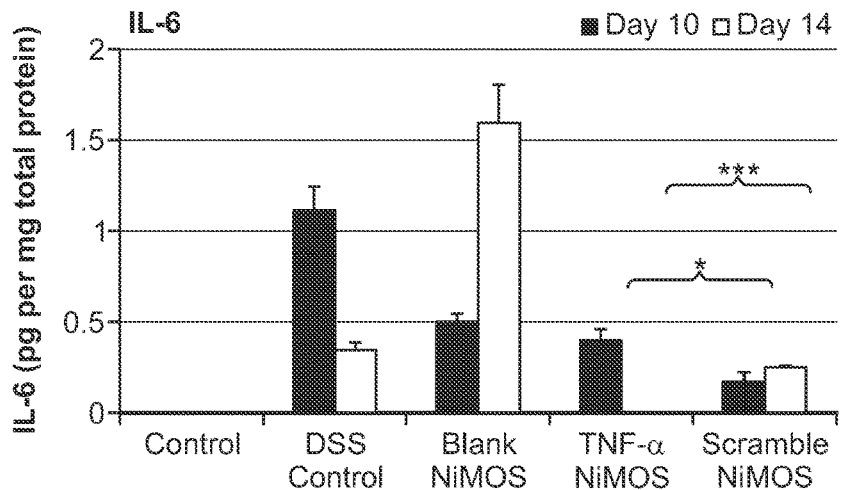
Figure 16G:
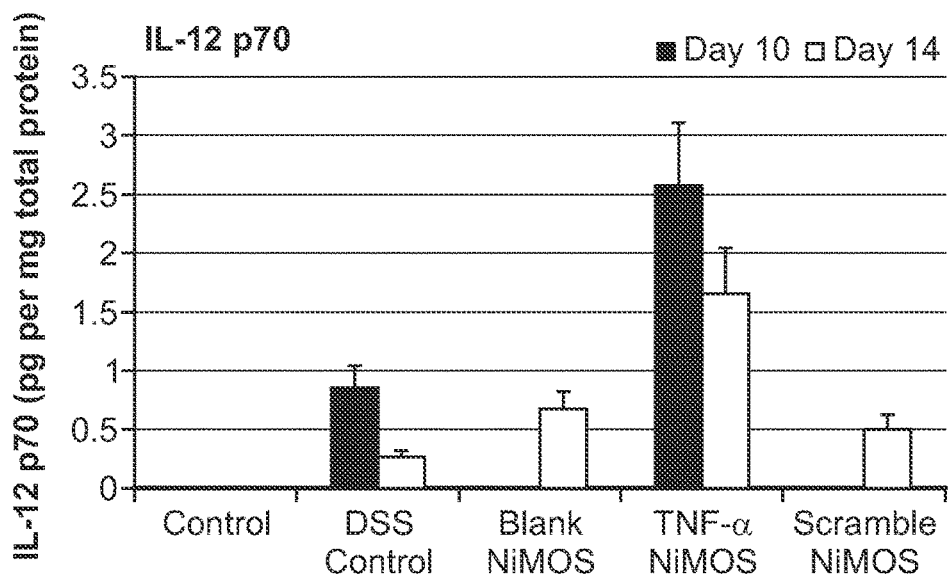
Figure 16H:
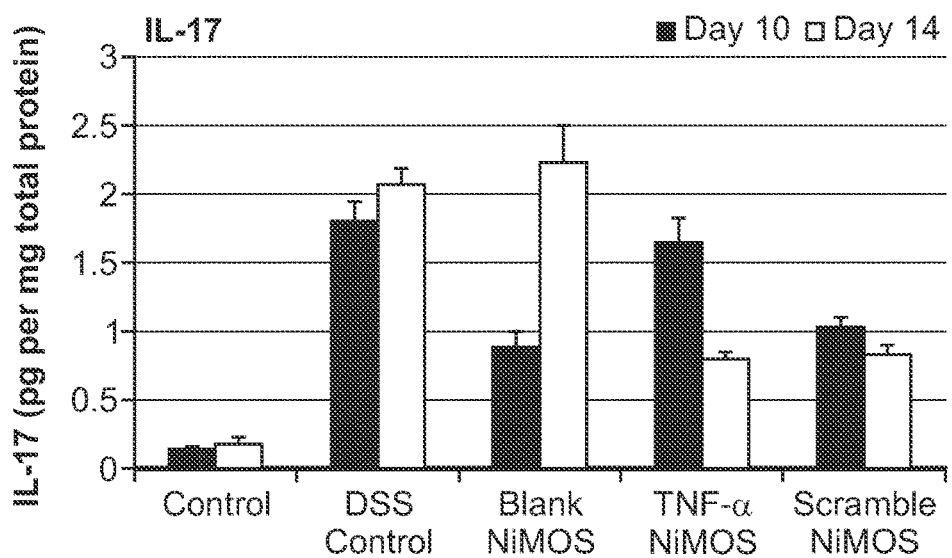
Figure 16I:
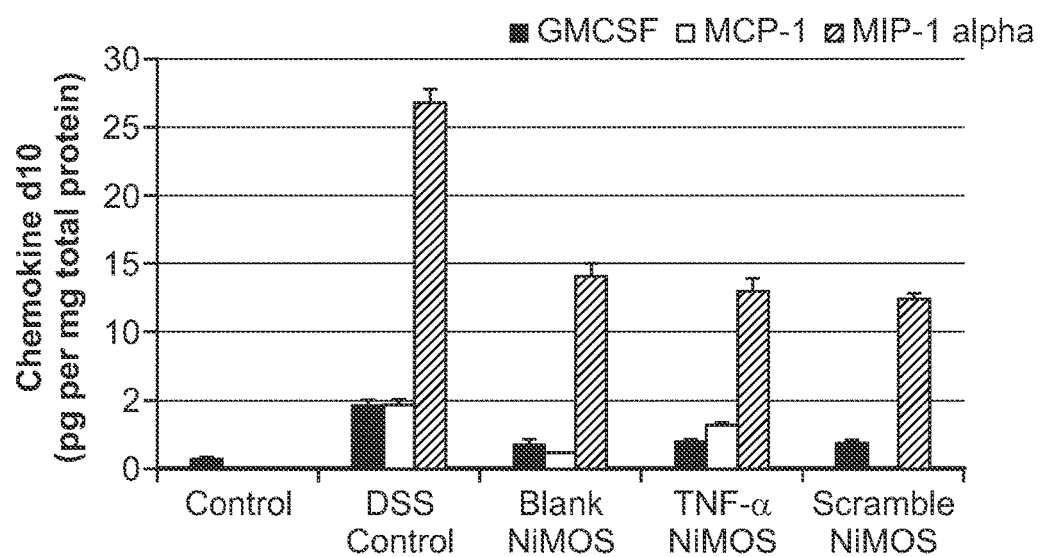
Figure 16K:
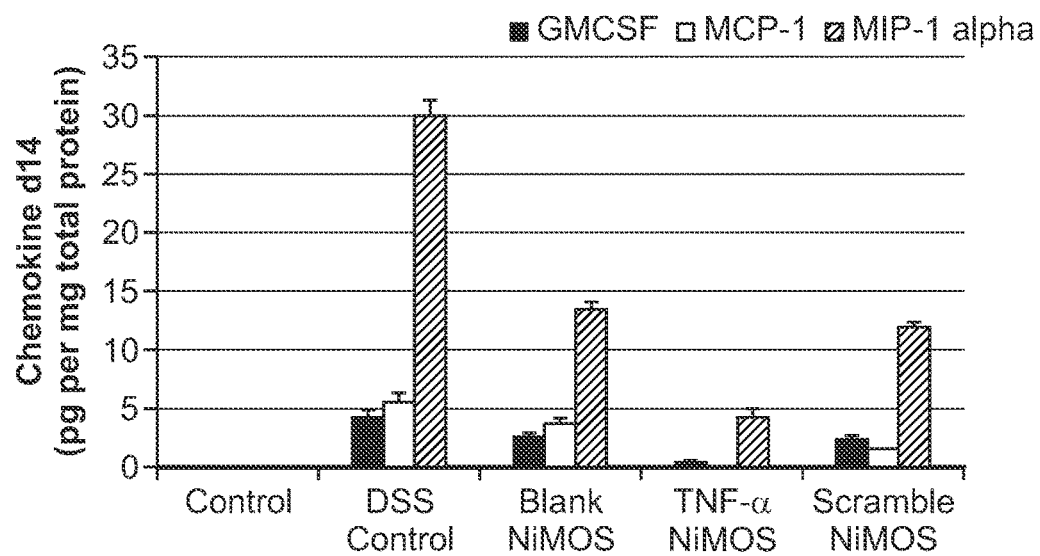

Furthermore, murine TNF-α protein levels were determined using a commercially available ELISA (FIG. 15B). Overall, the group receiving TNF-α NiMOS had the lowest expression levels at both time points with an approximate three-fold decrease on day-14. Protein concentration was the highest on day-10 and 14 in the DSS control group. Here, an approximate 5-fold increase was observed as compared to levels measured in TNF-α NiMOS treated animals.

Pro-Inflammatory Cytokine and Chemokine Profiles

Expression profiles of pro-inflammatory cytokines and chemokines upon oral administration of three doses of NiMOS was measured by ELISA (FIG. 16). Overall, pro-inflammatory cytokines were the lowest in the healthy group (control) that was not exposed to DSS. Therefore, no colitis was induced and no features of inflammation were exhibited. Expression of interleukin (IL)-1α and IL-1β was upregulated on day-10 in the DSS control group reaching values of 135 and 57 pg/mg total protein, respectively (FIGS. 16A, 16B). No significant decrease in concentration was observed on day-14. In all other NiMOS groups, less than half the expression levels were detected when compared with the blank NiMOS treatment group for IL-1α on day-10. However, on day-14, concentrations of IL-1α and IL-1β were lowest in the TNF-α NiMOS group in contrast to all other colitis groups showing more than 5- and 3-fold down-regulation compared to the DSS control with no significant difference in remaining groups. Of all the colitis-bearing animals tested in the study, the lowest concentrations of IL-1, IFN-γ, IL-5, IL-6, IL-12 p70, and IL-17 (FIGS. 16C-16H) were measured in the scramble NiMOS group on day 10, while IL-12p70 levels were the highest in the TNF-α NiMOS group. The DSS control had the highest expression levels for the remaining cytokines. As observed in IL-1α and β, levels of the pro-inflammatory cytokines mentioned above were significantly lower in TNF-α NiMOS mice than in the colitis control group and treatment groups on day-14. On day 10 of the study, levels of granulocyte macrophage colony-stimulating factor (GMCSF) and monocyte inflammatory protein (MIP)-1α did not show any significant variations in all three NiMOS groups; levels were about 1.8 pg/mg and 13 pg/mg total protein, respectively, while the remaining colitis group reached concentrations of about 2.5 fold of these values (FIG. 16I). It should be noted, that the normal concentration of GMCSF was measured to be 0.65 pg/mg total protein, while MIP-1α values were below the detection limit of the assay. FIG. 16K shows that both chemokines were significantly decreased on day-14 in the TNF-α NiMOS group, reaching values of 0.45 pg GMCSF and 4.5 pg MIP-1α per mg total protein for all colitis groups. This is equivalent to a 10-fold and more than a 6-fold decrease of the chemokines as compared to the colitis group and a 6-fold and 3-fold decrease compared to the blank and scramble NiMOS, respectively. Blank and scramble NiMOS exhibited similar levels of these two chemokines, with values of about 2.7 pg GMCSF and 13 pg MIP-1α per mg total protein. A similar result was observed for monocyte chemotactic protein (MCP)-1 for day-14.

Colonic Tissue Histopathology

Figure 17:
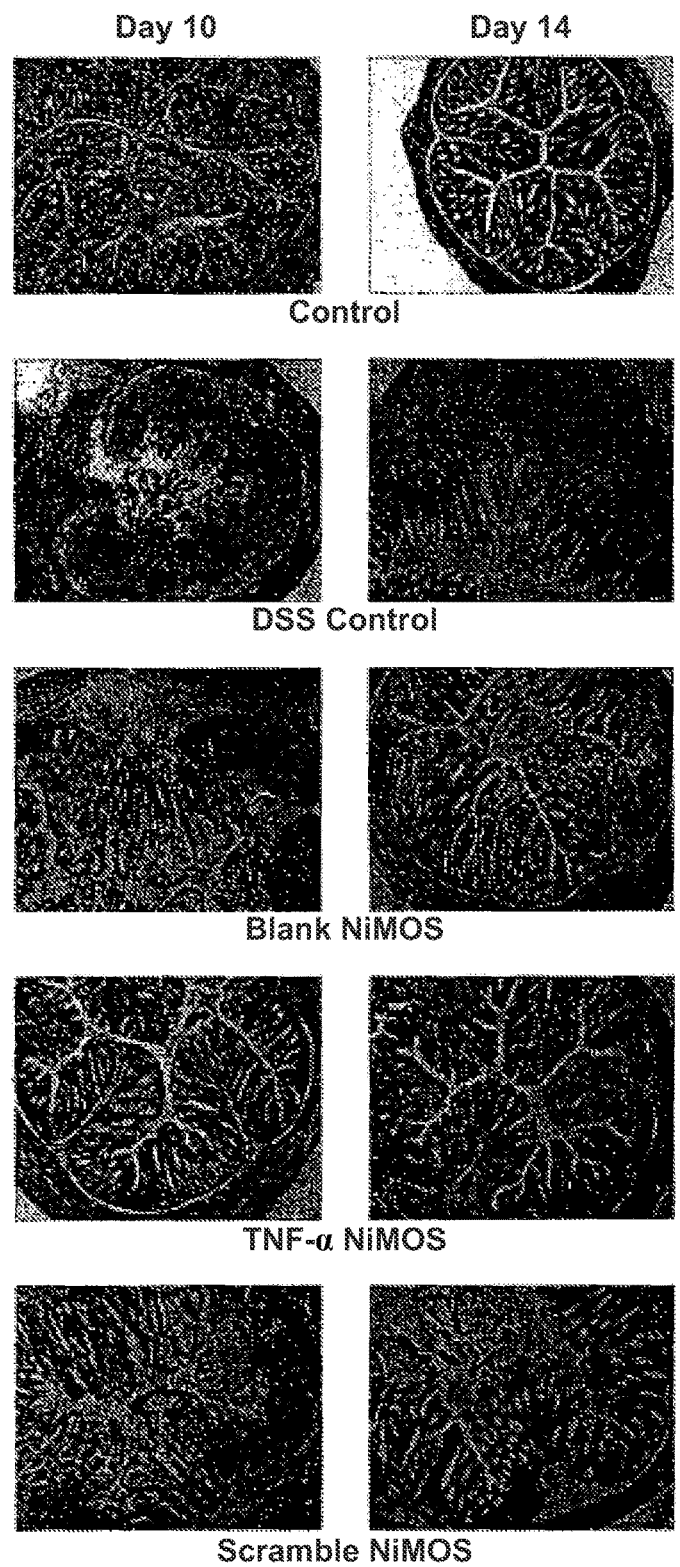
FIG. 17: Evaluation of colonic tissue histopathology. Images of the stained sections of the colon harvested from each group at days post-administration. Images of tissue cryosections obtained on day 10 and day 14 of the study are shown at magnifications of 10× and 40× of the original size. Sections from the control group show normal and healthy colon tissue. Intestinal tissues from the dextran sulfate sodium (DSS) control group, the group treated with blank NiMOS as well as NiMOS encapsulating scrambled TNF-α siRNA sequence showed a significant level of infiltration of white blood cells, abnormal mucosal architecture and a certain degree of goblet cell depletion. Tissue from the group receiving TNF-α silencing NiMOS exhibited a tissue structure more closely resembling that of healthy tissue.

H&E stained cryosections from the large intestine were evaluated for changes occurring at the histological level upon induction of acute colitis and treatment of inflammation with TNF-α NiMOS (FIG. 17). Tissue from the control group had normal colon histology bearing no signs of inflammation or disruption of healthy tissue morphology, serving as the baseline for comparison to the remaining samples. In contrast, intestinal tissue from the DSS control, the group receiving blank NiMOS, and scramble NiMOS group exhibited clear signs of inflammation including cell infiltration, goblet cell depletion, and irregular mucosal structure as described before, which did not substantially subside as the study progressed. On the other hand, tissue from the TNF-α NiMOS group showed a considerable decrease in the level of inflammation and exhibited a morphological tissue structure resembling that of healthy baseline tissue presenting signs of epithelial regeneration.

Therapeutic Efficacy

Figure 18A:
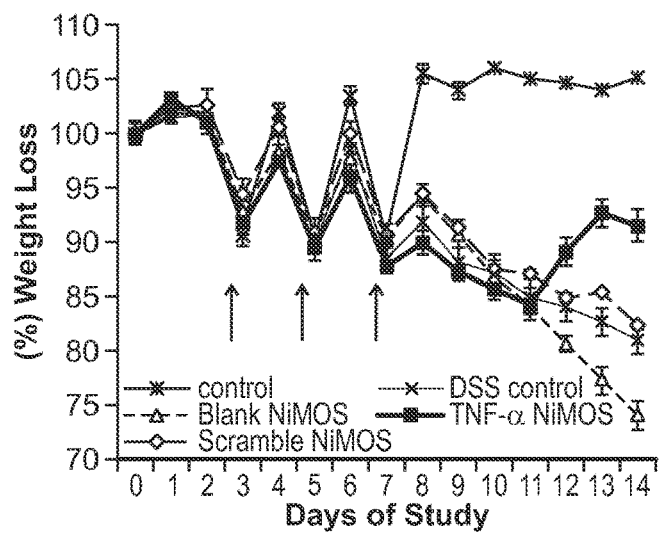
FIG. 18A-C: Macroscopic assessment of therapeutic efficacy. a) Percent change in body weight of Balb/c mice upon continuous exposure to DSS for development of acute colitis model. siRNA containing- and blank NiMOS were administered on day 3, 5, and 7 of the study. Arrows indicate the time points of oral administration of NiMOS. b) Measurement of colon length. c) Tissue myeloperoxidase activity in the large intestine normalized to the total protein content of each sample. Levels represent concentrations obtained from samples on day 10 and 14 of the study (three and seven days post-administration). Values are expressed as mean±S.D. (n=4-8).
Figure 18B:
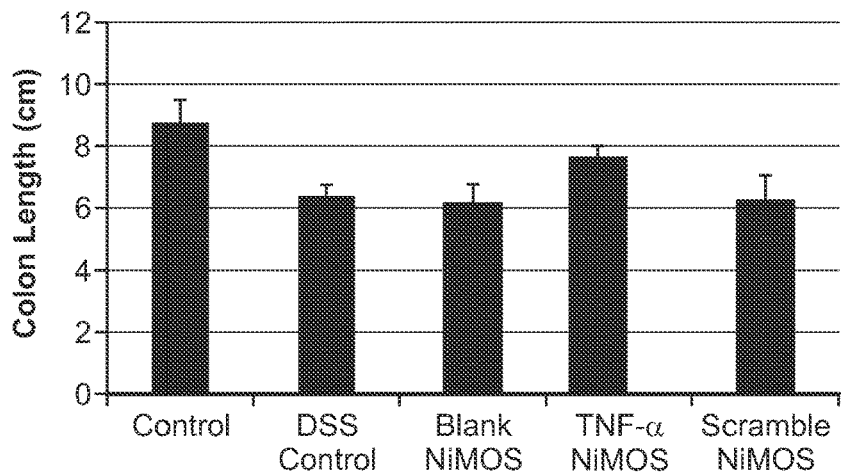

Changes in body weight of colitis-induced mice were evaluated after administration of various treatments in comparison to the control (FIG. 18). On days 2, 4, and 6, mice from all groups were fasted overnight for consistency, as food in the stomach and other sections of the gastrointestinal tract is known to interfere with dosing and analysis upon administration of the formulations. The following morning they were orally administered with blank, TNF-α or scramble NiMOS. Since fasting caused a weight loss of approximately 10% in all groups (FIG. 18A), mice were administered every other day to allow for normalization of body weight to occur. The weight in the control group stabilized after the last administration leveling out at approximately 5% higher than the weight at the beginning of the study. Weight loss for the DSS control, blank and scramble NiMOS animals was quick after the last oral administration with respective values of 19%, 26%, and 18% loss of original body weight on day-14. Of all colitis groups, the smallest weight loss of approximately 8% was observed in the TNF-α NiMOS group. Moreover, general appearance was much closer to a healthy mouse in this group with no severe symptoms of colitis as opposed to the remaining colitis mice described before, which exhibited the classical features associated with acute colitis in a considerable number of animals.

Colon length was assessed and is reported in FIG. 14B. Control mice had a colon length of approximately 8.8 cm. A significant reduction in colon length was observed upon induction of DSS colitis with values of approximately 6 cm. Mice treated with blank and scramble sequence siRNA NiMOS also exhibited shortening of the colon comparable to the colitis control. For the TNF-α NiMOS group, an increase in colon length to almost 8 cm was observed, which was closer to the baseline compared to the remaining colitis groups.

Figure 18C:
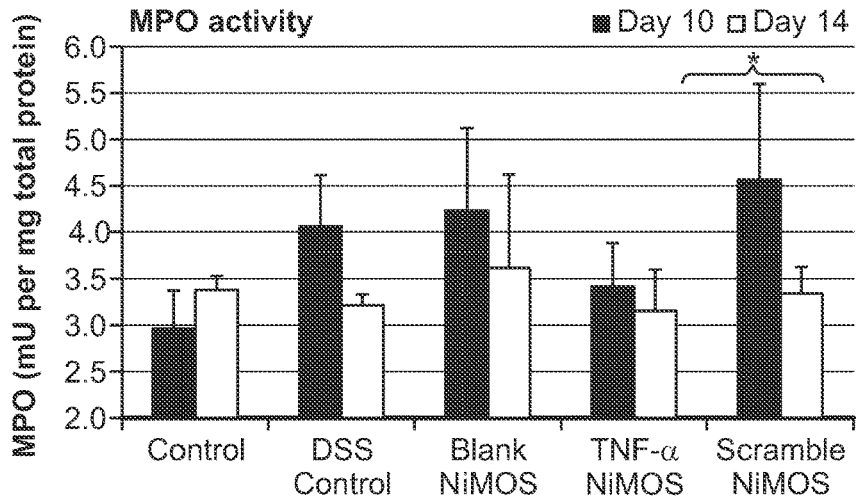

Additionally, the activity of myeloperoxidase was measured as an index marker of inflammation based on the infiltration of activated neutrophils (FIGS. 18C, 14C). Approximately, 4 mU and 3 mU/mg total protein were detected in mice upon induction of DSS colitis on day-10 and 14, respectively, which was comparable to the activity observed in the tissue of blank and scramble NiMOS treated animals. MPO activity was lower in the TNF-α NiMOS group at both time points, reaching values of 3.4 and 3.1 mU/mg total protein, respectively. On day-14, this value was not significantly reduced compared to the activity detected in other colitis mice; however it was slighter lower than the baseline value of the healthy control group. It was found that a higher degree of inflammation was observed in the DSS control, blank and scramble NiMOS groups, with a slightly lower infiltration on day-14.

Result Summary

The instant disclosure uses local IBD treatment that combines positive aspects of RNA interference with the safety of biodegradable polymeric nano- and microparticulate systems enabling a localized treatment through oral administration of siRNA. This option might offer several advantages including lower/fewer doses due to localized therapy and no relative dilution of the agent associated with systemic administration, fewer side effects and higher efficacy.

Disclosed herein is a novel biodegradable and biocompatible polymer-based system, which is applicable to other disease types and models. siRNA encoding for TNF-α was successfully encapsulated, followed by oral administration to DSS-induced colitis mice and evaluated efficiency and feasibility of RNA silencing involved in inflammation. The disease model was chosen because it is one of the most frequently used rodent IBD models. Supplying DSS in the drinking water of animals at libitum provides a predictable onset and course of the disease and lower risk of mortality.

Among the challenges of oral siRNA delivery is ensuring minimal degradation of the payload by gastric and intestinal enzymes, with maximized residence time of particles in the intestine. This allows for sufficient interaction with target cells, aiding in cellular uptake and endosomal release for efficient silencing in the cytosol. To this purpose, NiMOS carrying the hydrophilic labile payload in the innermost nanoparticulate phase were developed. Such systems are capable of release over time of the payload by a controlled degradation of the outer layer.

This platform has been shown to encapsulate plasmid DNA efficiently, enable intracellular uptake, and nuclear transport while being safe and efficient for gene transfection; and it can easily be adapted for encapsulation of siRNA. Furthermore, type B gelatin was selected for the nanoparticle formulation because it can physically entrap pDNA and siRNA, protecting the payload during intracellular transport; whereas other, more common systems rely on surface adsorption or electrostatic complexation to carry siRNA.

The results show that NiMOS can effectively protect the siRNA encapsulated within the nanoparticles inside PCL microspheres from the gastrointestinal barriers and degrading proteolytic enzymes; and release is expected to occur in the intestines at the site of inflammation. Furthermore, the microspheres with sizes smaller than 5 μm promote localization in the intestine by delivery of gelatin nanoparticles to the enterocytes and other cells at these sites once the PCL matrix is degraded by lipases abundantly present in the intestinal tract allowing for endocytosis. As such, this is an effective system for siRNA encapsulation and delivery.

In the TNF-α NiMOS group, the analysis of real time PCR of both time points showed very low levels of murine TNF-α, which was similar to the level observed in healthy, control mice on day-10. This is attributed to the silencing effect of NiMOS, which was not observed in remaining colitis-bearing groups. The relative decrease in expression of TNF-α mRNA in all NiMOS groups on day-14 can potentially be attributed to a complex interplay of pro-and anti-inflammatory cytokines resulting in compensatory responses due to induction of colitis. ELISA results were in good correlation with real time-PCR analysis. Lower levels of TNF-α were observed in TNF-α NiMOS animals as compared to the remaining colitis-bearing groups at both time points and most cytokines on day-14 clearly indicating the high potential of TNF-α siRNA NiMOS for oral administration and RNA silencing, while elevated levels of pro-inflammatory cytokines where detected in blank and scramble NiMOS groups. Lower expression of many cytokines due to down-regulation of TNF-α could result in alleviation of inflammation at the disease site. This was also reflected in the smaller degree of weight loss and in colon tissue morphology which showed signs of regeneration with only few abnormalities. However, shortly after administration of all three NiMOS doses, down-regulation of the cytokines was not as pronounced in the TNF-α group, and expression levels were slightly higher as compared to remaining NiMOS-treated control mice. This effect could be attributed to the specificity of the TNF-α siRNA, which resulted in silencing of TNF-α and had no immediate effect on other markers after a short time. Also, lower expression of TNF-α due to silencing in this group preceded the down-regulation of other pro-inflammatory cytokines. Moreover, a reduction of expression on day-14 was seen in certain chemokines such as GMCSF, MIP-1α, and MCP-1, which are markers regulating cell infiltration at disease sites, thus directly contributing to inflammatory responses. For example, systemic administration of MIP-1α has been shown to considerably aggravate colitis in mouse models. Thus, lower expression levels of MIP-1α as observed in TNF-α NiMOS groups indicates a decrease in severity of the disease suggesting the therapeutic efficacy of the TNF-α silencing treatment.

Example 5

Non-Viral Gene Delivery Systems

When encapsulated in the innermost phase of a multiple emulsion, a gelatin, non-condensing polymer can bring about efficient gene transfection. Evaluations of green fluorescent protein expressing plasmid DNA (EGFP-N1) transfection efficiency were carried out murine adherent alveolar macrophages J77A.1.

1. Preparation and Characterization of Gelatin Nanoparticles-in-Emulsion (NiE) Formulations Preparation and Characterization of Gelatin Nanoparticles:

Gelatin nanoparticles (GNP) were prepared by a solvent displacement method. Briefly, 100 mg of type B gelatin bloom strength 225 (Sigma Aldrich) was dissolved in 10 ml of water at 37° C. After this step, the pH was adjusted to 7 using 0.2 M NaOH solution. Gelatin particles were precipitated from the aqueous solution using ethanol as an anti-solvent. The final ratio of ethanol water was optimized to 4:1. Prior to its addition to gelatin solution, the temperature of ethanol solution was brought down to −40° C. in order to enhance the anti-solvent effect.

Enhanced green fluorescent protein (EGFP) expressing plasmid DNA (EGFP-N1) was added at concentration of 1% w/w of solubilized gelatin. Alternatively, for cell uptake studies rhodamine-conjugated dextran (Mol. wt. 70 kDa) was added at final concentration of 0.5% w/w of gelatin to gelatin solution after pH adjustment for its physical encapsulation. The precipitated particles were centrifuged at 35,000 rpm for 45 minutes using a Beckman ultracentrifuge. The nanoparticle pellet was collected, washed with deionized water, flash frozen in liquid nitrogen, and lyophilized for 24 hours to give a dry powder.

Formulation of Nanoparticles-in-Emulsion (NiE) Formulation:

Water-in-oil-in-water (W/O/W) multiple emulsions are triphasic systems composed of three phases, inner aqueous droplets contained in oil globules surrounded by outer aqueous phase. The W/O/W multiple emulsion was formulated by a two step emulsification method. Extra pure safflower oil (Jedwards, Inc., Quincy, Mass.), which is rich in omega-3 and omega-6 polyunsaturated fatty acids, was used for the oil phase of the emulsion. Safflower oil contains high levels of tocopherols, which are reported to have a negative effect on levels of pro-inflammatory cytokines tumor necrosis factor alpha and interleukin 1 beta. Also, tocopherols have been shown to exert antioxidant activity and may provide protection against acute inflammation mediated by reactive oxygen species.

The first step consisted of the formulation of W/O primary emulsion using an oil soluble surfactant, Span® 80. Naked plasmid (ME) or plasmid encapsulated in the gelatin nanoparticles (NiE) was incorporated in the aqueous phase of the primary emulsion to a final concentration of 50 µg/ml of the W/O/W multiple emulsion. The appropriate amounts of each ingredient in the optimized formulations are listed in Table 7.

A stable primary W/O emulsion with encapsulated naked plasmid DNA or as dispersion with DNA-encapsulated nanoparticles was formed using the Silverson homogenizer L4RT at the speed of 9,000 rpm for 15 minutes. The primary emulsion of dispersion was mixed with additional aqueous phase consisting of a water soluble surfactant Tween® 80 and the formulation was prepared by homogenization at 4,000 rpm for 4 minutes. Increasing the speed to greater than 4,000 rpm in this step resulted in rupture of the multiple emulsion globules.

TABLE 7

The Composition of the Optimized Primary and Multiple Emulsion or Dispersion Formulations Composition of W/O/W

| Step 1 - Primary Emulsion | |
|---|---|
| Safflower Oil | 1.6 ml |
| Span 80 | 20% |
| Water | 2 ml |
| Step 2 - Multiple Emulsion | |
| W/O emulsion from Step 1 | 4 ml |
| Tween 80 | 0.25% |
| Water | 4 ml |

The control and plasmid DNA encapsulated nanoparticle size and surface charge (zeta potential) values were measured using a Malvern's Zetasizer® either before or after ultracentrifugation. The results shown in Table 8 show that the particle size was in the range of 160 nm to 170 nm in diameter and the zeta potential values negative. As the isoelectric point of type B gelatin is in the range of 4.5 to 5.5, the formed nanoparticles will have a net negative charge at pH 7.4. Plasmid DNA is physically encapsulated in a hydrogel type matrix of type B gelatin biopolymer in contrast to electrostatic condensation by positively charged lipids and polymers.

TABLE 8

Particle size and surface charge values of blank and plasmid DNA-encapsulated type B gelatin nanoparticles

| Formulation | Particle Size (nm) | Zeta Potential (mV) |
|---|---|---|
| Blank Gelatin Particles | 164.3 ± 5.0* | −10.7 ± 0.12 |
| EGFP-N1 Plasmid-Containing Nanoparticles | 166.0 ± 5.6 | −11.2 ± 1.35 |

*Mean ± standard deviation (n = 3)

Stability of the nanoparticles-in-emulsion (NiE) tri-phasic system was evaluated using accelerated centrifugation and evaluation of phase separation under different conditions. When the multiple emulsion or NiE was centrifuged at up to 4,000 rpm for 1 hour, there was no phase separation observed under microscopic evaluations. In addition, the effect of up to 1,000 fold dilution in aqueous media on the leaching and release by fluorescence microscopy of rhodamine-labeled dextran either when administered directly into the W/O primary emulsion or upon nanoparticle-encapsulation was examined.

Figure 19:
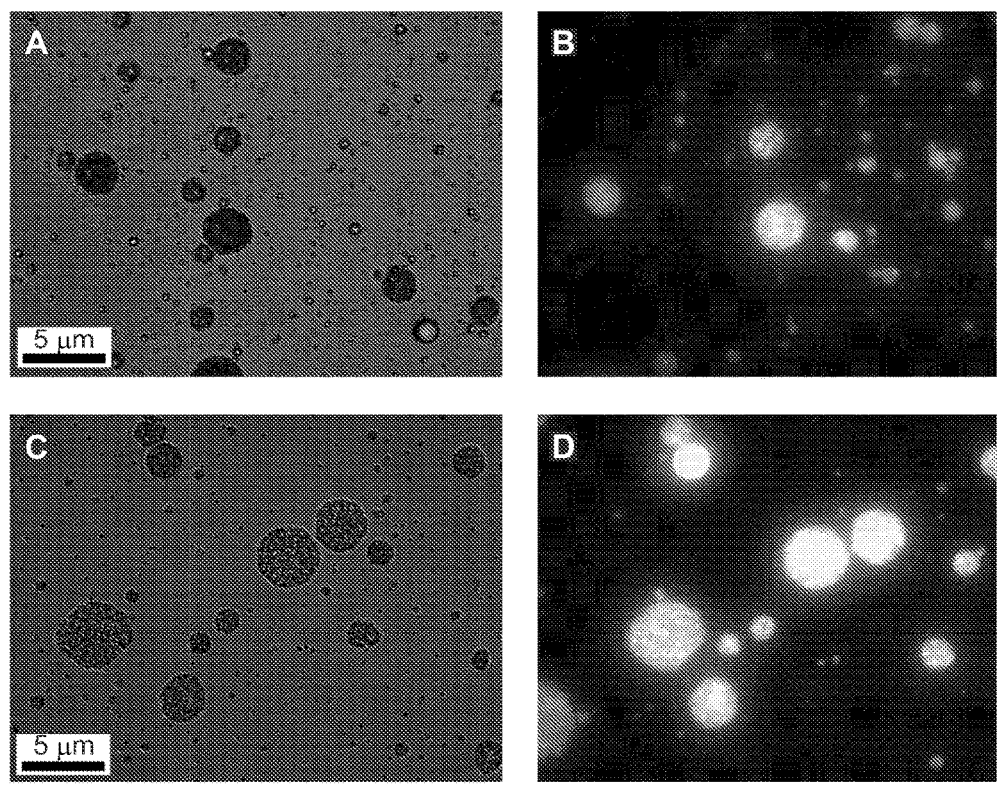
FIG. 19: Bright-field and fluorescent microscopy images of NiE (A&B) and ME (C&D) showing stable non-leaky multiple emulsion globules of 5.0 um or less diameter. Original magnification was 60×.

The results of preliminary stability studies showed that the both W/O/W and NiE formulations did not phase separate upon storage and even after accelerated centrifugation cycle. In addition, as shown in FIG. 19, the internalized rhodamine-dextran in the inner aqueous phase or when encapsulated in gelatin nanoparticles did not release their content in the external aqueous phase even after 7 days of incubation at 4° C.

2. Plasmid DNA Encapsulation and Stability Studies

Plasmid DNA Loading Studies:

Loading efficiency of pEGFP-N1 in NiE, ME and GNP formulations was evaluated by using Quant-iT™ PicoGreen® dsDNA Reagent (Invitrogen, Carlsbad, Calif.). PicoGreen® dsDNA Reagent is a highly sensitive fluorescent stain for quantification of double stranded DNA. For this purpose NiE and ME were loaded with pEGFP-N1 at final concentration of 50 µg/ml in the internal phase of multiple emulsion. GNPs were loaded with 1% w/w of pEGFP-N1, 40 mg of which were incorporated in the internal phase of the multiple emulsion. Extraction of encapsulated pEGFP-N1 from lyophilized GNP was carried out by incubating 1 mg of gelatin particles with 1 ml of PBS containing 0.2 mg/ml protease for 30 minutes at 37° C. For ME formulation, pEGFP-N1 was extracted by first destabilizing emulsion by addition of $\frac{1}{10}^{th}$ volume of 5M NaCl followed by centrifugation at 20,000 rpm for 30 minutes.

After this process, the oil and water layers became separated in to two distinct layers. After discarding the oily layer, the aqueous layer was diluted 200 times to concentration of 2 µg/ml with PBS. Ten µl of this diluted solution was used for estimation of DNA loading. In case of NiE 1 ml of emulsion was de-stabilized with 100 µl of 5M NaCl and centrifuged at 20,000 rpm for 30 minutes. The GNP palette obtained was treated with 5 ml of protease buffer for 30 minutes at 37° C. for release of EGFP-N1 plasmid DNA from the particles. Blank gelatin particles and emulsions with blank inner aqueous phase or blank gelatin particles in the inner aqueous phase were used as controls after same extraction treatment as plasmid loaded formulations was performed.

To obtain a calibration curve, different known standard concentrations of EGFP-N1 plasmid DNA in PBS were prepared. One hundred µl of PicoGreen® assay reagent was added to the wells of a 96 well plate, followed by addition of 100 µl of either standard, sample or control solution. The 96 well plate was incubated for 5 minutes protected from light at room temperature and then fluorescence intensity was measured at 480 nm excitation wavelength and 520 emission wavelength using Bio-Tek (Winooski, Vt.) Synergy® HT microplate reader with KC4 software.

Stability of EGFP-N1 Plasmid DNA:

A gel retardation assay was performed to evaluate stability of plasmid DNA encapsulated in NiE, ME and GNP to ensure physical and chemical stability of plasmid DNA during the process of formulation. For this purpose E-Gel® 1.2% with SYBR Safe™ (Invitrogen, Carlsbad, Calif.) were used. SYBR safe DNA stain has an advantage that it is safer compared to ethidium bromide which can cause mutations and chromosomal transformations. Agarose gel electrophoresis involves movement of DNA through agarose gel under influence of electric field in which negatively charged DNA moves towards positive end through the gel. In this process larger sized DNA fragments move slower compared to smaller sized DNA fragments through the agarose gel. This results in size dependent separation of DNA over time as it travels through the gel. Bands formed after the process of electrophoresis can be visualized under blue light UV transluminescence.

During the process of emulsification if the plasmid DNA had broken into fragments multiple bands would be observed on an agarose gel. Alternatively if the plasmid DNA was stable in its supercoiled form during formulation process, a single band of plasmid DNA would be observed. To determine the size of Plasmid DNA a super coiled DNA ladder (Invitrogen, Carlsbad, Calif.) was used. Three formulations containing pEGFP-N1 under this study—NiE, ME and GNP were tested for plasmid EGFP-N1 stability. EGFP-N1 plasmid DNA was extracted from NiE, ME and GNP formulations as mentioned above and loaded at concentration of 100 ng in 20 µl of loading buffer per well of 1.2% E-Gel Cassette® (Invitrogen, Carlsbad, Calif.).

EGFP-N1 plasmid DNA loading efficiency was calculated as percentage of plasmid loaded compared to plasmid added initially. Results shown in Table 9 show that plasmid loading efficiency was increased, when plasmid was protected by encapsulation in GNP in NiE formulation compared to ME formulation in which unprotected naked plasmid was present in the internal phase of ME. Later a separate group of blank emulsion formulations were terminally spiked with EGFP-N1 plasmid DNA after completion of both steps of emulsification process. Then similar plasmid extraction procedure was carried out. Amount of plasmid assayed from these experiments was found to be 99.16%±0.35 of that added terminally. This result indicated that decrease in plasmid loading efficiency was might be due to high shear homogenization process.

TABLE 9

Plasmid DNA encapsulation efficiency in type B gelatin particles and in nanoparticles-in-emulsion formulations

| Formulation | DNA Loading Efficiency (%) |
|---|---|
| Naked plasmid in W/O/W multiple emulsion | 54.4 ± 3.0 |
| Plasmid encapsulated in type B gelatin nanoparticles | 99.0 ± 0.5 |
| Plasmid encapsulated in gelatin nanoparticles-in-emulsion | 70.3 ± 2.2* |

*Mean ± S.E (n = 3)

For analysis for plasmid DNA stability, agarose gel electrophoresis was used. As shown in FIG. 20, a single band of pEGFP-N1 of 4.7 kb size was observed for all three formulations indicating that EGFP-N1 plasmid DNA retained its stability throughout the formulation process. Wells loaded with control formulations did not show any band.

3. Cellular Uptake and Intracellular Trafficking Studies

Cell Culture Conditions:

Adherent murine alveolar macrophages J774A.1 cells (ATTC, Rockville, Md.), were cultured in T75 culture flasks using Dulbecco's Modified Eagle Medium (DMEM) supplemented with fetal bovine serum and penicillin/streptomycin antibiotics. Cells were allowed to divide until they reached desired density. Cell count was estimated by placing 20 µl of the cell suspension mixture on a heamocytometer slide. Cell viability studies were performed using Trypan blue dye exclusion assay.

Cellular Uptake and Localization Studies:

To evaluate NiE and ME uptake in macrophages and intracellular localization, rhodamine-dextran (Mol. wt. 70 kDa) was encapsulated in the internal aqueous phase of the primary W/O emulsion or in the gelatin nanoparticles prior to formulating into the multiple emulsions. The final concentration of rhodamine-dextran incorporated in both the formulations was 0.0025% (w/v). In case of NiE 40 mg of 0.5% (w/w) rhodamine-dextran encapsulated gelatin particles were added to internal phase of multiple emulsion, while in case of ME formulation 8 µl of 25 mg/ml solution of Rhodamine dextran was incorporated to the internal phase of multiple emulsion.

Approximately 200,000 cells were plated in each well of a six-well plate containing alcohol-sterilized glass cover slip and allowed to adhere for 12 hours prior to treatment with control and test formulations. The cells were fed with multiple emulsions containing 0.0025% (w/v) rhodamine-dextran either solubilized in the inner aqueous phase or encapsulated in gelatin particles which were then added to the internal aqueous phase of W/O/W emulsion. Multiple emulsions prepared with blank aqueous phase or with blank gelatin nanoparticles were used as controls. After 60 minutes, 90 minutes, and 120 minutes following incubation with the control and test formulations, the cells were washed with sterile phosphate buffered saline (PBS, pH 7.4) and the cover slip was removed from the wells and mounted on a clean glass slide. The samples were observed with an Olympus fluorescence microscope equipped with a BioQuant image analysis system.

Intracellular DNA Trafficking Studies:

In order to understand cellular uptake and intracellular transport of plasmid EGFP-N1 containing NiE formulation, DNA trafficking studies were performed. Towards this end, NiE was labeled using a fluorescent dye Rhodamine B isothiocyanate (St. Louis, Mo.) which was covalently conjugated to GNP at concentration of 0.5% w/w, resulting in final dye concentration of 0.0025% w/v in NiE. DNA was labeled using PicoGreen® reagent (Invitrogen, Carlsbad, Calif.). The nuclei of the cells were stained using Hoechst® 33245 dye (Invitrogen, Carlsbad, Calif.). Approximately 200,000 J774A.1 macrophage cells were plated in a six well plate and treated with fluorescently labeled NiE formulation. After incubation of cells with NiE formulation for 1, 2, 4 and 6 hours, images were acquired using a Nikon Eclipse® TE 200 microscope having mercury arc lamp for visualizing blue, red and green fluorescence at excitation/emission wavelength of 460/50 nm, 515/30 nm and 560/55 nm. Based on different fluorescent signals emitted by NiE, plasmid EGFP-N1 and nuclei of cells, localization of NiE and plasmid EGFP-N1 relative to nuclei of cells was visualized. Similar studies were performed using rhodamine conjugated GNP alone and ME containing rhodamine-labeled dextran (Mol. wt. 70,000) dissolved in the innermost aqueous phase of the multiple emulsion.

Figure 21:
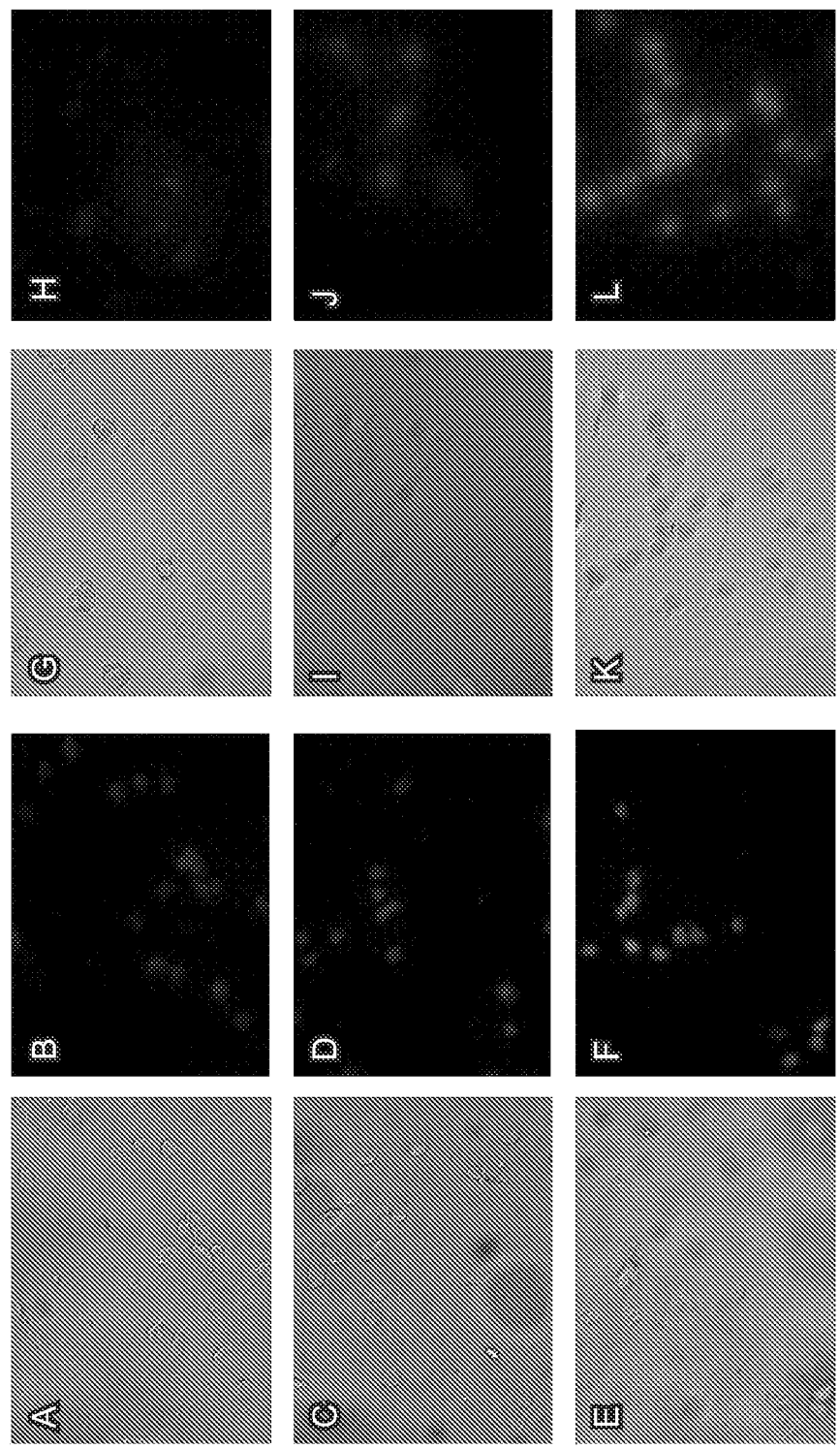
FIG. 21: Bright-field and fluorescent images in figure (A,B), (C,D) and (E,F) shows cellular uptake of Rhodamine dextran containing ME formulation by J774A.1 cells at 60 minutes, 90 minutes and 120 minutes time points respectively. Bright field and fluorescent images in figure (G,H), (I,J) and (K,L) shows cellular uptake of Rhodamine dextran (70,000 MW) containing NiE formulation by J774A.1 cells at 60 minutes, 90 minutes and 120 minutes time points respectively. Original magnification was 40×.

The microscopy images in FIG. 21 shows that that the rhodamine-dextran containing W/O/W emulsion and NiE formulations were rapidly internalized in murine alveolar macrophages J774A.1 cells. As time progressed, an increase in fluorescence intensity was observed, which became maximum after 120 minutes of exposure.

Figure 22:
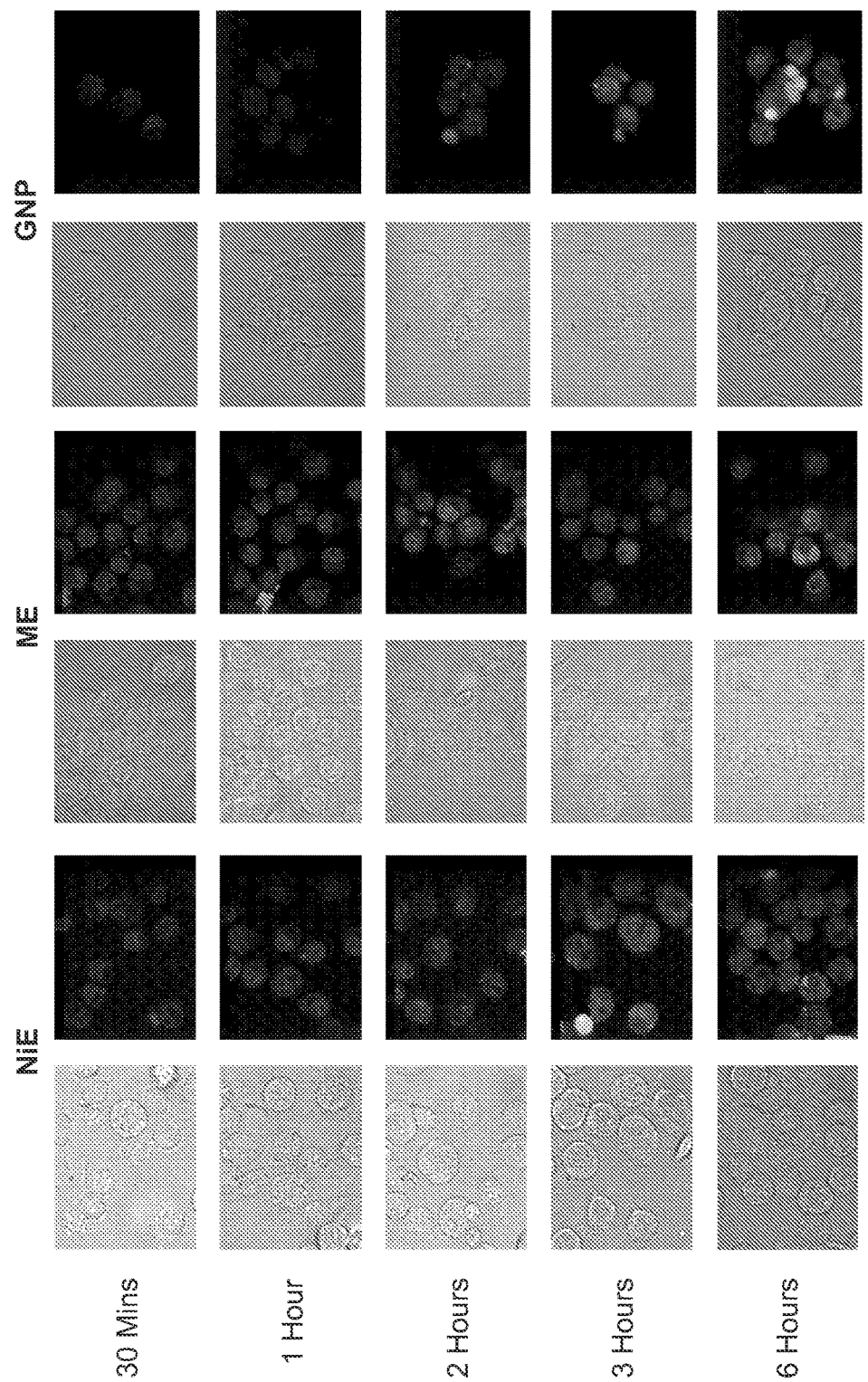
FIG. 22: Fluorescent microscopy images showing localization of DNA (green), GNP (red) and Nucleus (blue) within J774A.1 cells at 30 minutes, 2 hours and 6 hours time points post-treatment with either NiE, ME or GNP formulations. Original magnification was 60×.
Figure 23A:
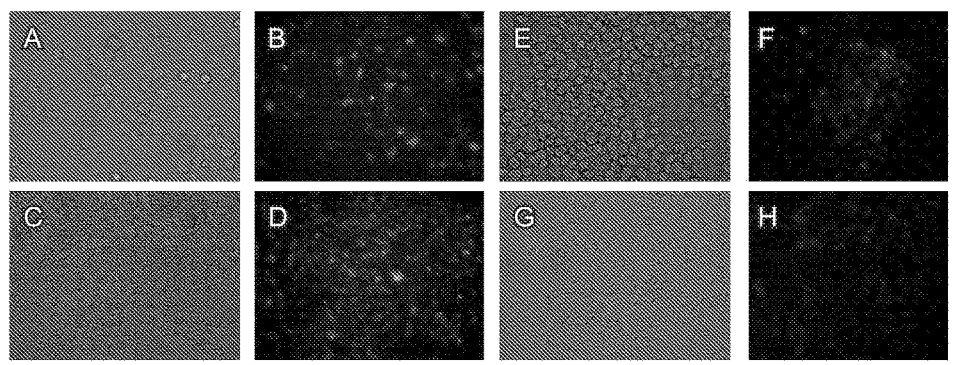
FIG. 23A-F: Evaluation of qualitative gene transfection by fluorescent microscopy: (a) Differential interference contrast and fluorescent microscopy images showing green fluorescent protein expression of in J774A.1 cells 24 hour post-treatment with EGFP-N1 plasmid DNA complexed with Lipofectin® (A,B), or encapsulated in NiE (C,D), ME (E,F) and GNP (G,H). Original magnification was 40×; (b): Differential interference contrast and fluorescent microscopy images showing green fluorescent protein expression of in J774A.1 cells 48 hours post-treatment with EGFP-N1 plasmid DNA complexed with Lipofectin® (A,B), or encapsulated in NiE (C,D), ME (E,F) and GNP (G,H). Original magnification was 40×; (c): Differential interference contrast and fluorescent microscopy images showing green fluorescent protein expression of in J774A.1 cells 72 hours post-treatment with EGFP-N1 plasmid DNA complexed with Lipofectin® (A,B), or encapsulated in NiE (C,D), ME (E,F) and GNP (G,H). Original magnification was 40×; (d): Differential interference contrast and fluorescent microscopy images showing green fluorescent protein expression of in J774A.1 cells 96 hours post-treatment with EGFP-N1 plasmid DNA complexed with Lipofectin® (A,B), or encapsulated in NiE (C,D), ME (E,F) and GNP (G,H). Original magnification was 40×; (e): Differential interference contrast and fluorescent microscopy images showing green fluorescent protein expression of in J774A.1 cells 120 hours post-treatment with EGFP-N1 plasmid DNA complexed with Lipofectin® (A,B), or encapsulated in NiE (C,D), ME (E,F) and GNP (G,H). Original magnification was 40×; (f): Differential interference contrast and fluorescent microscopy images showing green fluorescent protein expression of in J774A.1 cells 144 hours post-treatment with EGFP-N1 plasmid DNA complexed with Lipofectin® (A,B), or encapsulated in NiE (C,D), ME (E,F) and GNP (G,H). Original magnification was 40×
Figure 23B:
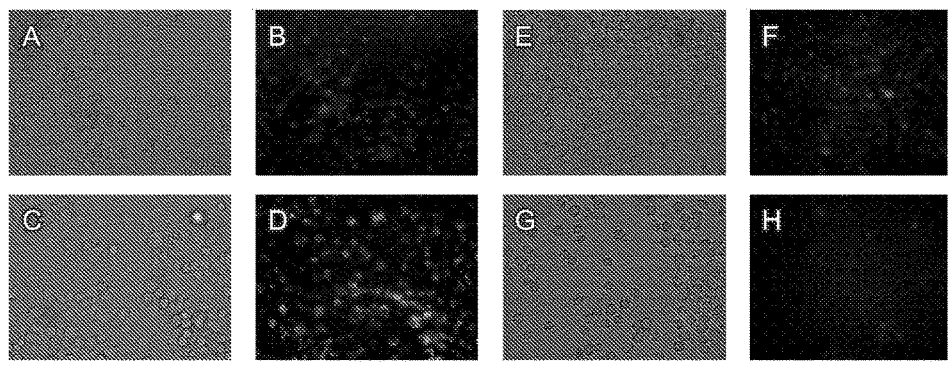
Figure 23C:
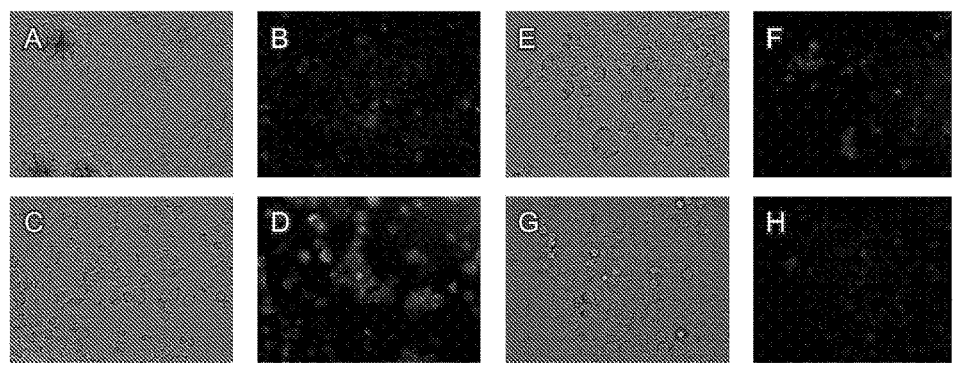
Figure 23D:
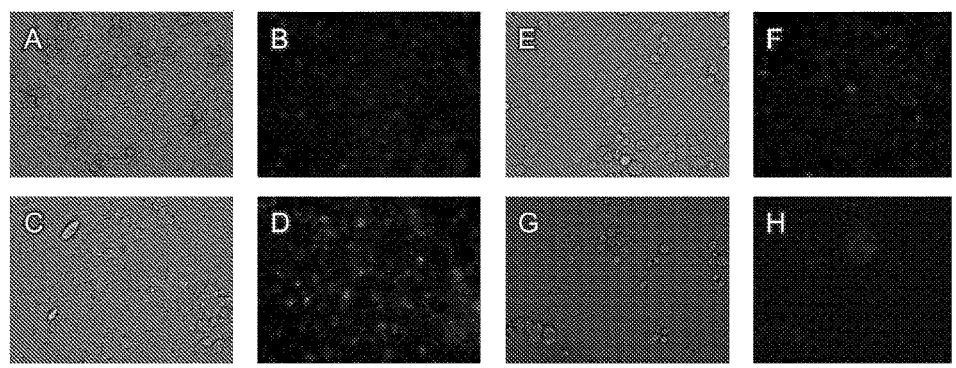
Figure 23E:
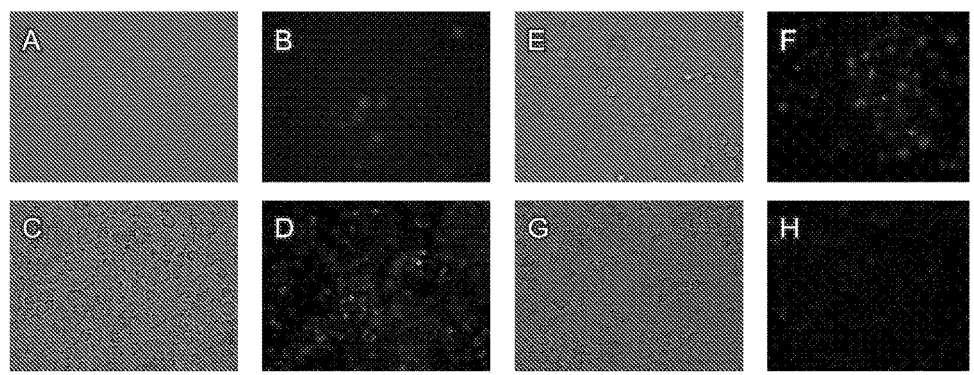
Figure 23F:
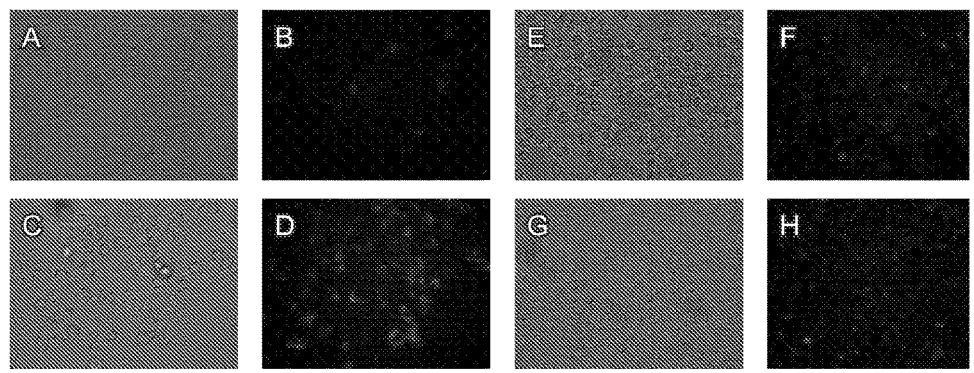

DNA trafficking studies were also performed in order to assess ability of different formulations for delivery of DNA within the nuclei of the cells. Results of these studies are shown in FIG. 22. Cellular internalization of GNP, ME and NiE was observed starting 30 minute time point post formulation treatment. At the initial 30 minute time point, particles were further away from cell nuclei. Starting from 2 and 4 hour time point post treatment with different formulations, the distance between particles and nuclei was reduced and also co localization of green and blue colors was observed. This indicated that DNA delivered through GNP, ME or NiE formulations was able to reach the nuclear compartment of the cell within two to four hours of formulation incubation. Along with increase in intracellular uptake of formulations with time, an increase in nuclear co-localization of DNA with time was also observed indicating particle movement from periphery towards cell nucleus. At 6 hour time-point, the red color was localized near the perinuclear space, while green color was largely co-localized with blue color. These results indicate that GNP, ME and NiE were capable of delivering DNA within nuclear compartment of the cells.

4. Reporter GFP Gene Transfection Studies

Qualitative Gene Transfection Studies:

To determine whether the above formulations were capable of causing gene transfection in murine alveolar macrophage cell lines, gene transfection studies were carried out. For this purpose, plasmid EGFP-N1, a reporter plasmid which expressed enhanced green fluorescent protein (EGFP) was used. Gene transfection studies were carried out for NiE, ME and GNP formulations. EGFP-N1 plasmid DNA was incorporated at final concentration of 50 µg/ml in to NiE and ME. In the case of NiE, 40 mgs of gelatin particles loaded with 1% (w/w) of EGFP-N1 plasmid was added to the inner aqueous phase of the W/O/W multiple emulsion while in case of ME 400 µl of 1 mg/ml solution of EGFP-N1 was incorporated in the innermost aqueous phase of the multiple emulsion. Transfection of EGFP-N1 plasmid DNA with Lipofectin®, a commercially available positively charged lipid transfection reagent was used as positive control. Cells treated with blank formulations were used as negative controls. Alcohol sterilized cover slips were placed in each well of a six well plate. Approximately 200,000 adherent alveolar macrophage cells were inoculated in each well of a six well plate using DMEM modified with 10% FBS and 5% penicillin streptomycin and allowed to adhere to cover slip over a period of 12 hours. After this period serum containing medium was replaced with formulation containing serum fee medium followed by incubation at 37° C. for 6 hours in order to allow sufficient uptake of formulation by the cells. After 6 hours formulation containing medium was replaced with DMEM modified with 10% FBS and 5% penicillin-streptomycin antibiotic. The samples were observed with an Olympus fluorescence microscope equipped with a BioQuant image analysis system at day 1 day through day 6 post treatment.

Quantitative Gene Transfection Studies:

To further confirm the results obtained by above experiment, quantitative gene transfection studies were performed. For this purpose, 300,000 adherent alveolar macrophage cells were inoculated in T25 flasks. Twelve hours post inoculation cells were treated with either NiE, ME, or GNP EGFP-N1 plasmid DNA-containing formulations mentioned above. One group of cells was treated with positively charged lipid Lipofectin® complexed with EGFP-N1, which served as a positive control. Additionally, cells treated with blank formulations served as negative controls. After the cells were treated with different formulations for six hours in serum free DMEM, they were incubated for a period of 24, 48, 72, 96, 120 and 144 hours at 37° C.

After completion of each time point total cytosolic proteins were extracted by cell lysis using 400 µl of cell lysis buffer at 4° C. Samples were stored at −80° C. until they were used for quantification of protein levels. BCA® (Biscinchoninic acid) protein assay by Thermo Fisher Scientific was used for estimation of total protein concentration. BCA assay involves reaction of amino acid residues with $Cu^{2+}$ ions which in turn leads to formation of $Cu^{1+}$ ions by a Biuret reaction. Cu$^{1+}$ ions formed in above reaction reacts with biscinchoninic acid resulting in formation of a soluble purple colored complex which exhibits linear absorbance at 562 nm. A calibration curve using different concentrations of albumin standard was plotted and used for estimation of total protein concentration from each sample. After estimation of total protein concentration green fluorescent protein specific ELISA was performed. ELISA plate for sandwich ELISA was prepared.

Towards this end, primary anti-EGFP monoclonal antibody (Novus Biologics, Littleton, Colo.) at 1:4,000 dilution was added to each well for attachment of the antibody to the bottom surface of each well. After 2 hours of incubation at room temperature, wells were washed 4 to 5 times with PBS-Tween80 to remove unbound antibodies. Then non-specific binding sites were then blocked by using starling superblock (Fisher Scientific, Milwaukee, Wis.). The wells were washed with PBS-Tween®80 four to five times. Then to each well 100 µl of known standard concentrations of GFP protein or 100 µl of cell supernatant obtained after cell lysis were added followed by overnight incubation at 4° C. Next, all of the wells were washed 4-5 times with PBS-Tween80 in order to remove any unbound protein and then secondary rabbit polyclonal anti-EGFP antibody attached to alkaline phosphatase enzyme (Novus Biologics, Littleton, Colo.) was added in each well. After two hours of incubation at room temperature wells were again washed 4-5 times with PBS-Tween80 in order to remove any unbound secondary antibody molecules. After this final washing step all wells were incubated with alkaline phosphate substrate for 30 minutes. Reaction was stopped by addition of 0.5 N NaOH and then absorbance was read at 408 nm using Bio-Tek® Synergy HT plate reader with KC4 software. Concentration of EGFP in samples was calculated from the standard calibration curve. Transfection efficiency was calculated as nanograms of EGFP present per milligram of total protein.

Qualitative Transgene Expression Analysis:

Fluorescence microscopy was used for qualitative determination of EGFP-N1 gene transfection. Microscopy images in FIG. 23(a-f) shows that maximum gene transfection was observed in cells treated with NiE formulations followed by ME and GNP formulations. Maximum green fluorescence was observed in cells treated with NiE formulation starting 24 hour post treatment with sustained levels at day 2, 3 and 4 followed by a decline at day 5 and 6. These results indicate that NiE formulation was better compared to ME or GNP formulations in causing gene transfection since NiE formulation offer more protection to plasmid DNA during formulation resulting in higher loading efficiency of plasmid DNA per ml of formulation as well as during intracellular transport of plasmid DNA in endosomal/lysozomal compartments.

5. Therapeutic IL-10 Gene Transfection Studies

Amplification, Purification and Isolation of mIL-10 Plasmid DNA from Transformed E. coli:

mIL-10 plasmid transformed E. coli bacteria were obtained from Invivogen (San Diego, Calif.). Liquid agar broth was prepared by dissolving 35 g of LB Agar powder obtained from Sigma Aldrich (St. Louis, Mo.) in 1 L deionized water and sterilized by autoclaving at 121° C. for 15 minutes. Lyophilized E. coli bacteria disc was suspended in liquid broth agar medium. The bacterial suspension was then streaked on solid agar plates and incubated for 12 hours at 37° C. for growth of bacterial colonies. After 12 hours, a single colony was picked using a sterile inoculation loop and transferred to liquid agar broth culture medium containing 10 µg/ml ampicillin for selection of transformed E. coli.

Culture flasks containing E. coli were incubated at 37° C. for 16 hours on a temperature regulated incubator shaker. Following this step, plasmid DNA extraction, purification and isolation was performed using Qiagen Plasmid Mega kits. Purity of plasmid DNA extracts was analyzed by measurement of A260/A280 values. Quantification of DNA concentration was carried out using PicoGreen® assay (Invitrogen, Carlsbad, Calif.). For determination of size of extracted plasmid mIL-10, agarose gel electrophoresis was performed either with undigested plasmid or plasmid digested with NheI and NcoI restriction enzymes obtained from New England Biolabs (Ipswich, Mass.).

RT-PCR Analysis for mIL-10 mRNA Expression:

Reverse transcriptase polymerase chain reaction is a technique for identification of gene expression at mRNA level. For qualitative analysis of IL-10 expression at the level of mRNA, 200,000 J774A.1 cells were incubated with NiE, ME, GNP, Lipofectin® or naked IL-10 plasmid for 6, 12 and 24 hours. After completion of each time point, total cellular RNA was extracted from cells using High Pure RNA Isolation Kit (Roche, Indianapolis, Ind.) as per the kit protocol. Quantification of isolated RNA was performed using Nano-Drop® 2000c instrument (Thermo-Fisher Scientific, Wilmington, Del.). The isolated RNA fractions were converted to final PCR products using selective primers for IL-10 and beta-actin using One Step RT-PCR kit (Qiagen, Valencia, Calif.) as per kit manufacturer protocol. The forward and reverse primer sequences used for conversion of IL-10 mRNA in to cDNA were 5'-CCAGCCTTATCGGAAATGA-3' and 5'-TCTCACCCAGGGAATTCAAA-3' respectively. The forward and reverse primer sequences used for conversion of β-actin mRNA into cDNA were 5'-GTTAC-CAACTGGGACGACA-3' and 5'-TGGCCATCTCCT-GCTCGAA-3' respectively. The amount of template RNA added for each reaction was 1 µg. PCR cycler settings for cDNA amplification are shown in Table 10. Final PCR products were run on 1.2% agarose E-gels (Invitrogen, CA) for visualization of cDNA bands using Kodak UV/NIR image station.

TABLE 10

PCR cycler settings for RT-PCR experiments

| Step | Temperature (degrees Celsius) | Time (minutes) |
| --- | --- | --- |
| Reverse Transcription | 50 | 30 |
| Initial PCR Activation | 95 | 15 |
| 3-Step PCR Cycling | | |
| Denaturation | 94 | 1 |
| Annealing | 60 | 1 |
| Extension | 72 | 1 |
| Number of Cycles - 35 | | |
| Final Extension | 72 | 10 |

Quantitative mIL-10 Transfection Studies with ELISA:

For quantitative analysis of mIL-10 gene expression caused by naked plasmid mIL-10, NiE, ME or GNP mIL-10 specific ELISA was performed. Towards this end, 200,000 J774A.1 cells were plated in different wells of six well plates. Following cell attachment, cells were treated with mIL-10 containing formulations in serum free DMEM media for six hours. Following six hours, cell culture medium was completely replaced with fresh DMEM medium containing 10% FBS. Cell culture supernatant was collected at 12 hours, 24 hours, 48 hours, 72 hours and 96 hours time points and stored at −80° C.

Colorimetric sandwich ELISA plates for mIL-10 protein were purchased from R&D Systems (Minneapolis, Minn.). ELISA assay was performed as per the kit protocol. Briefly, 50 µl of assay diluent and 50 µl of standard, sample or control were added to different wells. After gentle mixing, plates were covered with a plate sealer and incubated for two hours. After two hours solution from each well was aspirated and wells were washed 5 times with 1× wash buffer. After this step, 100 µl of secondary antibody conjugated with horseradish peroxidase was added to each well and incubated for two hours. After two hours, again contents from each well was aspirated and wells were washed 5-times with 1× wash buffer. Followed by this step, 100 µl of substrate solution containing hydrogen peroxide and tetramethyl benzidine was added into each well and incubated for 30 minutes protected from light. At the end of 30 minutes, stop solution containing diluted hydrochloric acid was added and absorbance at 450 nm with correction wavelength at 540 nm using BioTek Synergy HT (Winooski, Vt.) plate reader using KC4 software.

Figure 24:
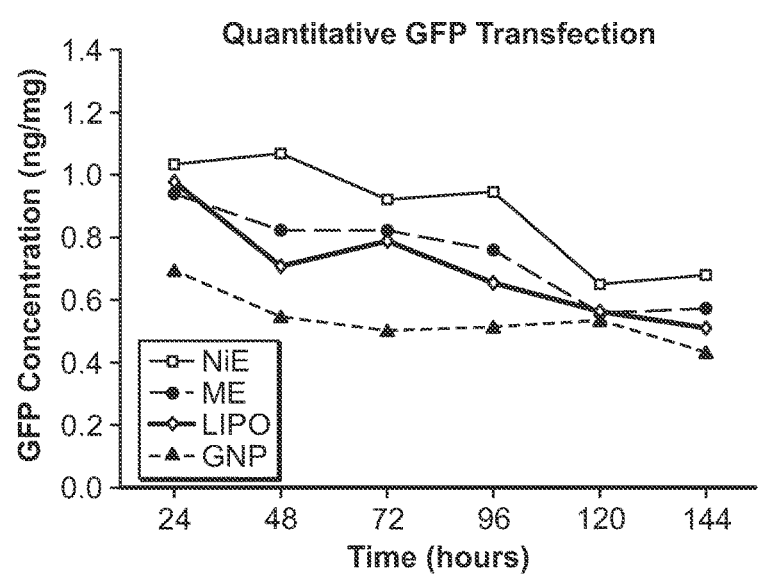
FIG. 24: Quantitative green fluorescent protein (GFP) expression by ELISA showing transgene expression with EGFP-N1 plasmid DNA encapsulated in GNP, ME, and NiE as well as complexed with Lipofectin®. Highest levels of GFP expression was observed with NiE formulation relative to all other tested.

Quantitative Transgene Expression Studies:

Quantitative evaluation of EGFP-N1 gene transfection was performed using EGFP-N1 ELISA. The results shown in FIG. 24 show that NiE formulation was the most effective in causing gene transfection followed by ME and GNP formulations. NiE showed highest levels of gene transfection 24 hour post transfection with sustained levels till day 4 followed by a decline at day 5 and 6.

6. IL-10 Gene Transfection Mediated Suppression of Pro-Inflammatory Cytokines

In order to evaluate IL-10 gene transfection mediated suppression of pro-inflammatory cytokines such as TNFα and IL1β, LPS stimulation studies were performed. Towards this end, 200,000 J774A.1 cells were plated in different wells of six well plates. Following cell attachment, cells were treated with mIL-10 containing formulations in serum free DMEM media for six hours. Following six hours, cell culture medium was completely replaced with fresh DMEM medium containing 10% FBS. Cell culture supernatant was collected at 12 hours, 24 hours and 48 hour time points. Six hours prior to each time point, lipopolysaccharide (LPS) was added to each well at final concentration of 100 ng/ml in each well. RT PCR analysis was used for detection of TNFα and IL1β mRNA levels at each time point. TNFα and IL1β specific ELISA assay plates obtained from R&D systems (Minneapolis, Minn.) were used for detection of TNFα and IL1β protein levels in cell culture supernatant at each time point.

TNFα and IL1β RT-PCR Analysis:

After completion of each time point, total cellular RNA was extracted from cells using High Pure RNA Isolation Kit (Roche, Germany) as per the kit protocol. Quantification of isolated RNA was performed using NanoDrop® 2000c instrument (Thermo-Scientific, Delaware). The isolated RNA fractions were converted to final PCR products using selective primers for TNFα and IL1β and beta-actin using One Step RT-PCR kit (Qiagen, Valencia, Calif.) as per kit manufacturer protocol. The forward and reverse primer sequences used for conversion of mRNA into cDNA for TNFα were 5'-CATGAGCACAGAAAGCATGATC-3' and 5'-CCTTCTCCAGCTGGAAGACT-3' respectively. The forward and reverse primer sequences used for conversion of mRNA into cDNA for IL-1β were 5'-GGCTGCTTC-CAAACCTTTGA-3' and 5'-GCTCATATGGGTC-CGACAGC-3' respectively. The amount of template RNA added for each reaction was 1 ug. PCR cycler settings for cDNA amplification are shown in Table 10. Final PCR products were run on 1.2% agarose E-gels® (Invitrogen, Carlsbad, Calif.) for visualization of cDNA bands using Kodak UV/NIR image station.

TNFα and IL1β ELISA Analysis:

ELISA assays were performed as per the kit protocols. Briefly, 50 µl of assay diluent and 50 µl of standard, sample or control were added to different wells in both plates. After gentle mixing, plates were covered with a plate sealer and incubated for two hours. After two hours solution from each well was aspirated and wells were washed 5 times with 1× wash buffer. After this step, 100 µl of secondary antibody conjugated with horse-radish peroxidase was added to each well and incubated for two hours. After two hours, again contents from each well was aspirated and wells were washed 5 times with 1× wash buffer. Followed by this step, 100 µl of substrate solution containing hydrogen peroxide and tetramethyl benzidine was added into each well and incubated for 30 minutes protected from light. At the end of 30 minutes, stop solution containing diluted hydrochloric acid was added to both the plates and absorbance at 450 nm with correction wavelength at 540 nm using BioTek Synergy HT plate reader using KC4 software.

Isolation of mIL-10 Plasmid DNA from Transformed *E. coli*:

For determination of purity of plasmid extraction, A260/A280 ratio was determined. A260/280 values for all extractions was within the window of 1.9 to 2.0 which indicated plasmid extracts contained none or negligible protein contamination. Further, when plasmid extracts were run on 1.2% agarose E-gels®, an intact DNA band of size approximately 3.7 kilobase pair was observed. In order to determine presence of IL-10 transgene in the extracted plasmid, plasmid extract was digested with two restriction enzymes NheI and NcoI. When digested plasmid was run on 1.2% agarose E-gel, a band at approximately 500 bps was observed which co-related with size of IL-10 transgene as described by IL-10 transformed *E. coli* supplier FIG. 25. These results show that mIL-10 plasmid was isolated and purified such that it was free from protein or genomic nucleic acid impurities in stable form.

RT-PCR Analysis for mIL-10 mRNA Expression:

Results obtained from IL-10 RT-PCR showed highest expression of IL-10 mRNA in cells treated with NiE formulation followed by ME and GNP formulations at different time points. Compared to Lipofectamine, a standard transfecting reagent, NiE showed higher IL-10 mRNA expression. Results are shown in FIG. 26.

Figure 27:
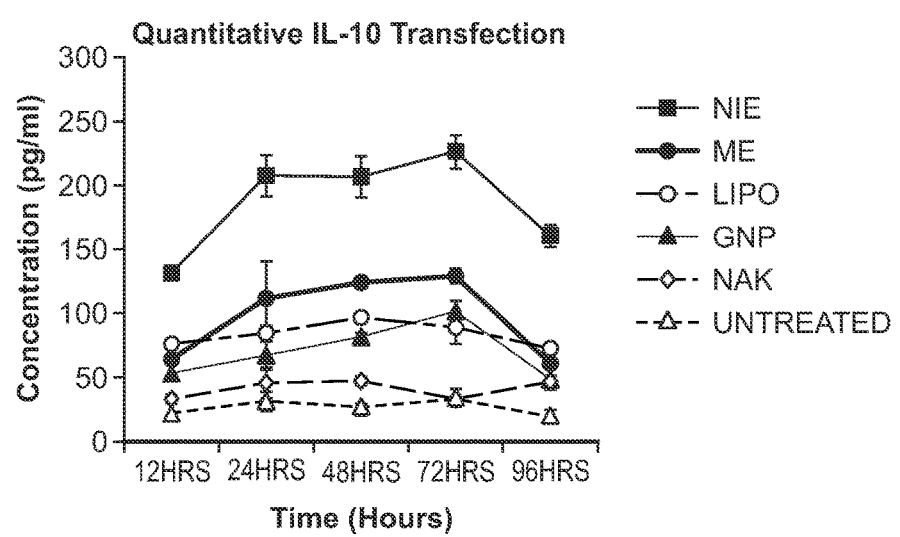
FIG. 27: Quantitative IL-10 protein expression by ELISA showing transgene expression with mIL-10 plasmid DNA encapsulated in GNP, ME, and NiE as well as complexed with Lipofectin®. Highest levels of mIL10 expression were observed with NiE formulation relative to all other tested.

Quantitative mIL-10 Gene Transfection Studies with ELISA:

Results obtained from mIL-10 ELISA correlated with IL-10 RT-PCR experiment where NiE formulation showed highest gene transfection efficiency followed by ME and GNP. ELISA results are graphed in FIG. 27.

Figure 28:
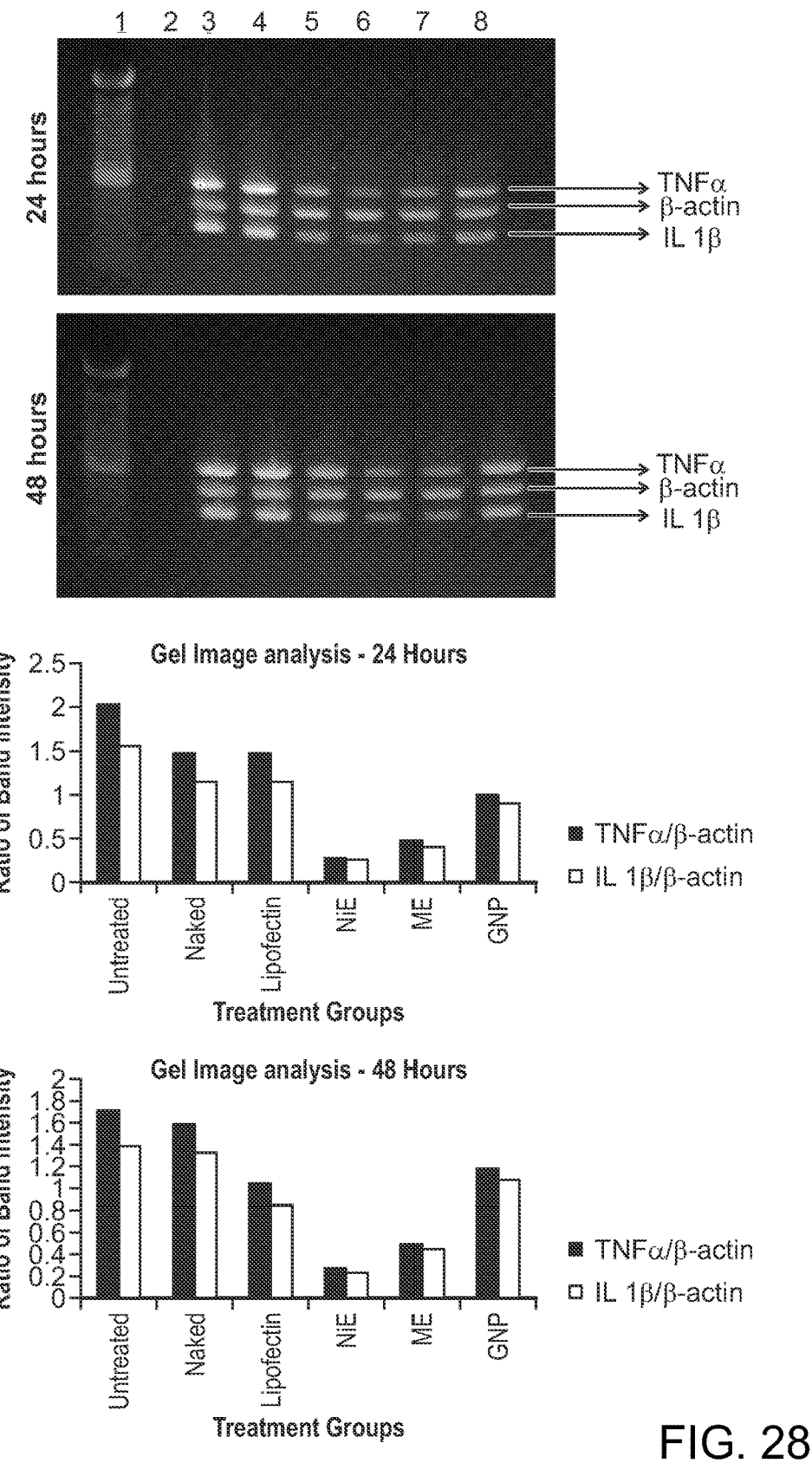
FIG. 28: RT-PCR analysis for TNFα and IL1β mRNA in untreated cells (lane 3) or treated with naked plasmid (lane 4), mIL10 plasmid complexed with Lipofectin® (lane 5), mIL10 plasmid in NiE (lane 6), mIL10 plasmid in ME (lane 7) or mIL10 plasmid in GNP (lane 8) at 24 hour and 48 hour time points after LPS stimulation.

TNFα and IL1β RT-PCR Analysis:

LPS triggered expression and release of pro-inflammatory cytokines was evaluated using RT-PCR analysis. At the end of 12 hour and 48 hour time points, levels of TNFα and IL1β in cells pretreated with IL-10 gene containing formulations was lower compared to untreated cells. Among the different formulations tested, NiE formulation which was most efficient in causing mIL-10 gene transfection showed highest suppression of TNFα and IL1β gene transcription followed by ME and GNP formulations. Results of this study are shown in FIG. 28.

Figure 29:
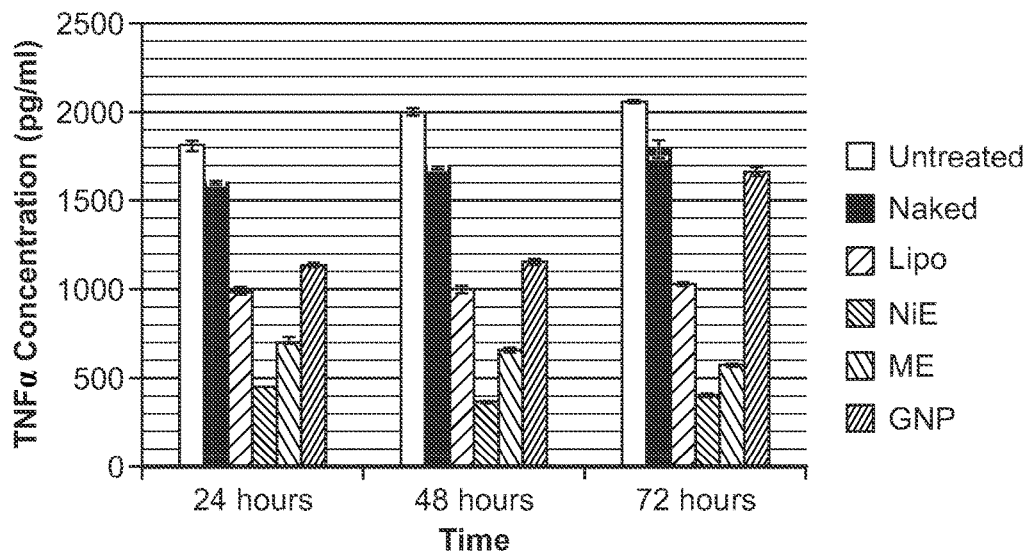
FIG. 29: Quantitative TNFα protein expression by ELISA showing IL-10 transfection mediated suppression of TNFα in either untreated J774A.1 cells or J774A.1 cells transfected with mIL-10 containing NiE, ME, GNP, Lipofectin® or naked mIL-10 plasmid.
Figure 30:
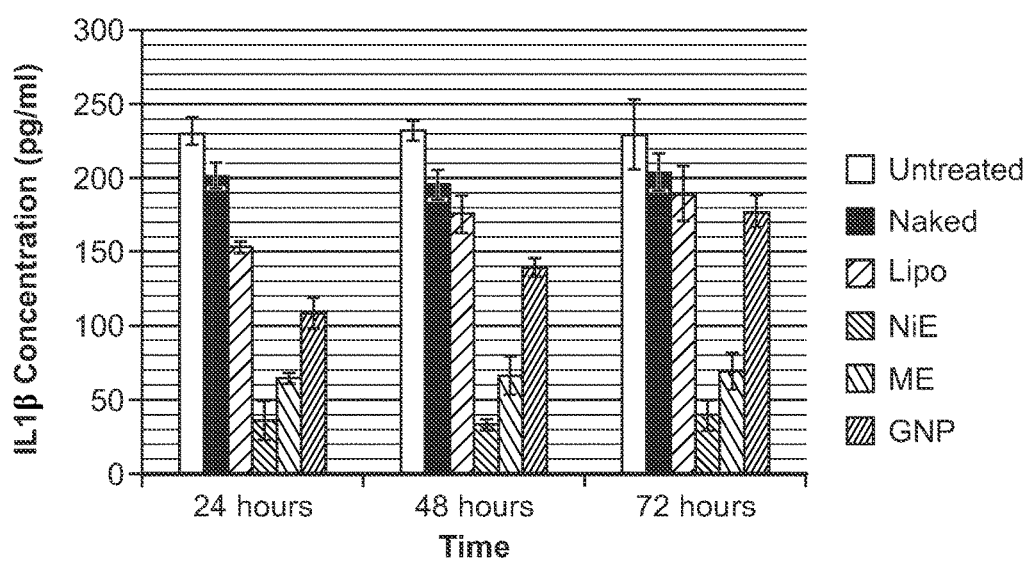
FIG. 30: Quantitative IL1β protein expression by ELISA showing IL-10 transfection mediated suppression of IL1β in either untreated J774A.1 cells or J774A.1 cells treated with mIL-10 containing NiE, ME, GNP, Lipofectin or naked mIL-10 plasmid.

TNFα and IL1β Expression Analysis by ELISA:

ELISA for TNFα and IL1β was performed in order to quantitate levels of these cytokines in cell culture supernatant at different time points following LPS stimulation on IL-10 transfected J774A.1 cells. The results (FIGS. 29 and 30) showed highest suppression of both TNFα and IL1β in cells treated with NiE followed by ME and GNP formulations. These results indicate that IL-10 plasmid delivered through NiE has therapeutic activity where it can suppress expression of pro inflammatory cytokines such as TNFα and IL1β.

The results of this study show that DNA-containing solid gelatin nanoparticles can be encapsulated in the innermost aqueous phase of the W/O/W multiple emulsions to form NiE formulations. EGFP-N1 or mIL-10 plasmid DNA-loaded NiE formulations were capable of producing sustained gene transfection in J774A.1 murine adherent alveolar macrophage cell lines. Moreover, it was found that plasmid EGFP-N1 or mIL-10 encapsulated in NiE had superior gene transfection efficiency compared to plasmid EGFP-N1 or mIL-10 encapsulated in ME or GNP or complexed with Lipofectin®, a cationic-lipid based transfection reagent. Furthermore, it was confirmed that mIL-10 delivered through NiE was capable of down regulating levels of proinflammatory cytokines TNFα and IL1β in LPS stimulated J774A.1 cells.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

REFERENCES

The following references are hereby incorporated by reference in their entirety:

K. K. Nagatoshi Fujiwara. Macrophages in Inflammation. Current Drug targets-Inflammation & Allergy. 5:281-286 (2005).

M. F. Lopes, C. G. Freire-de-Lima, and G. A. DosReis. The macrophage haunted by cell ghosts: a pathogen grows. Immunology today. 21:489-494 (2000).

C. O. Elson, M. Tomasi, M. T. Dertzbaugh, G. Thaggard, R. Hunter, and C. Weaver. Oral-antigen delivery by way of a multiple emulsion system enhances oral tolerance. Ann N Y Acad. Sci. 778:156-162 (1996).

A. Suzuki, M. Morishita, M. Kajita, K. Takayama, K. Isowa, Y. Chiba, S. Tokiwa, and T. Nagai. Enhanced colonic and rectal absorption of insulin using a multiple emulsion containing eicosapentaenoic acid and docosahexaenoic acid. J Pharm Sci. 87:1196-1202 (1998).

A. Shahiwala and M. M. Amiji. Enhanced mucosal and systemic immune response with squalane oil-containing multiple emulsions upon intranasal and oral administration in mice. J Drug Target. 16:302-310 (2008).

B. Bozan and F. Temelli. Chemical composition and oxidative stability of flax, safflower and poppy seed and seed oils. Bioresour Technol. 99:6354-6359 (2008).

C. Masterjohn. The anti-inflammatory properties of safflower oil and coconut oil may be mediated by their respective concentrations of vitamin E. J Am Coll Cardiol. 49:1825-1826 (2007).

S. Devaraj and I. Jialal. Alpha-tocopherol decreases tumor necrosis factor-alpha mRNA and protein from activated human monocytes by inhibition of 5-lipoxygenase. Free Radic Biol Med. 38:1212-1220 (2005).

S. Devaraj and I. Jialal. Alpha-tocopherol decreases interleukin-1 beta release from activated human monocytes by inhibition of 5-lipoxygenase. Arterioscler Thromb Vasc Biol. 19:1125-1133 (1999).

M. De Bandt, M. Grossin, F. Driss, J. Pincemail, C. Babin-Chevaye, and C. Pasquier. Vitamin E uncouples joint destruction and clinical inflammation in a transgenic mouse model of rheumatoid arthritis. Arthritis Rheum. 46:522-532 (2002).

Alexis, et al. DNA vaccination as anti-inflammatory strategy. In P. D. R. C. H. Evans (Ed), Gene Therapy in Inflammatory Diseases, Progress in Inflammation Research, Birhauser Verlag, Basel, Switzerland, 2000, pp. 205-230.

R. J. Mrsny. Tissue-and Cell-Specific Targeting for the Delivery of Genetic Information. In M. M. Amiji (Ed), Polymeric Gene Delivery: Principles and Applications, CRC Press, Boca Raton, Fla. 2005, pp. 5-27.

Pack, D. W., et al., Design and development of polymers for gene delivery. Nat Rev Drug Discov, 2005. 4(7): 581-93.

Glover, D. J., H. J. Lipps, and D. A. Jans, Towards safe, non-viral therapeutic gene expression in humans. Nat Rev Genet, 2005. 6(4): 299-310.

Kaul, G. and M. Amiji, Tumor-targeted gene delivery using poly(ethylene glycol)-modified gelatin nanoparticles: in vitro and in vivo studies. Pharm Res, 2005. 22(6): 951-61.

Bhavsar, M. D. and M. M. Amiji, Oral IL-10 gene delivery in a microsphere-based formulation for local transfection and therapeutic efficacy in inflammatory bowel disease. Gene Ther, 2008. 15(17): p. 1200-9.

Shahiwala, A. and M. M. Amiji, Enhanced mucosal and systemic immune response with squalane oil-containing multiple emulsions upon intranasal and oral administration in mice. J Drug Target, 2008. 16(4): p. 302-10.

Bouma, G. & Strober, W. The immunological and genetic basis of inflammatory bowel disease. Nature Reviews Immunology 3, 521-533 (2003).

Strober, W., Fuss, I. & Mannon, P. The fundamental basis of inflammatory bowel disease. Journal of Clinical Investigation 117, 514-521 (2007).

Ardizzone, S. & Porro, G. B. Biologic therapy for inflammatory bowel disease. Drugs 65, 2253-2286 (2005).

Oldenburg, B. & Hommes, D. Biological therapies in inflammatory bowel disease: top-down or bottom-up? Current Opinion in Gastroenterology 23, 395-399 (2007).

Mueller, C. Tumour necrosis factor in mouse models of chronic intestinal inflammation. Immunology 105, 1-8 (2002).

Sandborn, W. J. Strategies for targeting tumour necrosis factor in IBD. Best Practice & Research in Clinical Gastroenterology 17, 105-117 (2003).

van Deventer, S. J. H. New biological therapies in inflammatory bowel disease. Best Practice & Research in Clinical Gastroenterology 17, 119-130 (2003).

Papa, A. et al. Biological therapies for inflammatory bowel disease: controversies and future options. Expert Review of Clinical Pharmacology 2, 391-403 (2009).

Hoentjen, F. & Van Bodegraven, A. A. Safety of anti-tumor necrosis factor therapy in inflammatory bowel disease. World Journal of Gastroenterology 15, 2067-2073 (2009).

Mannon, P. J. et al. Anti-Interleukin-12 Antibody for Active Crohn's Disease. The New England Journal of Medicine 351, 2069-2079 (2004).

Ito, H. et al. A pilot randomized trial of a human anti-Interleukin-6 receptor monoclonal antibody in active Crohn's disease. Gastroenterology 126, 989-996 (2004).

Sandborn, W. J. et al. Natalizumab induction and maintenance therapy for Crohn's disease. New England Journal of Medicine 353, 1912-1925 (2005).

Feagan, B. G. et al. Treatment of ulcerative colitis with a humanized antibody to the alpha4beta7 integrin. New England Journal of Medicine 352, 2499-2507 (2005).

Sorensen, D. R., Leirdal, M. & Sioud, M. Gene silencing by systemic delivery of synthetic siRNAs in adult mice. Journal of Molecular Biology 327, 761-766 (2003).

MacDiamid, J. A. et al. Sequential treatment of drug-resistant tumors with targeted minicells containing siRNA or a cytotoxic drug. Nature Biotechnology 27, 643-U697 (2009).

Kortylewski, M. et al. In vivo delivery of siRNA to immune cells by conjugation to a TLR9 agonist enhances antitumor immune responses. Nature Biotechnology 27, 925-932 (2009).

Choi, B. et al. Tumor necrosis factor alpha small interfering RNA decreases herpes simplex virus-induced inflammation in a mouse model. Journal of Dermatological Science 52, 87-97 (2008).

Peer, D., Park, E. J., Morishita, Y., Carman, C. V. & Shimaoka, M. Systemic leukocyte-directed siRNA delivery revealing cyclin D1 as an anti-inflammatory target. Science 319, 627-630 (2008).

Aouadi, M. et al. Orally delivered siRNA targeting macrophage Map4k4 suppresses systemic inflammation. Nature 458, 1180-U1116 (2009).

Sioud, M. On the delivery of small interfering RNAs into mammalian cells. Expert Opinion on Drug Delivery 2, 639-651 (2005).

Xu, D. et al. Delivery of MDR1 small interfering RNA by self-complementary recombinant adeno-associated virus vector. Molecular Therapy 11, 523-530 (2005).

Fattal, E. & Bochot, A. State of the art and perspectives for the delivery of antisense oligonucleotides and siRNA by polymeric nanocarriers. International Journal of Pharmaceutics 364, 237-248 (2008).

Bhavsar, M. D. & Amiji, M. M. Gastrointestinal distribution and in vivo gene transfection studies with nanoparticles-in-microsphere oral system (NiMOS). Journal of Controlled Release 119, 339-348 (2007).

Bhavsar, M. D. & Amiji, M. M. Oral IL-10 gene delivery in a microsphere-based formulation for local transfection and therapeutic efficacy in inflammatory bowel disease. Gene Therapy 15, 1200-1209 (2008).

Melgar, S., Karlsson, A. & Michaelsson, E. M. Acute colitis induced by dextran sulfate sodium progresses to chronicity in C57BL/6 but not in BALB/c mice: correlation between symptoms and inflammation. American Journal of Physiology-Gastrointestinal and Liver Physiology 288, G1328-G1338 (2005).

Okayasu, I. et al. A NOVEL METHOD IN THE INDUCTION OF RELIABLE EXPERIMENTAL ACUTE AND CHRONIC ULCERATIVE-COLITIS IN MICE. Gastroenterology 98, 694-702 (1990).

Grisham, M. B., Benoit, J. N. & Granger, D. N. ASSESSMENT OF LEUKOCYTE INVOLVEMENT DURING ISCHEMIA AND REPERFUSION OF INTESTINE. Methods in Enzymology 186, 729-742 (1990).

Bhavsar, M. D. & Amiji, M. M. Development of novel biodegradable polymeric nanoparticles-in-microsphere formulation for local plasmid DNA delivery in the gastrointestinal tract. Aaps Pharmscitech 9, 288-294 (2008).

Bhavsar, M. D. & Amiji, M. M. Polymeric nano- and microparticle technologies for oral gene delivery. Expert Opinion on Drug Delivery 4, 197-213 (2007).

Kaul, G. & Amiji, M. Tumor-targeted gene delivery using poly(ethylene glycol)-modified gelatin nanoparticles: in vitro and in vivo studies. Pharmaceutical Research 22, 951-961 (2005).

Pender, S. L.-F. et al. Systemic administration of the chemokine macrophage inflammatory protein 1a exacerbates inflammatory bowel disease in a mouse model. Gut 54, 1114-1120 (2005).

Bhavsar, M. D., Tiwari, S. B. & Amiji, M. M. Formulation optimization for the nanoparticles-in-microsphere hybrid oral delivery system using factorial design. Journal of Controlled Release 110, 422-430 (2006).

Diez, S. & de Ilarduya, C. T. Versatility of biodegradable poly(D,L-lactic-co-glycolic acid) microspheres for plasmid DNA delivery. European Journal of Pharmaceutics and Biopharmaceutics 63, 188-197 (2006).

Tracy, M. Development and scale-up of a microsphere protein delivery system. Biotechnological Progress 14, 108-115 (1998).

Barbara, G., Xing, Z., Hogaboam, C. M., Gauldie, J. & Collins, S. M. Interleukin 10 gene transfer prevents experimental colitis in rats. Gut 46, 344-349 (2000).

The invention claimed is:

1. A method of imaging a macrophage with a multicompartment delivery system, the method comprising:
(a) administering an effective amount of the multicompartment delivery system to a subject, the multicompartment delivery system comprising one or more inner aqueous compartments encapsulated within an outer hydrophobic compartment, the outer hydrophobic compartment encapsulated in an exterior aqueous compartment; wherein the one or more inner aqueous compartments comprise a nanoparticle consisting of a polymeric matrix, at least one imaging agent, and optionally at least one therapeutic agent; and wherein the outer hydrophobic compartment is 0.5 to 20 microns in size and comprises an oil;
(b) allowing the multicompartment delivery system to deliver the imaging agent to a macrophage; and
(c) detecting the imaging agent in the subject.

2. The method of claim 1, wherein the imaging agent is selected from the group consisting of colloidal gold, iron-oxide crystals, and quantum dots.

3. The method of claim 1, wherein the imaging agent is selected from the group consisting of fluorophores, radiolabels, X-ray contrast agents, and positron emission tomographic agents.

4. The method of claim 1, wherein the imaging agent is a fluorophore.

5. The method of any one of claims 2, 3, and 4, wherein the nanoparticle consists of a polymeric matrix, an imaging agent, and a therapeutic agent.

6. The method of claim 1, wherein the nanoparticle consists of a polymeric matrix and two imaging agents.

7. The method of claim 6, wherein each of the imaging agents is selected from the group consisting of fluorophores, radiolabels, X-ray contrast agents, and positron emission tomographic agents.

8. The method of claim 5, wherein the therapeutic agent is selected from the group consisting of chemotherapeutics, antibiotics, antivirals, small molecules, anti-inflammatory agents, siRNA, and DNA.

9. The method of claim 1, wherein the polymeric matrix comprises poly(epsiloncaprolactone), gelatin, or alginate.

10. The method of claim 1, wherein the polymeric matrix is hydrophilic.

11. The method of claim 1, wherein the oil is safflower oil.

12. A method of treating a disease with a multicompartment delivery system for targeting a macrophage, the method comprising:
(a) administering an effective amount of the multicompartment delivery system to a subject, the multicompartment delivery system comprising one or more inner aqueous compartments encapsulated within an outer hydrophobic compartment, the outer hydrophobic compartment encapsulated in an exterior aqueous compartment; wherein the one or more inner aqueous compartments comprise a nanoparticle consisting of a polymeric matrix, at least one therapeutic agent, and optionally at least one imaging agent; and wherein the outer hydrophobic compartment is 0.5 to 20 microns in size and comprises an oil; and
b) allowing the multicompartment delivery system to deliver the therapeutic agent to a macrophage.

13. The method of claim 12, wherein the disease is selected from the group consisting of atherosclerosis, Crohn's disease, inflammatory bowel disease, rheumatoid arthritis and cancer.

14. The method of claim 12, wherein the nanoparticle consists of a polymeric matrix, an imaging agent, and at least one therapeutic agent.

15. The method of claim 14, wherein the imaging agent is selected from the group consisting of colloidal gold, iron-oxide crystals, and quantum dots.

16. The method of claim 14, wherein the imaging agent is selected from the group consisting of fluorophores, radiolabels, X-ray contrast agents, and positron emission tomographic agents.

17. The method of claim 14, wherein the imaging agent is a fluorophore.

18. The method of claim 12, wherein the therapeutic agent is selected from the group consisting of chemotherapeutics, anti-inflammatories, fatty acids, antibiotics, antivirals, small molecules, siRNA, and DNA.

19. The method of claim 12, wherein the multicompartment delivery system further comprises a second therapeutic agent selected from the group consisting of chemotherapeutics, antiinflammatories, fatty acids, antibiotics, antivirals, small molecules, siRNA, and DNA.

20. The method of claim 19, wherein the outer hydrophobic compartment encapsulates the second therapeutic agent.

21. The method of claim 19, wherein the nanoparticle consists of a polymeric matrix, an imaging agent, and two therapeutic agents.

22. The method of any one of claims 12, 13, or 14-21, wherein the polymeric matrix comprises poly(epsilon-caprolactone), gelatin, or alginate.

23. The method of any one of claims 12, 13, or 14-21, wherein the polymeric matrix is hydrophilic.

24. The method of claim 12, wherein the oil is safflower oil.

25. The method of claim 12, wherein the therapeutic agent is a gene construct.

26. The method of claim 25 wherein the gene construct is expressed in the macrophage.

27. The method of claim 25, wherein the gene construct encodes IL-10.

28. The method of claim 25, wherein the gene construct causes apoptosis in the macrophage.

29. The method of claim 25, wherein the gene construct is siRNA.

* * * * *